(12) United States Patent
Nakanishi et al.

(10) Patent No.: US 10,227,493 B2
(45) Date of Patent: Mar. 12, 2019

(54) METHOD FOR PRODUCING SURFACE-MODIFIED BASE MATERIAL, METHOD FOR PRODUCING JOINED BODY, NEW HYDROSILANE COMPOUND, SURFACE TREATMENT AGENT, SURFACE TREATMENT AGENT KIT, AND SURFACE-MODIFIED BASE MATERIAL

(71) Applicant: KYOTO UNIVERSITY, Kyoto-shi, Kyoto (JP)

(72) Inventors: Kazuki Nakanishi, Kyoto (JP); Nirmalya Moitra, Mumbai (IN); Kazuyoshi Kanamori, Kyoto (JP); Toyoshi Shimada, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 15/125,017

(22) PCT Filed: Mar. 9, 2015

(86) PCT No.: PCT/JP2015/001277
§ 371 (c)(1),
(2) Date: Sep. 9, 2016

(87) PCT Pub. No.: WO2015/136913
PCT Pub. Date: Sep. 17, 2015

(65) Prior Publication Data
US 2017/0022223 A1 Jan. 26, 2017

(30) Foreign Application Priority Data

Mar. 10, 2014 (JP) ................... 2014-046102
Dec. 26, 2014 (JP) ................... 2014-266211

(51) Int. Cl.

| | | |
|---|---|---|
| *C09C 1/30* | (2006.01) | |
| *C08B 15/05* | (2006.01) | |
| *C04B 35/628* | (2006.01) | |
| *C09C 1/00* | (2006.01) | |
| *B01J 31/14* | (2006.01) | |
| *C07F 9/535* | (2006.01) | |
| *C07F 17/02* | (2006.01) | |
| *C07F 9/40* | (2006.01) | |
| *C07F 7/08* | (2006.01) | |
| *C03C 17/30* | (2006.01) | |
| *C09D 5/16* | (2006.01) | |
| *D06M 13/513* | (2006.01) | |
| *D06M 101/24* | (2006.01) | |
| *D06M 101/32* | (2006.01) | |
| *D21C 9/00* | (2006.01) | |
| *D21H 25/02* | (2006.01) | |

(52) U.S. Cl.
CPC ............ *C09C 1/3081* (2013.01); *B01J 31/14* (2013.01); *C03C 17/30* (2013.01); *C04B 35/628* (2013.01); *C04B 35/62805* (2013.01); *C04B 35/62807* (2013.01); *C04B 35/62813* (2013.01); *C04B 35/62815* (2013.01); *C04B 35/62821* (2013.01); *C04B 35/62823* (2013.01); *C04B 35/62886* (2013.01); *C07F 7/0838* (2013.01); *C07F 7/0896* (2013.01); *C07F 9/4012* (2013.01); *C07F 9/5355* (2013.01); *C07F 17/02* (2013.01); *C08B 15/05* (2013.01); *C09C 1/00* (2013.01); *C09C 1/30* (2013.01); *C09C 1/3063* (2013.01); *C09C 1/3072* (2013.01); *C09D 5/1681* (2013.01); *D06M 13/513* (2013.01); *C04B 2235/3218* (2013.01); *C04B 2235/3232* (2013.01); *C04B 2235/3244* (2013.01); *C04B 2235/3286* (2013.01); *C04B 2235/3418* (2013.01); *C04B 2235/3445* (2013.01); *C04B 2235/483* (2013.01); *D06M 2101/24* (2013.01); *D06M 2101/32* (2013.01); *D06M 2200/12* (2013.01); *D06M 2400/01* (2013.01); *D21C 9/005* (2013.01); *D21H 25/02* (2013.01)

(58) Field of Classification Search
CPC .......... C03C 17/30; C08K 9/06; C08G 77/38; C08G 77/385; C08G 77/388
USPC ............................... 428/403–407; 528/25–28
See application file for complete search history.

(56) References Cited

U.S. PATENT DOCUMENTS 4,011,247 A * 3/1977 Sato ..................... C07F 7/0896
528/15
4,157,357 A 6/1979 Mine et al.
(Continued)

FOREIGN PATENT DOCUMENTS

CN 102875814 1/2013
EP 1116753 A2 * 7/2001
(Continued)

OTHER PUBLICATIONS

Maeda, et al., "Absorption and Fluorescence Spectroscopic Properties of 1- and 1,4-Silyl-Substituted Naphthalene Derivatives", Molecules, vol. 17, pp. 5108-5125, 2012.
(Continued)

*Primary Examiner* — Marc S Zimmer
(74) *Attorney, Agent, or Firm* — Hamre, Schumann, Mueller & Larson, P.C.

(57) ABSTRACT

The method for producing a surface-modified base material according to the present invention includes a step of bringing a base material having a polar group present on a surface thereof into contact with a hydrosilane compound having a molecular structure A and having a Si—H group composed of a silicon atom of the molecular structure A and a hydrogen atom bonded to the silicon atom in the presence of a borane catalyst so as to allow a dehydrocondensation reaction to take place between the base material and the compound, thereby forming the base material surface-modified with the molecular structure A. This production method is capable of surface-modifying a base material at a lower temperature in a shorter time than conventional methods and allows a wide variety of options for the form, type, and application of the base material, the mode of the modification reaction, and the type of the molecular structure with which the base material is surface-modified.

17 Claims, 40 Drawing Sheets

(56) References Cited

U.S. PATENT DOCUMENTS

| | | | |
|---|---|---|---|
| 4,743,648 A * | 5/1988 | Hill | C09G 1/16 106/10 |
| 5,246,740 A | 9/1993 | Mino et al. | |
| 5,624,875 A | 4/1997 | Nakanishi et al. | |
| 6,316,057 B1 | 11/2001 | Hirayama et al. | |
| 6,743,883 B1 | 6/2004 | Frances et al. | |
| 8,629,222 B2 | 1/2014 | Takizawa et al. | |
| 2003/0139287 A1* | 7/2003 | Deforth | C08G 77/08 502/202 |
| 2004/0048975 A1 | 3/2004 | Frances | |
| 2006/0041097 A1 | 2/2006 | Herrwerth et al. | |
| 2013/0190470 A1* | 7/2013 | Marrot | C08G 77/38 528/27 |

FOREIGN PATENT DOCUMENTS

| | | |
|---|---|---|
| EP | 1 627 892 | 2/2006 |
| JP | 52-147657 | 12/1977 |
| JP | 4-214880 | 8/1992 |
| JP | 6-130716 | 5/1994 |
| JP | 6-265534 | 9/1994 |
| JP | 7-041374 | 2/1995 |
| JP | 2001-335585 | 12/2001 |
| JP | 2002-507146 | 3/2002 |
| JP | 2003531925 | 10/2003 |
| JP | 2004-175793 | 6/2004 |
| JP | 2005-219959 | 8/2005 |
| JP | 2009-149454 | 7/2009 |
| JP | 2009-256670 | 11/2009 |
| JP | 2010-090007 | 4/2010 |
| JP | 2010-090008 | 4/2010 |
| JP | 2010-265174 | 11/2010 |
| WO | 01/58562 | 8/2001 |
| WO | 2007/021037 | 2/2007 |

OTHER PUBLICATIONS

Nlate, at al., "Molecular Batteries: Ferrocenylsilylation of Dendrons, Dendritic Cores, and Dendrimers: New Convergent and Divergent Routes to Ferrocenyl Dendrimers with Stable Redox Activity", Chemistry—A European Journal, vol. 6, No. 14, pp. 2544-2553, 2000.

Moitra, et al., "Surface Functionalization of Silica by Si—H Activation of Hydrosilanes", Journal of the American Chemical Society, vol. 136, pp. 11570-11573, 2014.

Mizerska, et al., "Polysiloxane cationic biocides with imidazolium salt (ImS) groups, synthesis and antibacterial properties",European Polymer Journal, vol. 45, pp. 779-787, 2009.

Mieczynska, et al., "Palladium supported on triazolyl-functionalized polysiloxane as recyclable catalyst for Suzuki-Miyaura Cross-coupling", Applied Catalysis A: General, vol. 470, pp. 24-30, 2014.

Partial Supplementary European Search Report issued for corresponding European Patent Application No. 15761505.5, dated Jan. 23, 2018, 12 pages.

Zhou, D. et al., "Tris(pentafluorophenyl)borane as a Superior Catalyst in the Synthesis of Optically Active SiO-containing Polymers," Macromolecules, 2005, pp. 6902-6908, vol. 38, No. 16, American Chemical Society, United States of America.

Xue, L. et al., "Precise Synthesis of Poly(silphenylenesiloxane)s with Epoxy Side Functional Groups by Tris (pentalfluorophenyl)borane as a Catalyst," Polymer Journal, Mar. 5, 2007, pp. 379-388, vol. 39, No. 4, The Society of Polymer Science, Japan.

* cited by examiner (a)

(b)

(a)

(b)

(a)

(b)

(a)

(b)

METHOD FOR PRODUCING SURFACE-MODIFIED BASE MATERIAL, METHOD FOR PRODUCING JOINED BODY, NEW HYDROSILANE COMPOUND, SURFACE TREATMENT AGENT, SURFACE TREATMENT AGENT KIT, AND SURFACE-MODIFIED BASE MATERIAL

TECHNICAL FIELD

The present invention relates to a method for producing a base material surface-modified with a molecular structure (surface-modified base material), a method for producing a joined body including a plurality of base materials joined together, and new hydrosilane compounds usable for these production methods. The present invention more particularly relates to a method for producing a surface-modified base material and a method for producing a joined body that use no catalyst (activator) containing any metal element. The present invention further relates to a surface treatment agent and a surface treatment agent kit that can be used to carry out these production methods and also relates to a surface-modified base material.

BACKGROUND ART

Modification of the surface of a base material with a particular molecular structure allows impartation of various properties to the base material or improvement of the properties of the base material. The impartation and improvement of properties are based on the interaction that the molecular structure introduced by modification has with other substances and, in some cases, on the form of the base material. Examples of the properties include separation medium property and adsorption property.

There are many known materials that have a surface over which hydrophilic groups are distributed. For example, glass, ceramic, and oxides such as silica and alumina generally have a surface covered by hydrophilic groups such as hydroxy groups. Thus, modification of the surface of a base material composed of such a substance can be accomplished by introducing a molecular structure using as a foothold the hydrophilic groups present on the surface. For surface modification of such a base material, a silicon compound may be used. It is common to use a halosilane such as chlorosilane or an alkoxysilane as the silicon compound. The silicon compound may be a so-called silane coupling agent having two or more different functional groups per molecule.

Meanwhile, Patent Literature 1 describes a process for coating a metal surface, the process including applying a reagent containing a reactive group selected from Si—H, Sn—H, and Ge—H in the presence of a platinum-group metal as a compound or in metallic form.

CITATION LIST

Patent Literature

Patent Literature 1: JP 2002-507146 A

SUMMARY OF INVENTION

Technical Problem

Halosilanes are highly reactive and suitable for surface modification by vapor-phase reactions. However, halosilanes are unsuitable for surface modification by liquid-phase reactions and, for example, are not capable of modifying the internal surface of a porous body. By contrast, alkoxysilanes are less reactive than halosilanes and are applicable to liquid-phase reactions. However, alkoxysilanes undergo hydrolysis by water in air or in a solution to cause a sol-gel reaction to gradually progress and therefore are difficult to separate and purify. This poses an obstacle to industrial production of surface-modified base materials. The sol-gel reaction also tends to result in the formation of a multimolecular layer structure, and the formation of the structure hinders further modification of the base material surface. This is likely to cause many unreacted hydroxy groups to remain on the base material surface and makes uniform modification difficult. Additionally, the use of an alkoxysilane has the following problems: a high-temperature, long-time treatment is required (a typical example is modification under toluene reflux at 110° C. for several hours); the reaction is reversible, and an eliminated alcohol is adsorbed and remains on the surface of the base material, so the base material has limited application; and a strong nucleophile such as a Grignard reagent cannot be used for synthesis of the alkoxysilane, so the library synthesis of the alkoxysilane is limited.

Aside from the above, methods using an allylsilane as a silicon compound have been proposed (see JP 2004-175793 A, for example). Allylsilanes are suitable for surface modification by liquid-phase reactions and, unlike alkoxysilanes, are easy to separate and purify. However, a high-temperature, long-time treatment is still required (JP 2004-175793 A employs modification under toluene reflux at 110° C. for more than 10 hours).

An object of the present invention is to provide a method for producing a surface-modified base material that is capable of surface-modifying a base material at a lower temperature in a shorter time than conventional methods and that allows a wide variety of options for, e.g., the form, type, and application of the base material, the mode of modification reaction, and the type of the molecular structure with which the base material is surface-modified.

Another object of the present invention is to provide a method for producing a joined body, to which the above method for producing a surface-modified base material is applied. The method for producing a joined body is capable of treatment at a lower temperature in a shorter time than conventional methods and allows a wide variety of options for, e.g., the type and application of base materials.

Solution to Problem

A method for producing a surface-modified base material according to the present disclosure includes a step of bringing a base material having a polar group present on a surface thereof into contact with a hydrosilane compound having a molecular structure A and having a Si—H group composed of a silicon atom of the molecular structure A and a hydrogen atom bonded to the silicon atom in the presence of a borane catalyst so as to allow a dehydrocondensation reaction to take place between the base material and the compound, thereby forming the base material surface-modified with the molecular structure A.

A method for producing a joined body according to the present disclosure includes a step of bringing a plurality of base materials each having a polar group present on a surface thereof into contact with a hydrosilane compound having a molecular structure A and having two or more Si—H groups each composed of a silicon atom of the molecular structure A and a hydrogen atom bonded to the silicon atom in the presence of a borane catalyst so as to allow a dehydrocondensation reaction to take place between the base materials and the compound, thereby obtaining a joined body including the plurality of base materials joined together via the molecular structure A acting as a junction structure.

A hydrosilane compound according to the present disclosure includes a new hydrosilane compound. The new hydrosilane compound is 1-(dimethylsilyl)pyrene, (dimethylsilyl)ferrocene, 1-(3-dimethylsilylpropyl)naphthalene, (3-azidopropyl)dimethylsilane, [3-(dimethylsilyl)propyl] acrylamide, 1-(3-dimethylsilylpropyl)-3-methylimidazolium iodide, (3-nitropropyl)dimethylsilane, 4-(dimethylsilyl)butyric acid, ethyl 4-(dimethylsilyl)butyrate, [3-(dimethylsilyl)propyl] diethylphosphate, 4-(dimethylsilyl) butanol, (3-benzoylpropyl)dimethylsilane, 5,6-epoxyhexyldimethylsilane, (3-dimethylsilylpropyl) trifluoroacetamide, phthaloylpolymethylhydrosiloxane, chloropropylpolymethylhydrosiloxane, 3-aminopropylpolymethylhydrosiloxane, 3-acetoxypropylpolymethylhydrosiloxane, 3-chloropropyl-isopropoxypolymethylhydrosiloxane, 3-azidopropylpolymethylhydrosiloxane, 3-bromopropylpolymethylhydrosiloxane, dodecylpolymethylhydrosiloxane, octadecylpolymethylhydrosiloxane, perfluorohexylethylpolymethylhydrosiloxane, polyallylmethylhydrosiloxane, polyepoxymethylhydrosiloxane, poly(chloroisopropoxy)methylhydrosiloxane, poly(epoxy)methylhydrosiloxane, 1H,1H,2H,2H-nonafluorohexylsiloxypolymethylhydrosiloxane, 3,6-dithia-1,8-octanedioxypolymethylhydrosiloxane, N-dimethylhydrosilylpropyliminotriphenylphosphorane, N-methyldihydrosilylpropyliminotriphenylphosphorane, 4-dimethylsilylphenylmagnesium bromide, 4-(1,3-dithian-2-yl)dimethylsilylbenzene, or triethyl-3-(dimethylsilylpropyl)ammonium bromide.

A treatment agent according to the present disclosure is a surface treatment agent for modifying a surface of a base material and includes: a hydrosilane compound having a molecular structure A and having a Si—H group composed of a silicon atom of the molecular structure A and a hydrogen atom bonded to the silicon atom; and a borane catalyst.

A treatment agent kit according to the present disclosure is a surface treatment agent kit for modifying a surface of a base material and includes: a component A containing a hydrosilane compound having a molecular structure A and having a Si—H group composed of a silicon atom of the molecular structure A and a hydrogen atom bonded to the silicon atom; and a component B containing a borane catalyst.

A surface-modified base material according to the present disclosure is a surface-modified base material obtained by the method for producing a surface-modified base material according to the present disclosure, the surface-modified base material including a base material surface-modified with the molecular structure A.

Advantageous Effects of Invention

The present disclosure makes it possible to achieve a method for producing a surface-modified base material that is capable of surface-modifying a base material at a lower temperature in a shorter time than conventional methods and that allows a wide variety of options for the form, type, and application of the base material, the mode of the modification reaction, and the type of the molecular structure with which the base material is surface-modified.

The present disclosure also makes it possible to achieve a method for producing a joined body that is capable of treatment at a lower temperature in a shorter time than conventional methods and allows a wide variety of options for the type and application of base materials.

DESCRIPTION OF EMBODIMENTS

Figure 1:
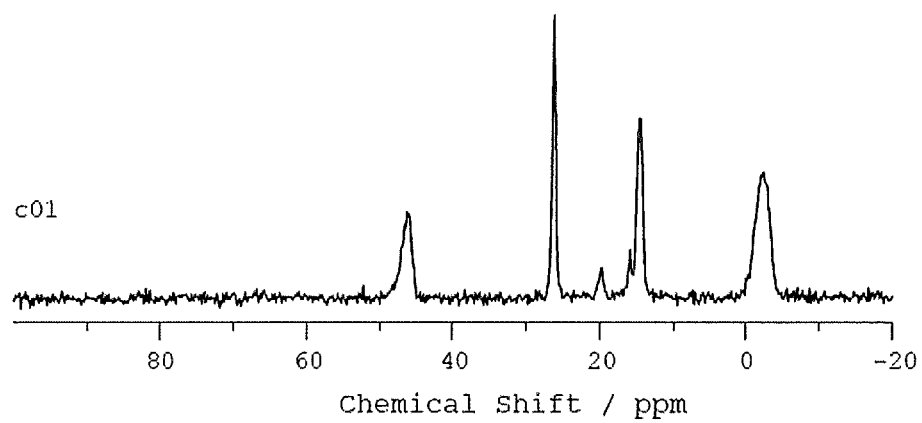
FIG. 1 shows a $^{13}$C-nuclear magnetic resonance (NMR) profile of (3-chloropropyl)dimethylsilane prepared in Production Example 4.

A first aspect of the present disclosure provides a method for producing a surface-modified base material, including a step of bringing a base material having a polar group present on a surface thereof into contact with a hydrosilane compound having a molecular structure A and having a Si—H group composed of a silicon atom of the molecular structure A and a hydrogen atom bonded to the silicon atom in the presence of a borane catalyst so as to allow a dehydrocondensation reaction to take place between the base material and the compound, thereby forming the base material surface-modified with the molecular structure A.

A second aspect of the present disclosure provides the method for producing a surface-modified base material as set forth in the first aspect, wherein the polar group is a hydroxy group and/or a carbonyl group.

A third aspect of the present disclosure provides the method for producing a surface-modified base material as set forth in the first aspect, wherein the polar group is a hydroxy group.

A fourth aspect of the present disclosure provides the method for producing a surface-modified base material as set forth in any one of the first to third aspects, wherein the catalyst is tris(pentafluorophenyl)borane.

A fifth aspect of the present disclosure provides the method for producing a surface-modified base material as set forth in any one of the first to fourth aspects, wherein the base material is composed of a non-metal substance.

A sixth aspect of the present disclosure provides the method for producing a surface-modified base material as set forth in any one of the first to fifth aspects, wherein the base material is a flake, a particle, or a fiber.

A seventh aspect of the present disclosure provides the method for producing a surface-modified base material as set forth in any one of the first to sixth aspects, wherein the step is carried out at a temperature lower than 50° C.

An eighth aspect of the present disclosure provides a method for producing a joined body, including a step of bringing a plurality of base materials each having a polar group present on a surface thereof into contact with a hydrosilane compound having a molecular structure A and having two or more Si—H groups each composed of a silicon atom of the molecular structure A and a hydrogen atom bonded to the silicon atom in the presence of a borane catalyst so as to allow a dehydrocondensation reaction to take place between the base materials and the compound, thereby obtaining a joined body including the plurality of base materials joined together via the molecular structure A acting as a junction structure.

A ninth aspect of the present disclosure provides the method for producing a joined body as set forth in the eighth aspect, wherein the polar group is a hydroxy group and/or a carbonyl group.

A tenth aspect of the present disclosure provides the method for producing a joined body as set forth in the eighth or ninth aspect, wherein the base materials are each independently a flake, a particle, or a fiber.

An eleventh aspect of the present disclosure provides a new hydrosilane compound selected from the following compounds.

1-(dimethylsilyl)pyrene, (dimethylsilyl)ferrocene, 1-(3-dimethylsilylpropyl)naphthalene, (3-azidopropyl)dimethylsilane, [3-(dimethylsilyl)propyl]acrylamide, 1-(3-dimethylsilylpropyl)-3-methylimidazolium iodide, (3-nitropropyl)dimethylsilane, 4-(dimethylsilyl)butyric acid, ethyl 4-(dimethylsilyl)butyrate, [3-(dimethylsilyl)propyl] diethylphosphate, 4-(dimethylsilyl)butanol, (3-benzoylpropyl)dimethylsilane, 5,6-epoxyhexyldimethylsilane, (3-dimethylsilylpropyl)trifluoroacetamide, phthaloylpolymethylhydrosiloxane, chloropropylpolymethylhydrosiloxane, 3-aminopropylpolymethylhydrosiloxane, 3-acetoxypropylpolymethylhydrosiloxane, 3-chloropropylisopropoxypolymethylhydrosiloxane, 3-azidopropylpolymethylhydrosiloxane, 3-bromopropylpolymethylhydrosiloxane, dodecylpolymethylhydrosiloxane, octadecylpolymethylhydrosiloxane, perfluorohexylethylpolymethylhydrosiloxane, polyallylmethylhydrosiloxane, polyepoxymethylhydrosiloxane, poly(chloroisopropoxy)methylhydrosiloxane, poly(epoxy)methylhydrosiloxane, 1H,1H,2H,2H-nonafluorohexylsiloxypolymethylhydrosiloxane, 3,6-dithia-1,8-octanedioxypolymethylhydrosiloxane, N-dimethylhydrosilylpropyliminotriphenylphosphorane, N-methyldihydrosilylpropyliminotriphenylphosphorane, 4-dimethylsilylphenylmagnesium bromide, 4-(1,3-dithian-2-yl)dimethylsilylbenzene, and triethyl-3-(dimethylsilylpropyl)ammonium bromide.

A twelfth aspect of the present disclosure provides a surface treatment agent for modifying a surface of a base material, the surface treatment agent including: a hydrosilane compound having a molecular structure A and having a Si—H group composed of a silicon atom of the molecular structure A and a hydrogen atom bonded to the silicon atom; and a borane catalyst.

A thirteenth aspect of the present disclosure provides a surface treatment agent kit for modifying a surface of a base material, the surface treatment agent kit including: a component A containing a hydrosilane compound having a molecular structure A and having a Si—H group composed of a silicon atom of the molecular structure A and a hydrogen atom bonded to the silicon atom; and a component B containing a borane catalyst.

A fourteenth aspect of the present disclosure provides a surface-modified base material obtained by the method for producing a surface-modified base material as provided by any one of the first to seventh aspects, the surface-modified base material including a base material surface-modified with the molecular structure A.

A fifteenth aspect of the present disclosure provides the surface-modified base material as set forth in the fourteenth aspect, wherein the base material is cellulose nanofiber, pulp powder, or metal oxide powder.

A sixteenth aspect of the present disclosure provides the surface-modified base material as set forth in the fourteenth or fifteenth aspect, wherein the hydrosilane compound is a new hydrosilane compound selected from the following compounds.

1-(dimethylsilyl)pyrene, (dimethylsilyl)ferrocene, 1-(3-dimethylsilylpropyl)naphthalene, (3-azidopropyl)dimethylsilane, [3-(dimethylsilyl)propyl]acrylamide, 1-(3-dimethylsilylpropyl)-3-methylimidazolium iodide, (3-nitropropyl)dimethylsilane, 4-(dimethylsilyl)butyric acid, ethyl 4-(dimethylsilyl)butyrate, [3-(dimethylsilyl)propyl]diethylphosphate, 4-(dimethylsilyl)butanol, (3-benzoylpropyl)dimethylsilane, 5,6-epoxyhexyldimethylsilane, (3-dimethylsilylpropyl)trifluoroacetamide, phthaloylpolymethylhydrosiloxane, chloropropylpolymethylhydrosiloxane, 3-aminopropylpolymethylhydrosiloxane, 3-acetoxypropylpolymethylhydrosiloxane, 3-chloropropylisopropoxypolymethylhydrosiloxane, 3-azidopropylpolymethylhydrosiloxane, 3-bromopropylpolymethylhydrosiloxane, dodecylpolymethylhydrosiloxane, octadecylpolymethylhydrosiloxane, perfluorohexylethylpolymethylhydrosiloxane, polyallylmethylhydrosiloxane, polyepoxymethylhydrosiloxane, poly(chloroisopropoxy)methylhydrosiloxane, poly(epoxy)methylhydrosiloxane, 1H,1H,2H,2H-nonafluorohexylsiloxypolymethylhydrosiloxane, 3,6-dithia-1,8-octanedioxypolymethylhydrosiloxane, N-dimethylhydrosilylpropyliminotriphenylphosphorane, N-methyldihydrosilylpropyliminotriphenylphosphorane, 4-dimethylsilylphenylmagnesium bromide, 4-(1,3-dithian-2-yl)dimethylsilylbenzene, and triethyl-3-(dimethylsilylpropyl)ammonium bromide.

[Method for Producing Surface-Modified Base Material]

A method for producing a surface-modified base material according to the present disclosure includes a step (I) of bringing a base material having a polar group present on a surface thereof into contact with a hydrosilane compound having a molecular structure A and having a Si—H group composed of a silicon atom of the molecular structure A and a hydrogen atom bonded to the silicon atom in the presence of a borane catalyst so as to allow a dehydrocondensation reaction to take place between the base material and the hydrosilane compound, thereby forming the base material surface-modified with the molecular structure A. This production method is a method for producing a base material (surface-modified base material) surface-modified with the molecular structure A containing a silicon atom. In this method, a hydrosilane compound having a Si—H group composed of a silicon atom of the molecular structure A and a hydrogen atom bonded to the silicon atom and a base material having a polar group on a surface thereof are brought into contact in the presence of a borane catalyst to allow a dehydrocondensation reaction to take place between the base material and the hydrosilane compound and thereby produce the surface-modified base material.

In the step (I), a hydrosilane compound and a particular catalyst are used for surface modification of a base material having a polar group present on a surface thereof. The surface modification of the base material in the step (I) is progressed at a low temperature in a short time. Thus, with the production method according to the present disclosure, the base material can be surface-modified at a lower temperature in a shorter time than with conventional methods. The polar group is, for example, at least one selected from a hydroxy group, a carbonyl group, a cyano group, an imino group, and an epoxy group. Preferred is a hydroxy group and/or a carbonyl group.

The hydrosilane compound is not influenced by hydrolysis in air or in a solution as observed for alkoxysilanes. The hydrosilane compound is thus easy to separate and purify, so the production method according to the present disclosure is fully applicable to industrial implementation. In addition, a sol-gel reaction between molecules of the hydrosilane compound does not readily take place, and the formation of a multimolecular layer structure can thus be prevented. That is, the surface of the base material can be modified more uniformly and, for example, the formation of a monomolecular-modifying layer is possible.

The surface modification of the base material in the step (I) is progressed at a low temperature in a short time; however, the hydrosilane compound itself exhibits a lower reactivity with the polar group such as a hydroxy or carbonyl group than halosilanes. This is why the production method according to the present disclosure allows a wide variety of options for the mode of the modification reaction and, for example, the step (I) may be performed as a vapor-phase reaction or as a liquid-phase reaction, and modification of the internal surface of a porous body is possible. The hydrosilane compound reacts with the polar group such as a hydroxy or carbonyl group sufficiently quickly as compared to allylsilane compounds, so any undesired side reaction can be prevented. This also contributes to the wide variety of options for the mode of surface modification in the production method according to the present disclosure.

The hydrosilane compound can be synthesized using a strong nucleophile such as a Grignard reagent. The library synthesis is thus possible, so the production method according to the present disclosure allows a wide variety of options for the type of the molecular structure A with which the base material is surface-modified.

In the step (I), the features (form, type, application, etc.) of the base material are not limited as long as a polar group such as a hydroxy or carbonyl group is present on the surface of the base material. The surface modification of the base material in the step (I) can be progressed at a low temperature in a short time. The production method according to the present disclosure thus allows a wide variety of options for the features of the base material and is capable of, for example, modifying the surface of a resin having a low glass transition temperature (Tg).

In the step (I), a dehydrocondensation reaction takes place; that is, hydrogen gas is evolved as the surface modification of the base material proceeds. The production method according to the present disclosure thus allows a wider variety of options for application of the base material than methods using any alkoxysilane in the case of which it is difficult to prevent adsorption of an alcohol on the surface of the base material. When a liquid-phase reaction is employed, completion of the surface modification of the base material can be visually confirmed by cessation of the evolution of hydrogen gas.

The step (I) employs the use of a borane catalyst, a compound of boron which is a non-metal element, rather than the use of a catalyst (activator) containing a metal element. The step (I) can increase the amount of the molecular structure A introduced (supported) onto the surface of the base material, as compared to the case of using a catalyst (activator) containing a metal element such as a platinum-group element. The step (I) can also eliminate an adverse effect on the properties of the base material or the surface of the base material which would be caused by a metal element remaining on the surface of the base material after modification.

(Hydrosilane Compound)

The hydrosilane compound is a compound having a molecular structure A and having a Si—H group composed of a silicon atom of the molecular structure A and a hydrogen atom bonded to the silicon atom. The hydrosilane compound has a hydrosilyl group in the molecule. The molecular structure A is a structure corresponding to a moiety of the hydrosilane compound other than the hydrogen atom which is eliminated in the reaction described above. The hydrosilane compound preferably has the Si—H group in the framework (main chain) of the molecule and more preferably has the Si—H group at a terminal of the molecule (has a Si—H group composed of a terminal silicon atom of the molecular structure A and a hydrogen atom bonded to the silicon atom). When the hydrosilane compound has the Si—H group at a terminal of the molecular structure A, the hydrosilane compound may have the Si—H group at only one terminal or at both terminals of the molecular structure A. The hydrosilane compound that has the two or more Si—H groups, such as that which has the Si—H groups at both terminals, can be used for purposes other than surface modification of the base material and can be used, for example, for production of a joined body which will be described later. The number of hydrogen atoms bonded to one silicon atom is typically, but not limited to, one.

At least one of the bonds of the silicon atom of the Si—H group is a bond to a hydrogen atom, and at least another of the bonds of the silicon atom of the Si—H group is a bond to an atom of the molecular structure A other than the hydrogen atom, such as a constituent atom of the framework of the molecular structure A. The atom or group with which the silicon atom forms the other bonds is not limited to a particular one. In terms of the stability of the hydrosilane compound and the reactivity with a polar group such as a hydroxy or carbonyl group, an alkyl group having 1 to 4 carbon atoms is preferred, and a methyl group is particularly preferred. At least one of the other bonds may be a bond to the alkyl group or all of the other bonds may each be a bond to the alkyl group. The hydrosilane compound may have a structure in which all of the other bonds are those to methyl groups. More specifically, the hydrosilane compound may have, for example, a dimethylsilyl group ($-SiH(CH_3)_2$).

In the step (I), the molecular structure A of the hydrosilane compound binds to and modifies the surface of the base material through the reaction described above. That is, the moiety of the hydrosilane compound other than the hydrogen atom eliminated by the dehydrocondensation reaction binds to the surface of the base material.

The molecular structure A of the hydrosilane compound can have any functional group other than the Si—H group as long as the step (I) can be carried out. The functional group is, for example, a polymerizable group. Specific examples, not limited to polymerizable groups, include a vinyl group, an allyl group, an alkyl group, an aralkyl group, an ester group, an amide group, an amino group, a carboxyl group, a cyano group, a nitro group, an azido group, an alkoxy group, a phosphono group, a sulfo group, an aldehyde group, a carbonyl group, a sulfhydryl group, a carbamate group, and a hydroxy group. When the molecular structure A has such a functional group, a property derived from the functional group can be imparted to the surface-modified base material obtained by the production method according to the present disclosure or the surface of this surface-modified base material.

The method for forming the hydrosilane compound is not limited, and a possible example is synthesis using a strong nucleophile such as a Grignard reagent. In other words, the Si—H group of the hydrosilane compound can be maintained even in the presence of a Grignard reagent. Thus, the library synthesis of the hydrosilane compound is possible, and the range of options for the type of the molecular structure A with which the base material is surface-modified can be broad. An example of the hydrosilane compound is a compound formed from a molecule A having an amino group (—$NH_2$), a hydroxy group (—OH), a sulfhydryl group (—SH), or a $MgX^1$ group at its terminal and $SiHR^1R^2X^2$ through a reaction between this terminal group and $SiHR^1R^2X^2$. Here, $R^1$ and $R^2$ are each independently a hydrogen atom or an alkyl group having 1 to 8 carbon atoms and may each be, for example, a methyl group, and $X^1$ and $X^2$ are each a halogen atom. In this reaction, $SiHR^1R^2X^2$ acts as an electrophile and reacts with the molecule A to form a C—N bond, a C—O bond, a C—S bond, or a C—C bond between the molecule A and $SiHR^1R^2X^2$ so that the hydrosilane compound is produced. Another example of the hydrosilane compound is a compound formed from a molecule B having an electron-withdrawing group at its terminal and $SiHR^1R^2$—$R^3MgX^3$ through a reaction between this terminal group and $SiHR^1R^2$—$R^3MgX^3$. Here, $R^1$ and $R^2$ are each independently a hydrogen atom or an alkyl group having 1 to 8 carbon atoms and may each be, for example, a methyl group, $R^3$ is an organic group, and $X^1$ and $X^2$ are each a halogen atom. In this reaction, $SiHR^1R^2$—$R^3MgX^3$ acts as a nucleophile and reacts with the molecule B. Examples of the molecule A include a broad range of substances, including: biologically relevant substances such as amino acids, peptides, proteins, enzymes, and glucosamines; medicinal chemicals such as antibiotic substances and synthetic antibacterial agents; hole-transporting compounds typified by carbazole; ionic liquids such as imidazolium salts; sugars; alcohols; and phenols. Examples of the molecule B similarly include a broad range of substances. Thus, the production method according to the present disclosure permits a huge number of compounds to be used as the hydrosilane compound and allows a wide variety of options for the type of the molecular structure A with which the base material is surface-modified.

Specific examples of the hydrosilane compound include 1-(dimethylsilyl)naphthalene, 1-(dimethylsilyl)pyrene, (dimethylsilyl)ferrocene, (3-chloropropyl)dimethylsilane, (3-bromopropyl)dimethylsilane, 1-(3-dimethylsilylpropyl)naphthalene, (3-azidopropyl)dimethylsilane, (3-aminopropyl)dimethylsilane, [3-(dimethylsilyl)propyl]acrylamide, 1-(3-dimethylsilylpropyl)-3-methylimidazolium iodide, N-[3-(dimethylsilyl)propyl]phthalimide, (3-nitropropyl)dimethylsilane, 4-(dimethylsilyl)butyric acid, ethyl 4-(dimethylsilyl)butyrate, [3-(dimethylsilyl)propyl]diethylphosphate, 3-mercaptopropyldimethylsilane, 4-(dimethylsilyl)butanol, (3-benzoylpropyl)dimethylsilane, polymethylhydrosiloxane (PMHS), 5,6-epoxyhexyldimethylsilane, (3-dimethylsilylpropyl)trifluoroacetamide, phthaloylpolymethylhydrosiloxane, chloropropylpolymethylhydrosiloxane, 3-aminopropylpolymethylhydrosiloxane, 3-acetoxypropylpolymethylhydrosiloxane, 3-chloropropylisopropoxypolymethylhydrosiloxane, 3-azidopropylpolymethylhydrosiloxane, 3-bromopropylpolymethylhydrosiloxane, dodecylpolymethylhydrosiloxane, octadecylpolymethylhydrosiloxane, perfluorohexylethylpolymethylhydrosiloxane, polyallylmethylhydrosiloxane, polyepoxymethylhydrosiloxane, poly(chloroisopropoxy)methylhydrosiloxane, poly(epoxy)methylhydrosiloxane, 1H,1H,2H,2H-nonafluorohexylsiloxypolymethylhydrosiloxane, 3,6-dithia-1,8-octanedioxypolymethylhydrosiloxane, N-dimethylhydrosilylpropyliminotriphenylphosphorane, N-methyldihydrosilylpropyliminotriphenylphosphorane, 4-dimethylsilylphenylmagnesium bromide, 4-(1,3-dithian-2-yl)dimethylsilylbenzene, triethyl-3-(dimethylsilylpropyl) ammonium bromide, 3-isocyanatopropyldimethylsilane, and 3-isocyanatopropylpolymethylhydrosiloxane. Among these, PMHS is a hydrosilane compound having a large number of Si—H groups in the molecule. PMHS is a compound produced as an industrial by-product and is commercially-available at low cost.

Unlike alkoxysilanes and halosilanes, hydrosilane compounds can be separated and purified by a common purification technique such as silica gel column chromatography and are capable of long-term storage for years. In other words, the hydrosilane compound used in the step (I) is a compound that can maintain its molecular structure even under conditions which generally cause hydrolysis of silicon compounds. This provides many industrial merits such as the following: the production method according to the present disclosure is applicable to industrial production of surface-modified base materials; surface modification is possible with a reduced amount of impurities; and the compound prepared need not be used up at one time.

(Catalyst)

The catalyst used in the step (I) is a borane catalyst. The borane catalyst is not particularly limited and is, for example, at least one selected from trichloroborane, tribromoborane, trifluoroborane, and tris(pentafluorophenyl)borane $((C_6F)_3B)$. $(C_6F)_3B$ is preferred because its use permits the surface modification of the base material to be completed at a low temperature in a short time and provides high efficiency of the modification.

(Base Material)

The base material is not particularly limited as long as the above-mentioned polar group such as a hydroxy or carbonyl group is present on the surface of the base material. When, for example, the hydroxy group and the carbonyl group are compared, the hydroxy group more readily reacts with the Si—H group of the hydrosilane compound. This is why the surface modification of the base material in the step (I) can be carried out at a lower temperature in a shorter time when the base material has a hydroxy group present on a surface thereof.

The base material having a hydroxy group present on a surface thereof is, for example, a base material composed of at least one substance selected from a metal oxide, a silica, a glass, a ceramic, and a hydroxy group-containing resin. It suffices for the base material to have a hydroxy group present on at least a part of its surface, and the base material may be, for example, one that has a surface at least a part of which is composed of the at least one substance. Examples of such a base material include a metallic base material having an oxidized surface and a metallic base material having an oxidized film placed on a surface thereof. Examples of the metal oxide include $TiO_2$, $ZrO_2$, $Al_2O_3$, $In_2O_3$, $CeO_2$, ZnO, $SnO_2$, ITO (indium-tin oxide), and $GeO_2$. Examples of the silica include a silicon wafer optionally having an oxidized film placed on a surface thereof. Examples of the ceramic include rock, stone, and sand. Examples of the hydroxy group-containing resin include cellulose, cellulose ester, and polyvinyl alcohol (PVA).

The base material may be any of the following: wood; non-wood, vegetable materials such as kenaf, natural polymers such as cotton, peptide, protein, sugar, and leather; synthetic polymers such as vinylon and PVA; talc; mica; and apatite.

Examples of a base material having a carbonyl group present on a surface thereof include polyester resins such as polyethylene terephthalate.

Examples of a base material having another polar group on a surface thereof include graphene, carbon nanotube, and polyimide.

In the production method according to the present disclosure, the base material can be composed of a non-metal substance as described above.

The polar group may be, for example, a group formed by surface treatment (e.g., plasma treatment, corona treatment, or light-irradiation treatment) of the base material. In this case, the polar group may not be present on the surface of the base material that has yet to surface-treated. When the base material is a polymer, the polar group may be a group derived from a residue of a compound (e.g., a polymerization initiator) used for synthesis of the polymer.

The form of the base material is not particularly limited, and the base material may be a flat sheet, a bulk, a porous body, a flake, a particle, or a fiber. With the production method according to the present disclosure, a surface-modified base material in the form of a flake, a particle, or a fiber can be produced using a base material in the form of a flake, a particle, or a fiber. The base material may be a monolithic porous body having a hierarchical porous structure composed of macropores and mesopores such as monolithic porous bodies disclosed in JP 06(1994)-265534 A, JP 07(1995)-41374 A, and WO 2007/021037 A1. As proposed by IUPAC, the term "macropore" is used to refer to a pore having a diameter (pore size) of 50 nm or more, while the term "mesopore" is used to refer to a pore intermediate between a macropore and a micropore (a pore having a diameter of less than 2 nm), i.e., a pore having a diameter of 2 nm or more and less than 50 nm.

The size of the base material is not limited either. When the base material is a fiber, the fiber may be a microfiber with a diameter of about 1 to 1000 μm or a nanofiber with a diameter of less than 1 μm. An example of such a fiber is cellulose nanofiber (microfibrillated cellulose).

The base material may a biological part. An example of such a base material is a tooth. The outermost surface of a tooth is protected by enamel the main component of which is hydroxyapatite. The production method according to the present disclosure is capable of modifying the outermost surface. This modification can, for example, prevent the attachment of *Streptococcus mutans* to the tooth surface. Other examples of such a base material include a hair and a nail.

(Carrying Out of Step (I))

The specific method for carrying out the step (I) is not limited. It suffices that the hydrosilane compound and the surface of the base material to be surface-modified be brought into contact in the presence of the catalyst. Examples of available methods include: a method in which the base material is immersed in a solution containing the hydrosilane compound and the catalyst; and a method in which the surface of the base material to be surface-modified is coated or sprayed with the hydrosilane compound and the catalyst. The hydrosilane compound and the catalyst may be brought into contact with the surface of the base material to be surface-modified together or individually in any order.

The step (I) may be performed as a vapor-phase reaction or as a liquid-phase reaction and is preferably performed as a liquid-phase reaction. When the step (I) is performed as a liquid-phase reaction, the variety of options for the form, type, and application of the base material to be modified is further increased.

In an example where the step (I) is carried out as a liquid-phase reaction, a solution containing the hydrosilane compound and the catalyst may be used. The concentration of the hydrosilane compound in the solution is, for example, 0.05 to 0.20 mol/L and is preferably 0.15 to 0.17 mol/L. The concentration of the catalyst in the solution is, for example, 0.0010 to 0.010 mol/L and is preferably 0.0017 to 0.0040 mol/L. The solvent in the solution is not particularly limited as long as the solvent does not hinder the step (I). Examples of the solvent include: alkanes such as hexane, octane, decane, and dodecane; cycloalkanes such as cyclohexane; halogen solvents such as dichloromethane and dichloroethane; aromatic hydrocarbons such as toluene, xylene, and benzene; alkyl or aryl ether solvents such as diethyl ether, tetrahydrofuran (THF), dioxane, cyclopentyl methyl ether, and diphenyl ether; non-protic polar solvents such as N,N-dimethylformamide (DMF), dimethyl sulfoxide (DMSO), and acetonitrile; mineral oils; linear or cyclic silicone oils; and mixed solvents containing two or more of these solvents. Preferred are dichloromethane, toluene, diethyl ether, THF, and DMF in terms of reduced adverse effect on the base material and the surface of the base material and in terms of safety of the step. The solvent in the solution can be selected depending on the type of the hydrosilane compound. For example, there is a case where cyclohexane is more suitable than hexane. For example, a linear or cyclic silicone oil may be selected with a focus on the solubility of polymethylhydrosiloxane (PMHS) or modified PMHS which is a type of hydrosilane compound. Taking into account industrial implementation of the production method, for example, alkanes that have a relatively high flash point such as octane, decane, and dodecane are easy to use and, alternatively, a mineral oil or a linear or cyclic silicone oil may be selected. Depending on its type, the silicone oil can maintain its volatility and thus can contribute to facilitating the post-treatment subsequent to the step (I). The same solvent as used in pre-treatment such as shaping, shape changing, cutting, or crushing of the base material may be selected. In this case, the step (I) can be carried out subsequent to the pre-treatment of the base material. The solution can contain any substance other than the hydrosilane compound and/or catalyst as long as the substance does not hinder the step (I).

When the step (I) is carried out as a liquid-phase reaction, a medium that is a solid (including a gel) at a storage temperature such as ordinary temperature and that converts to a liquid at a desired temperature for allowing the reaction to take place may be used instead of the solvent described above. The use of such a medium makes it possible, during storage, to inhibit the reaction of the hydrosilane compound in which the catalyst participates while maintaining the activity of the hydrosilane compound and catalyst, and also makes it possible to allow the liquid-phase reaction to take place at the desired reaction temperature. For example, a solid including the above medium containing the hydrosilane compound and the catalyst may be placed on a surface of a base material, such as a glass, which is vertically positioned, and the solid may then be heated to convert the medium to a liquid so that the modification takes place directly on the surface. Such a medium is, for example, paraffin. Depending on the type of paraffin used, the surface modification of the base material is possible at a temperature lower than 50° C. as will be described later. The solvent described above can be added to the medium where necessary.

The surface modification of the base material in the step (I) can be carried out at a lower temperature in a shorter time than that in conventional methods. The conditions for carrying out the step (I) are not particularly limited. For example, the temperature required to carry out the step (I) is lower than 50° C. (which means that the step (I) can be progressed at a temperature lower than 50° C.), and can be 40° C. or lower, 30° C. or lower, or even room temperature (25° C.). The time required to carry out the step (I) is, for example, 5 hours or less, and can be 3 hours or less, even 1 hour or less, 30 minutes or less, 10 minutes or less, or 5 minutes or less. Such a low temperature and a short time to carry out the step (I) contribute to the wide variety of options for the features of the base material and, for example, make it possible to use a resin material having a low Tg as the base material.

[Method for Producing Joined Body]

The method for producing a surface-modified base material according to the present disclosure has various applications. For example, a joined body including a plurality of base materials joined together can be produced as follows: a hydrosilane compound having a molecular structure A and having two or more Si—H groups each composed of a silicon atom of the molecular structure A and a hydrogen atom bonded to the silicon atom is used to allow the two or more Si—H groups to undergo a dehydrocondensation reaction with the surfaces of the base materials, thereby forming a unified body including the plurality of base materials joined together via the molecular structure A acting as a junction structure having junction points corresponding to reaction sites of the dehydrocondensation reaction. That is, the method for producing a joined body according to the present disclosure includes a step (II) of bringing a plurality of base materials each having a polar group such as a hydroxy or carbonyl group present on a surface thereof into contact with a hydrosilane compound having a molecular structure A and having two or more Si—H groups each composed of a silicon atom of the molecular structure A and a hydrogen atom bonded to the silicon atom in the presence of a borane catalyst so as to allow a dehydrocondensation reaction to take place between the base materials and the compound, thereby obtaining a joined body including the plurality of base materials joined together via the molecular structure A acting as a junction structure. This method for producing a joined body has the same benefits as the method for producing a surface-modified base material according to the present disclosure and, for example, allows a wide variety of options for the type, application, etc. of the base materials.

Examples of the hydrosilane compound include PMHS, polyphenylmethylsiloxane, polyethylhydrosiloxane, polyphenyl(dimethylhydrosiloxane)siloxane, polyoctylmethylsiloxane, and modified PMHS (e.g., modified PMHS as prepared in Production Examples and Examples described later), and preferred are PMHS and modified PMHS. These compounds have a large number of Si—H groups per molecule, and the Si—H groups serve as points of junction with the surfaces of the base materials in the dehydrocondensation reaction. This increases the joining strength of the joined body.

It suffices for the catalyst to meet the same requirements as that used in the step (I).

The form of the base materials is not limited, and each base material may be a flat sheet, a bulk, a porous body, a flake, a particle, or a fiber. The production method according to the present disclosure makes it possible to use base materials in the form of a flake, a particle, or a fiber to form a joined body (integrated body) constituted by these base materials.

The specific method for carrying out the step (II) is not limited, and the step (II) can be carried out in the same manner as the step (I), except that the hydrosilane compound must be a compound having two or more Si—H groups.

[Surface-Modified Base Material]

The surface-modified base material according to the present disclosure is a surface-modified base material obtained by the production method according to the present disclosure, the surface-modified base material including a base material surface-modified with the molecular structure A.

The surface-modified base material obtained by the production method according to the present disclosure can have various properties (including the properties of the surface and the properties as the entire base material) depending on the features of the base material to be surface-modified, the type of the molecular structure A, and the degree of surface modification (the amount of the molecular structure A supported on the surface). Examples of the properties include hydrophobicity, water repellency, superhydrophobicity, superhydrophilicity, heat resistance, flame retardancy, non-flammability, chemical reactivity (including reactivity in biological reaction using an enzyme or the like), polymerizability, polymerization initiating ability (in the case where the molecular structure A has properties as a polymerization initiator, for example), photoreactivity, photoresponsivity, substance separation-purification property, adsorptivity, electrochemical property, electrical conductivity, ion conductivity, compatibility, bonding ability, and heat conductivity. The surface-modified base material can thus be used in various applications. Examples of the applications include a water-repellent material, a superhydrophobic material, a superhydrophilic material, a heat-resistant material, flame-retardant material, a non-flammable material, a sealing material, a photoresponsive funtional material, a separation or purification medium such as a separation or purification column, an adsorptive material, an electrochemically active material, a photopatterning material, a transparent conductive film material, a proton conductive membrane, a bioreactor (enzyme-supported), a PMHS composite, an organic catalyst, a metal catalyst, a molecular recognition material (sugar, peptide, or cellulose composite), an additive for resins (which may be, for example, a strength improver or a heat-resistance improver that makes use of impartation of compatibility with a resin to the surface of the base material; in this case, the base material can be silica, pulp, kenaf, or persimmon tannin), a bonding material, and a heat-conductive material. Reduced occurrence of side reactions in the step (I) also contributes to the wide variations of application.

In the production method according to the present disclosure, the form and size of the base material are not limited, as described above for the method for producing a surface-modified base material. Thus, the form and size of the surface-modified base material obtained by the production method according to the present disclosure are not limited either, and the base material can be, for example, cellulose nanofiber, pulp powder, or metal oxide powder. The molecular structure A can be a molecular structure derived from any of the following new hydrosilane compounds: 1-(dimethylsilyl)pyrene, (dimethylsilyl)ferrocene, 1-(3-dimethylsilylpropyl)naphthalene, (3-azidopropyl)dimethylsilane, [3-(dimethylsilyl)propyl]acrylamide, 1-(3-dimethylsilylpropyl)-3-methylimidazolium iodide, (3-nitropropyl)dimethylsilane, 4-(dimethylsilyl)butyric acid, ethyl 4-(dimethylsilyl)butyrate, [3-(dimethylsilyl)propyl] diethylphosphate, 4-(dimethylsilyl)butanol, (3-benzoylpropyl)dimethylsilane, 5,6-epoxyhexyldimethylsilane, (3-dimethylsilylpropyl)trifluoroacetamide, phthaloylpolymethylhydrosiloxane, chloropropylpolymethylhydrosiloxane, 3-aminopropylpolymethylhydrosiloxane, 3-acetoxypropylpolymethylhydrosiloxane, 3-chloropropyl-isopropoxypolymethylhydrosiloxane, 3-azidopropylpolymethylhydrosiloxane, 3-bromopropylpolymethylhydrosiloxane, dodecylpolymethylhydrosiloxane, octadecylpolymethylhydrosiloxane, perfluorohexylethylpolymethylhydrosiloxane, polyallylmethylhydrosiloxane, polyepoxymethylhydrosiloxane, poly(chloroisopropoxy)methylhydrosiloxane, poly(epoxy)methylhydrosiloxane, 1H,1H,2H,2H-nonafluorohexylsiloxypolymethylhydrosiloxane, 3,6-dithia-1,8-octanedioxypolymethylhydrosiloxane, N-dimethylhydrosilylpropyliminotriphenylphosphorane, N-methyldihydrosilylpropyliminotriphenylphosphorane, 4-dimethylsilylphenylmagnesium bromide, 4-(1,3-dithian-2-yl)dimethylsilylbenzene, and triethyl-3-(dimethylsilylpropyl)ammonium bromide.

[Joined Body]

A joined body obtained by the production method according to the present disclosure can have various properties depending on the features of the base materials and the type and content of the molecular structure A. Examples of the properties are as mentioned above for the surface-modified base material. The applications based on the properties are not particularly limited either, and examples of the applications are also as mentioned above for the surface-modified base material.

[Surface Treatment Agent]

The method for producing a surface-modified base material and the method for producing a joined body, and hence the surface modification of a base material and the junction between base materials, which have been described above, can be carried out, for example, using a surface treatment agent according to the present disclosure. The surface treatment agent according to the present disclosure is a surface treatment agent for modifying the surface of a base material and includes: a hydrosilane compound having a molecular structure A and having a Si—H group composed of a silicon atom of the molecular structure A and a hydrogen atom bonded to the silicon atom; and a borane catalyst. For the surface treatment agent according to the present disclosure, it is preferable that the hydrosilane compound and the borane catalyst be contained in a medium that is a solid (including a gel) at a storage temperature of the treatment agent and that converts to a liquid at a desired temperature for allowing the reaction to take place. It should be understood, from the above descriptions of the method for producing a surface-modified base material and the method for producing a joined body, that the use of the surface treatment agent enables the surface modification of a base material and the junction between base materials.

When used for junction between base materials, the treatment agent according to the present disclosure acts also as a joining agent (joining treatment agent).

The specific method for modifying the surface of a base material with the treatment agent according to the present disclosure is not limited. For example, the treatment agent may be placed on the surface of the base material and optionally be heated. The placement can be done using a technique such as coating or spraying. The placement of the treatment agent and the optional heating cause a dehydrocondensation reaction to take place between the base material and the hydrosilane compound on the surface of the base material so that the surface is modified with the molecular structure A (which means that a base material surface-modified with the molecular structure A is formed).

The specific method for joining base materials with the treatment agent according to the present disclosure is not limited. For example, it suffices to create a situation where the treatment agent is placed on the interface (junction plane) between the base materials. In this case, heating may optionally be carried out.

The concentration of the hydrosilane compound in the treatment agent according to the present disclosure is, for example, 0.05 to 0.20 mol/L and preferably 0.15 to 0.17 mol/L. The concentration of the borane catalyst in the treatment agent according to the present disclosure is, for example, 0.0010 to 0.010 mol/L and preferably 0.0017 to 0.0040 mol/L.

Even when the treatment agent according to the present disclosure contains no liquid-repellent agent such as a water-repellent or oil-repellent agent, appropriate selection of the type of the hydrosilane compound makes it possible to carry out liquid-repellency treatment as the surface treatment.

The base material is not limited, provided that a polar group such as a hydroxy or carbonyl group is present on the surface to be treated (surface to be modified or to be joined). The treatment agent according to the present disclosure is less subject to limitations imposed by the form of the base material and is capable of treating a base material that is in the form of, for example, a flake, a particle, or a fiber.

The treatment agent according to the present disclosure may include a substance other than the hydrosilane compound and the borane catalyst where necessary.

The treatment agent according to the present disclosure can be commercially distributed, for example, in the form of being packed in a container. In this case, the container is not limited and any container is selectable, provided that the container has no polar group such as a hydroxy or carbonyl group on the surface thereof with which the treatment agent can come into contact.

[Surface Treatment Agent Kit]

The method for producing a surface-modified base material and the method for producing a joined body, and hence the surface modification of a base material and the junction between base materials, which have been described above, can be carried out, for example, using a surface treatment agent kit according to the present disclosure. The treatment agent kit according to the present disclosure is a treatment agent kit for modifying the surface of a base material and includes: a component A containing a hydrosilane compound having a molecular structure A and having a Si—H group composed of a silicon atom of the molecular structure A and a hydrogen atom bonded to the silicon atom; and a component B containing a borane catalyst. It should be understood, from the above descriptions of the method for producing a surface-modified base material and the method for producing a joined body, that the use of the treatment agent kit enables the surface modification of a base material and the junction between base materials.

When used for junction between base materials, the kit according to the present disclosure acts also as a joining agent kit (joining treatment agent kit).

The specific method for modifying the surface of a base material with the treatment agent kit according to the present disclosure is not limited. For example, the component A and the component B may be placed on the surface of the base material together or individually. The placement can be done using a technique such as coating or spraying. The placement of the component A and the component B causes a dehydrocondensation reaction to take place between the base material and the hydrosilane compound on the surface of the base material so that the surface is modified with the molecular structure A (which means that a base material surface-modified with the molecular structure A is formed).

The specific method for joining base materials with the treatment agent kit according to the present disclosure is not limited. It suffices to create a situation where the component A and the component B are placed on the interface (junction plane) between the base materials. Examples of the method available for this purpose in the case of junction between two base materials include: a method in which the component A and the component B are placed on a surface (surface to be joined) of one base material and then a surface (surface to be joined) of the other base material is brought into contact with the surface to be joined of the one base material; a method in which the component A is placed on a surface to be joined of one base material while the component B is placed on a surface to be joined of the other base material, and then the surfaces to be joined of the two base materials are brought into contact with each other; and a method in which the surfaces to be joined of the two base materials are brought into contact with each other and then the component A and the component B are placed between the surfaces to be joined.

The component A contains a hydrosilane compound having a molecular structure A. The hydrosilane compound is as described above. For joining base materials together (for carrying out the method for producing a joined body), a hydrosilane compound having two or more Si—H groups each composed of a silicon atom of the molecular structure A and a hydrogen atom bonded to the silicon atom is used. The component A may contain an optional material other than the hydrosilane compound. The optional material is, for example, a solvent. When the component A contains the optional material, the content of the hydrosilane compound in the component A is, for example, 0.5 to 80 weight % and preferably 5 to 10 weight %. The solvent is, for example, a solvent as described above, and specific examples include dichloromethane, dichloroethane, chloroform, pentane, hexane, cyclohexane, octane, decane, dodecane, paraffin, and mineral oil. When the reaction to be allowed to take place is a solvent-free reaction, there is no need to use the solvent.

The component B contains a borane catalyst. The borane catalyst is as described above. The component B can contain an optional material other than the borane catalyst. The optional material is, for example, a solvent. When the component B contains the optional material, the content of the borane catalyst in the component B is, for example, 0.5 to 80 weight % and preferably 5 to 10 weight %. The solvent is, for example, a solvent as described above, and specific examples include dichloromethane, dichloroethane, chloroform, pentane, hexane, cyclohexane, octane, decane, dodecane, paraffin, and mineral oil. When the reaction to be allowed to take place is a solvent-free reaction, there is no need to use the solvent.

Even when the treatment liquid kit (the component A and/or the component B) according to the present disclosure contains no liquid-repellent agent such as a water-repellent or oil-repellent agent, appropriate selection of the type of the hydrosilane compound makes it possible to carry out liquid-repellency treatment as the surface treatment.

The base material is not limited, provided that a polar group such as a hydroxy or carbonyl group is present on the surface to be treated (surface to be modified or to be joined). The treatment agent kit according to the present disclosure is less subject to limitations imposed by the form of the base material and is capable of treating a base material that is in the form of, for example, a flake, a particle, or a fiber.

The treatment agent kit according to the present disclosure may be composed of the component A, the component B, and another optional component where necessary.

The component A and the component B can be commercially distributed, for examples, in the form of being packed in containers. In this case, the containers are not limited and any containers are selectable, provided that the containers have no polar group such as a hydroxy or carbonyl group on the surfaces thereof with which the component A or the component B can come into contact.

EXAMPLES

Hereinafter, the present invention will be described in more detail by way of examples. The present invention is not limited to the examples given below.

Preparation of Hydrosilane Compounds

Production Example 1

Synthesis of 1-(dimethylsilyl)naphthalene

A hexane solution of n-butyllithium (nBuLi) (6.25 mL, containing 10 mmol of nBuLi) was added dropwise slowly to a diethyl ether ($Et_2O$) solution (40 mL) of 1-iodonaphthalene (2541 mg, 10 mmol) under nitrogen atmosphere at −5° C., followed by stirring for 15 minutes. Subsequently, chlorodimethylsilane (1135 mg, 12 mmol) was added, followed by stirring at room temperature for 2 hours, after which liquid-liquid separation was performed using an aqueous HCl solution (with a concentration of 10 weight %) and distilled water. The aqueous layer was extracted with $Et_2O$, and $Na_2SO_4$ was then added to the remaining organic layer, followed by filtration and concentration. Next, the resulting mixture was purified by column chromatography (developing solvent: hexane) to obtain 1769 mg (9.5 mmol) of 1-(dimethylsilyl)naphthalene (1) in a yield of 95%. The reaction formula for the reaction is shown below.

[Chemical Formula 1]

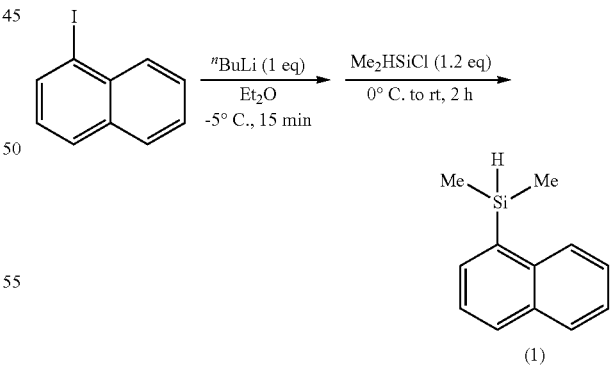

The 1-(dimethylsilyl)naphthalene obtained was identified by $^1$H-NMR measurement. $CDCl_3$ was used as the deuterated solvent for the $^1$H-NMR measurement (this is the same for Production Examples which will be subsequently described). The chemical shifts determined were as follows.

δ (ppm): 8.11-8.13 (d, J=8.4 Hz, 1H), 7.86-7.90 (m, 2H), 7.72-7.74 (d, J=6.6 Hz, 1H), 7.45-7.56 (m, 3H), 4.84-4.90 (m, 1H), 0.50-0.51 (d, J=3.6 Hz, 6H)

Production Example 2

Synthesis of 1-(dimethylsilyl)pyrene

A hexane solution of nBuLi (1.88 mL, containing 3 mmol of nBuLi) was added dropwise slowly to a Et$_2$O (25 mL)/THF (5 mL) solution of 1-bromopyrene (843 mg, 3 mmol) under nitrogen atmosphere at −5° C., followed by stirring for 30 minutes. Subsequently, chlorodimethylsilane (339 mg, 3.6 mmol) was added, followed by stirring at room temperature for 2 hours, after which liquid-liquid separation was performed using an aqueous HCl solution (with a concentration of 10 weight %) and distilled water. The aqueous layer was extracted with CH$_2$Cl$_2$, and Na$_2$SO$_4$ was then added to the remaining organic layer, followed by filtration and concentration. Next, the resulting mixture was purified by column chromatography (developing solvent: hexane) to obtain 735 mg (2.82 mmol) of 1-(dimethylsilyl)pyrene (2) in a yield of 94%. The reaction formula for the reaction is shown below.

[Chemical Formula 2]

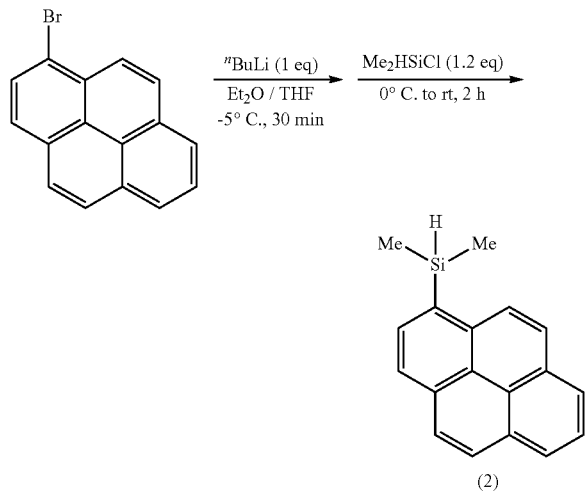

(2)

The 1-(dimethylsilyl)pyrene obtained was identified by $^1$H-NMR measurement. The chemical shifts determined were as follows.

δ (ppm): 8.38-8.40 (d, J=9.2 Hz, 1H), 8.17-8.22 (t, J=7.6 Hz, 3H), 8.12-8.17 (t, J=9.2 Hz, 2H), 8.03-8.10 (dd, J=6.0, 9.2 Hz, 2H), 7.99-8.03 (t, J=7.6 Hz, 1H), 5.05-5.11 (m, 1H), 0.60-0.61 (d, J=4.0 Hz, 6H)

Production Example 3

Synthesis of (dimethylsilyl)ferrocene

A THF solution of ferrocene (1860 mg, 10 mmol) and potassium-t-butoxide (tBuOK, 168 mg, 1.5 mmol) was stirred under nitrogen atmosphere at −78° C. for 15 minutes. Subsequently, a hexane solution of t-butyllithium (tBuLi) (12.5 mL, containing 20 mmol of tBuLi) was added dropwise slowly under nitrogen atmosphere at −70° C., followed by stirring for 90 minutes. Next, chlorodimethylsilane (2838 mg, 30 mmol) was added, and the resulting mixture was taken out of a cooling chamber and then stirred at room temperature for 2 hours. Next, Et$_2$O was added to the reaction mixture, which was then subjected to liquid-liquid separation using an aqueous HCl solution (with a concentration of 10 weight %) and distilled water. The aqueous layer was extracted with Et$_2$O, and Na$_2$SO$_4$ was then added to the remaining organic layer, followed by filtration and concentration. The resulting mixture was purified by distillation to obtain 1806 mg (7.4 mmol) of (dimethylsilyl)ferrocene (3) in a yield of 74%. The reaction formula for the reaction is shown below.

[Chemical Formula 3]

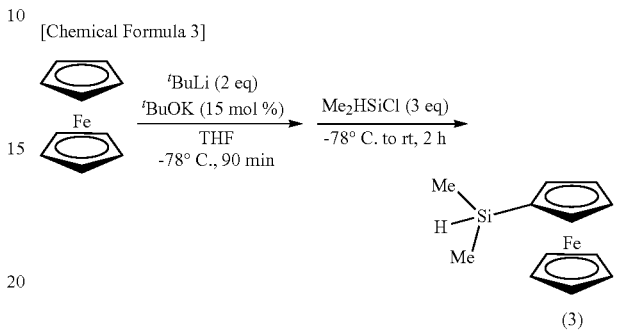

(3)

The (dimethylsilyl)ferrocene obtained was identified by $^1$H-NMR measurement. The chemical shifts determined were as follows.

δ (ppm): 4.38-4.44 (m, 1H), 4.35-4.36 (t, J=1.6 Hz, 2H), 4.14 (s, 7H), 0.30-0.31 (d, J=3.6 Hz, 6H)

Production Example 4

Synthesis of (3-chloropropyl)dimethylsilane

Chlorodimethylsilane (5.18 mL, 46 mmol) was added to a mixture of chloro(1,5-cyclooctadiene)iridium dimer ([IrCl(cod)]2, 2.6 mg, containing 0.003 mmol of Ir), allyl chloride (3.25 mL, 40 mmol), and 1,5-cyclooctadiene (10 μL, 0.08 mmol), followed by stirring at 40° C. for 6 hours. Subsequently, the resulting mixture was distilled under reduced pressure to obtain chloro(3-chloropropyl)dimethylsilane (6293 mg, 36.8 mmol) in a yield of 92%.

Next, the obtained chloro(3-chloropropyl)dimethylsilane (6293 mg, 36.8 mmol) was added slowly to a solution of lithium aluminum hydride (LiAH$_4$, 1398 mg, 36.8 mmol) in Et$_2$O (40 mL) under nitrogen atmosphere at 0° C., followed by stirring at room temperature for 2 hours. Next, the resulting mixture was ice-cooled, and Na$_2$SO$_4$·10H$_2$O was added slowly, followed by stirring. The resulting mixture was subjected to Celite filtration, followed by washing with CH$_2$Cl$_2$ and then by distillation under reduced pressure to obtain 4477 mg (32.8 mmol) of (3-chloropropyl)dimethylsilane (4) in a yield of 82% from the allyl chloride. The reaction formula for the reaction is shown below.

[Chemical Formula 4]

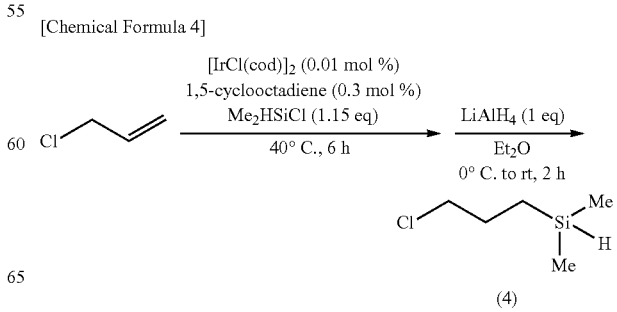

(4)

The (3-chloropropyl)dimethylsilane obtained was identified by 1H-NMR measurement. The chemical shifts determined were as follows.

δ (ppm): 3.85-3.90 (m, 1H), 3.50-3.54 (t, J=7.2 Hz, 2H), 1.78-1.85 (m, 2H), 0.68-0.73 (m, 2H), 0.09-0.10 (d, J=4.0 Hz, 6H)

Figure 2:
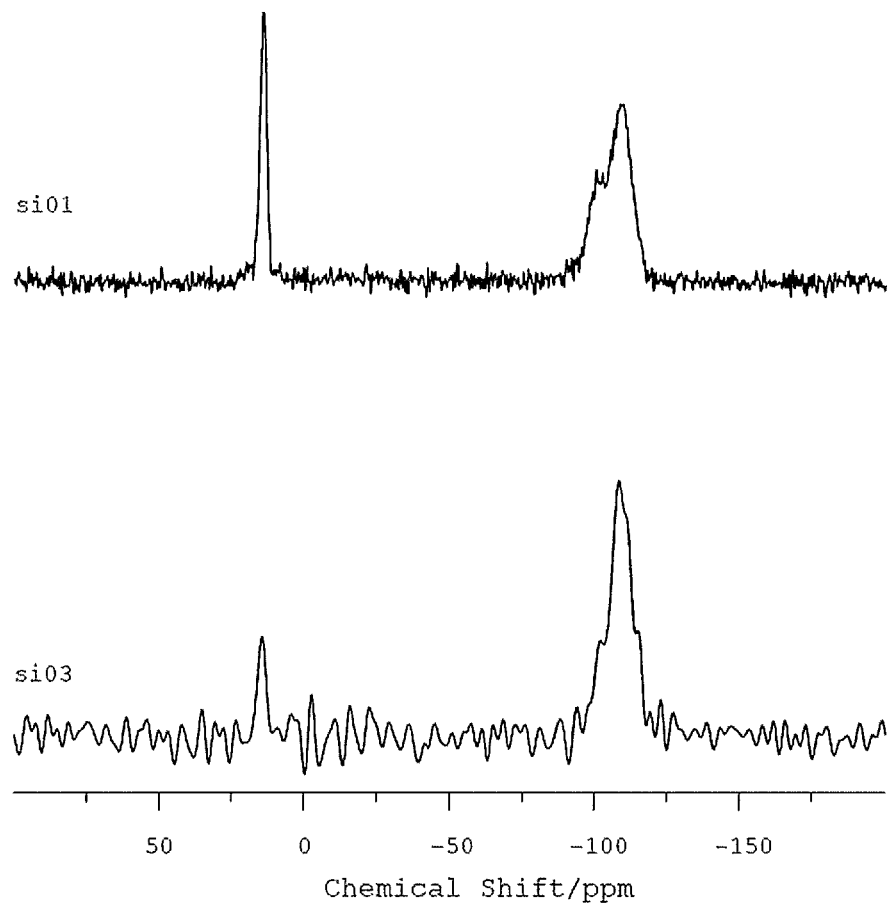
FIG. 2 is a $^{29}$Si-NMR profile of (3-chloropropyl)dimethylsilane prepared in Production Example 4.
Figures 3, 4:
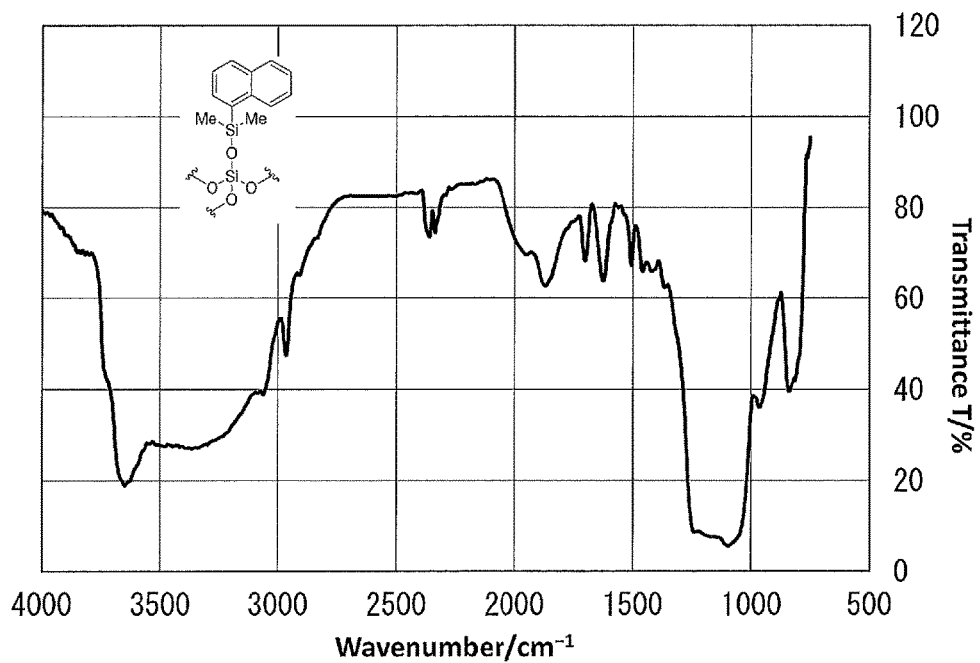
FIG. 3 shows an infrared spectroscopy (IR) spectrum of a surface-modified silica gel fabricated in Example 1-1.
FIG. 4 shows an IR spectrum of a surface-modified silica gel fabricated in Example 1-2.
Figure 5:
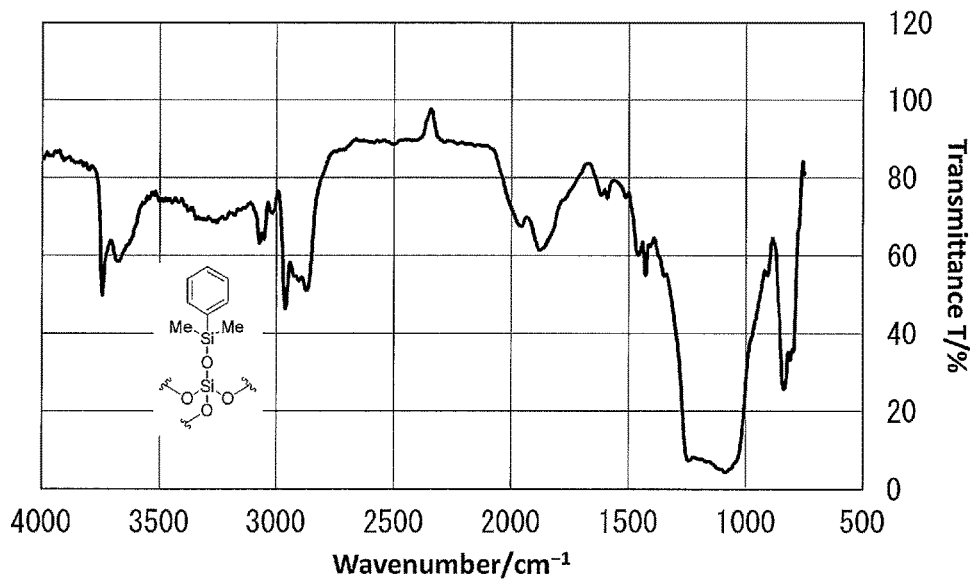
FIG. 5 shows an IR spectrum of a surface-modified silica gel fabricated in Example 1-3.
Figure 6:
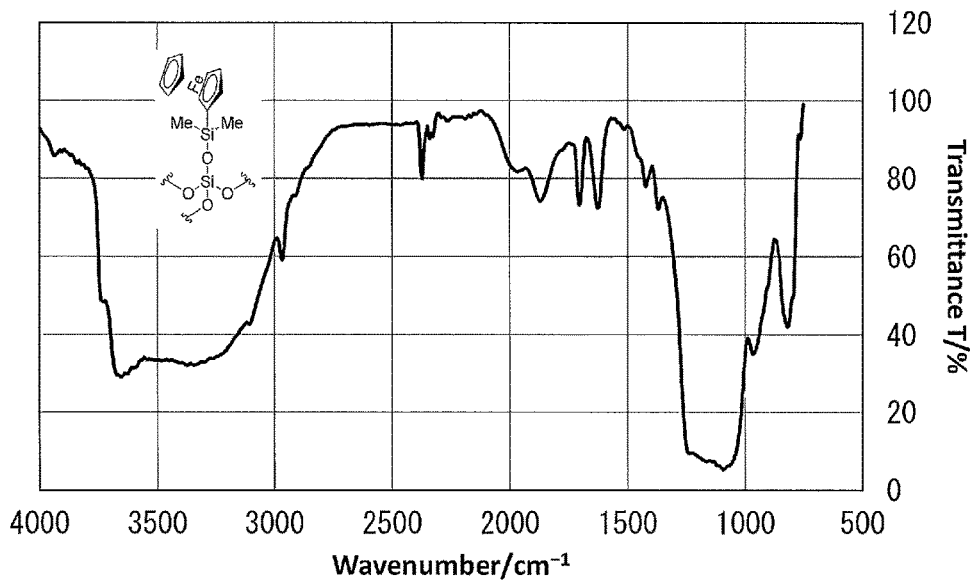
FIG. 6 shows an IR spectrum of a surface-modified silica gel fabricated in Example 1-4.
Figure 7:
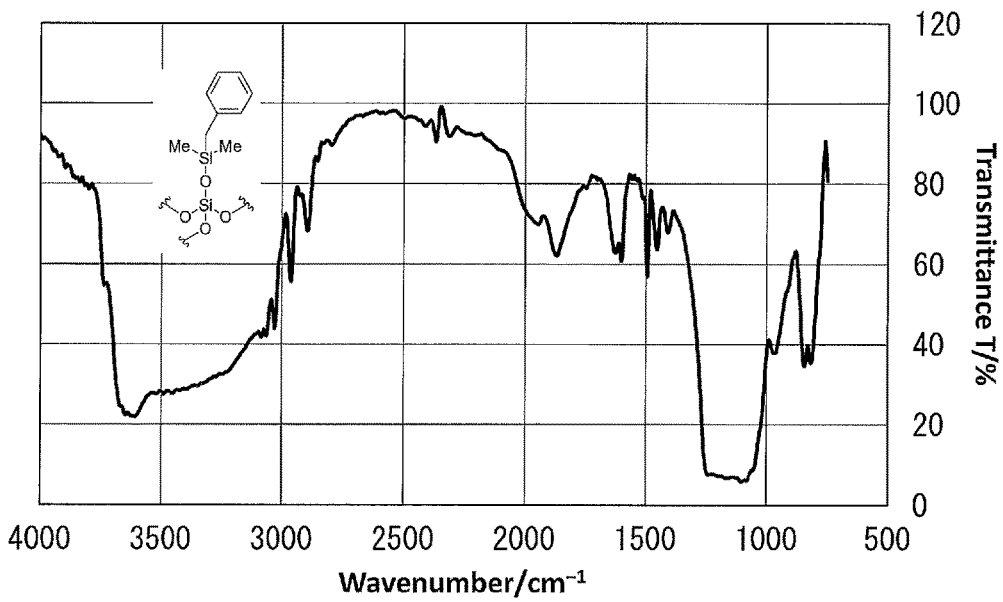
FIG. 7 shows an IR spectrum of a surface-modified silica gel fabricated in Example 1-5.

Identification of the (3-chloropropyl)dimethylsilane obtained was performed also by $^{13}$C-NMR and $^{29}$Si-NMR. The profiles obtained by $^{13}$C-NMR and $^{29}$Si-NMR are shown in FIGS. 1 and 2, respectively.

Production Example 5

Synthesis of (3-bromopropyl)dimethylsilane

Chlorodimethylsilane (5.18 mL, 46 mmol) was added to a mixture of [IrCl(cod)]2 (2.6 mg, containing 0.003 mmol of Ir), allyl bromide (3.49 mL, 40 mmol), and 1,5-cyclooctadiene (10 μL, 0.08 mmol), followed by stirring at 40° C. for 17 hours. Subsequently, the resulting mixture was distilled under reduced pressure to obtain chloro(3-bromopropyl)dimethylsilane (6443 mg, 35.6 mmol) in a yield of 89%.

Next, the obtained chloro(3-bromopropyl)dimethylsilane (6443 mg, 35.6 mmol) was added slowly to a solution of LiAlH$_4$ (1352 mg, 35.6 mmol) in Et$_2$O (40 mL) under nitrogen atmosphere at 0° C., followed by stirring at room temperature for 2 hours. Next, the resulting mixture was ice-cooled, and Na$_2$SO$_4$ 10H$_2$O was added slowly, followed by stirring. The resulting mixture was subjected to Celite filtration, followed by washing with CH$_2$Cl$_2$ and then by distillation under reduced pressure to obtain 6082 mg (33.6 mmol) of (3-bromopropyl)dimethylsilane (5) in a yield of 84% from the allyl bromide. The reaction formula for the reaction is shown below.

[Chemical Formula 5]

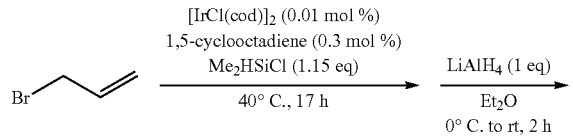

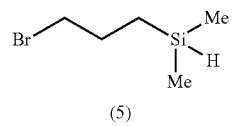

(5)

The (3-bromopropyl)dimethylsilane obtained was identified by $^1$H-NMR measurement. The chemical shifts determined were as follows.

δ (ppm): 3.85-3.90 (m, 1H), 3.39-3.43 (t, J=6.8 Hz, 2H), 1.86-1.93 (m, 2H), 0.68-0.73 (m, 2H), 0.09-0.10 (d, J=3.6 Hz, 6H)

Production Example 6

Synthesis of 1-(3-dimethylsilylpropyl)naphthalene 1-allylnaphthalene (1682 mg, 10 mmol) and chlorodimethylsilane (1.54 mL, 11.5 mmol) were added to a mixture of [IrCl(cod)]2 (0.6 mg, containing 0.8 μmol of Ir) and 1,5-cyclooctadiene (2.5 μL, 0.02 mmol), followed by stirring at 40° C. for 12 hours.

Subsequently, the resulting mixture was ice-cooled, and Et$_2$O (30 mL) was added to the cooled mixture, to which triethylamine (Et$_3$N, 2038 mg, 20 mmol) and isopropyl alcohol (iPrOH, 900 mg, 15 mmol) were further added dropwise individually, followed by stirring at room temperature for 30 minutes. Next, the resulting crude product was subjected to Celite filtration, followed by concentration under reduced pressure. The concentrate was then subjected to short-path column chromatography (developing solvent: hexane/Et$_2$O=20/1 (volume ratio)) to concentrate the solvent, and thus 1-[(3-dimethylisopropoxysilyl)propyl]naphthalene (2345 mg, 8.2 mmol) was obtained.

Next, the obtained 1-[(3-dimethylisopropoxysilyl)propyl]naphthalene (2345 mg, 8.2 mmol) was added slowly to a THF solution (20 mL) of LiAlH$_4$ (312 mg, 8.2 mmol) under nitrogen atmosphere at 0° C., followed by stirring at 60° C. for 2 hours. Subsequently, the resulting mixture was ice-cooled, and Na$_2$SO$_4$. 10H$_2$O was added slowly, followed by stirring. The resulting mixture was subjected to Celite filtration, followed by washing with CH$_2$Cl$_2$, then by concentration under reduced pressure, and then by purification by column chromatography (developing solvent: hexane) to obtain 1622 mg (7.1 mmol) of 1-(3-dimethylsilylpropyl)naphthalene (6) in a yield of 71%. The reaction formula for the reaction is shown below.

[Chemical Formula 6]

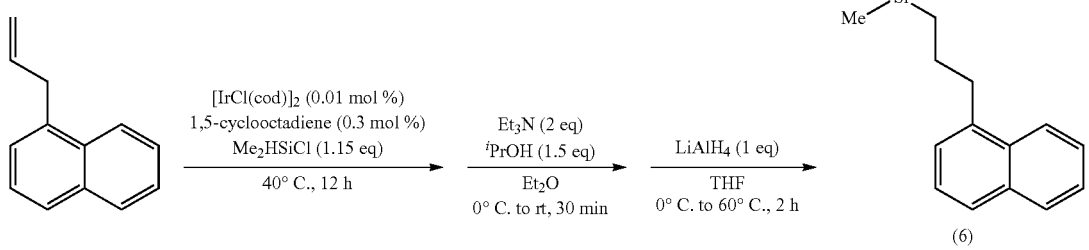

(6)

The 1-(3-dimethylsilylpropyl)naphthalene obtained was identified by $^1$H-NMR measurement. The chemical shifts determined were as follows.

δ (ppm): 8.04-8.06 (d, J=8.4 Hz, 1H), 7.85-7.87 (d, J=6.8 Hz, 1H), 7.71-7.73 (d, J=8.0 Hz, 1H), 7.45-7.53 (m, 2H), 7.39-7.42 (t, J=7.6 Hz, 1H), 7.32-7.34 (d, J=6.8 Hz, 1H), 3.86-3.91 (m, 1H), 3.09-3.13 (t, J=7.6 Hz, 2H), 1.78-1.86 (m, 2H), 0.73-0.77 (m, 2H), 0.07-0.08 (d, J=3.6 Hz, 6H)

Production Example 7

Synthesis of (3-azidopropyl)dimethylsilane (3-bromopropyl)dimethylsilane (2172 mg, 12 mmol) as prepared in Production Example 5 was added to a dimethylformamide (DMF) solution (24 mL) of sodium azide (NaN$_3$, 1170 mg, 18.0 mmol) under nitrogen atmosphere, followed by stirring at 60° C. for 12 hours. Next, the reaction mixture was cooled to room temperature, and distilled water was added to the cooled mixture, which was subjected to liquid-liquid separation using pentane. The aqueous layer was extracted with pentane, and the pentane layer collected was washed with brine (saturated aqueous NaCl solution). The washed pentane layer was dried over Na$_2$SO$_4$ and filtered, followed by concentration under reduced pressure to obtain 1681 mg (11.7 mmol) of (3-azidopropyl)dimethylsilane (7) in a yield of 98%. The reaction formula for the reaction is shown below.

[Chemical Formula 7]

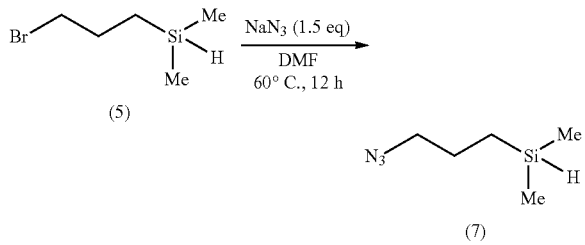

The (3-azidopropyl)dimethylsilane obtained was identified by $^1$H-NMR measurement. The chemical shifts determined were as follows.

δ (ppm): 3.85-3.90 (m, 1H), 3.24-3.28 (t, J=6.8 Hz, 2H), 1.61-1.69 (m, 2H), 0.62-0.67 (m, 2H), 0.09-0.10 (d, J=3.6 Hz, 6H)

Production Example 8

Synthesis of (3-aminopropyl)dimethylsilane (3-aminopropyl)dimethylsilane represented by the formula (8) shown below was obtained by a method according to M. X. Dung et al., "InP Quantum Dot-Organosilicon Nanocomposites", Bulletin of Korean Chemical Society, vol. 33 (2012), No. 5, pp. 1491-1504.

[Chemical Formula 8]

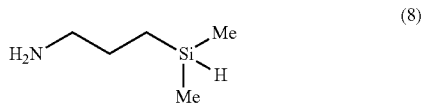

Production Example 9

Synthesis of [3-(dimethylsilyl)propyl]acrylamide

A CH$_2$Cl$_2$ solution (4 mL) of (3-aminopropyl)dimethylsilane (585 mg, 5.0 mmol) as prepared in Production Example 8 and triethylamine (531 mg, 5.25 mmol) was cooled to 0° C. under nitrogen atmosphere. A CH$_2$Cl$_2$ solution (20 mL) of acryloyl chloride (475 mg, 5.25 mmol) was added dropwise slowly, then the resulting mixture was taken out of a cooling chamber and stirred at room temperature for 12 hours. Distilled water was added to the resulting reaction mixture, the aqueous layer was extracted with CH$_2$Cl$_2$, and the organic layer collected was dried over Na$_2$SO$_4$. Next, the organic layer was filtered, followed by concentration under reduced pressure to quantitatively obtain 795 mg (5 mmol) of [3-(dimethylsilyl)propyl]acrylamide (9). The reaction formula for the reaction is shown below.

[Chemical Formula 9]

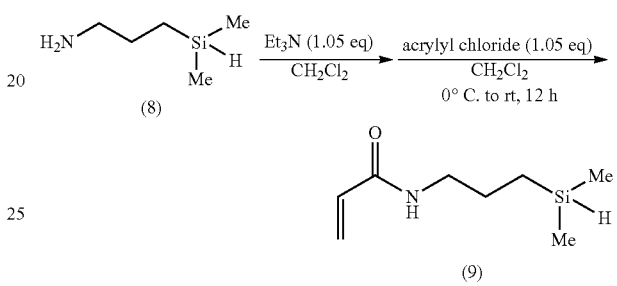

The [3-(dimethylsilyl)propyl]acrylamide obtained was identified by $^1$H-NMR measurement. The chemical shifts determined were as follows.

δ (ppm): 6.26-6.30 (dd, J=2.0, 16.8 Hz, 1H), 6.05-6.12 (m, 1H), 5.66 (bs, 1H), 5.62-5.65 (dd, J=1.2, 10 Hz, 1H), 3.84-3.89 (m, 1H), 3.31-3.36 (q, J=7.2 Hz, 2H), 1.55-1.62 (m, 2H), 0.58-0.63 (m, 2H), 0.07-0.08 (d, J=4.0 Hz, 6H)

Production Example 10

Preparation of 1-(3-dimethylsilylpropyl)imidazole

Imidazole (408 mg, 6.0 mmol) was added little by little to a DMF suspension (24 mL) of sodium hydride (NaH, 144 mg, 6.0 mmol) under nitrogen atmosphere at 0° C., followed by stirring for 45 minutes. Next, 3-(bromopropyl)dimethylsilane (905 mg, 5.0 mmol) as prepared in Production Example 5 was added, followed by stirring at room temperature for 24 hours. Distilled water was then added to the resulting reaction mixture, and the aqueous layer was extracted with CH$_2$Cl$_2$. Subsequently, the organic layer was washed with brine, then dried over Na$_2$SO$_4$, and filtered, followed by concentration under reduced pressure. The resulting crude product was purified by column chromatography (developing solvent: ethyl acetate (EtOAc)/hexane=3/1 (volume ratio)) to obtain 781 mg (4.7 mmol) of 1-(3-dimethylsilylpropyl)imidazole (10) in a yield of 93%. The reaction formula for the reaction is shown below.

[Chemical Formula 10]

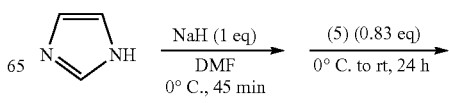

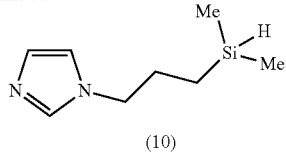

(10)

The 1-(3-dimethylsilylpropyl)imidazole obtained was identified by $^1$H-NMR measurement. The chemical shifts determined were as follows.

δ (ppm): 7.47 (s, 1H), 7.06 (s, 1H), 6.91 (a, 1H), 3.91-3.94 (t, J=7.6 Hz, 2H), 3.83-3.89 (m, 1H), 1.88 (bs, 1H), 1.77-1.85 (m, 2H), 0.52-0.57 (m, 2H), 0.07-0.08 (d, J 10=3.6 Hz, 6H)

Production Example 11

Synthesis of 1-(3-dimethylsilylpropyl)-3-methylimidazolium iodide

Methyl iodide (MeI, 426 mg, 3.0 mmol) was added to a CH$_2$Cl$_2$ solution (6 mL) of 1-(3-dimethylsilylpropyl)imidazole (504 mg, 3.0 mmol) as prepared in Production Example 10 under nitrogen atmosphere, followed by stirring at 40° C. for 24 hours. Completion of the reaction was followed by concentration under reduced pressure to quantitatively obtain 930 mg (3.0 mmol) of 1-(3-dimethylsilylpropyl)-3-methylimidazolium iodide (11). The reaction formula for the reaction is shown below.

[Chemical Formula 11]

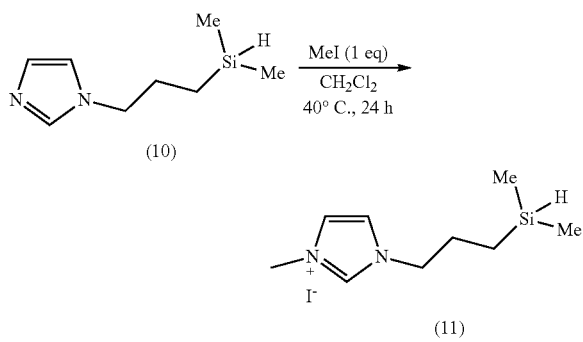

The 1-(3-dimethylsilylpropyl)-3-methylimidazolium iodide obtained was identified by $^1$H-NMR measurement. The chemical shifts determined were as follows.

δ (ppm): 10.17 (s, 1H), 7.47 (s, 1H), 7.37 (a, 1H), 4.32-4.36 (t, J=7.2 Hz, 2H), 4.14 (s, 3H), 3.83-3.89 (m, 1H), 1.92-2.00 (m, 2H), 0.60-0.65 (m, 2H), 0.10-0.11 (d, J=3.6 Hz, 6H)

Production Example 12

Synthesis of N-[3-(dimethylsilyl)propyl]phthalimide (3-bromopropyl)dimethylsilane (1267 mg, 7.0 mmol) as prepared in Production Example 5 was added to a DMF solution (14 mL) of potassium phthalimide (1556 mg, 8.4 mmol), followed by stirring at 70° C. for 15 hours. An aqueous HCl solution (with a concentration of 10 weight %) was then added to the resulting reaction mixture, which was subjected to liquid-liquid separation and extraction with EtOAc. Next, the organic layer collected was washed with brine, dried over Na$_2$SO$_4$, and filtered, followed by concentration under reduced pressure. Subsequently, the resulting crude product was purified by column chromatography (developing solvent: hexane/Et$_2$O=3/2 (volume ratio)) to obtain 1628 mg (6.6 mmol) of N-[3-(dimethylsilyl)propyl]phthalimide (12) in a yield of 94%. The reaction formula for the reaction is shown below.

[Chemical Formula 12]

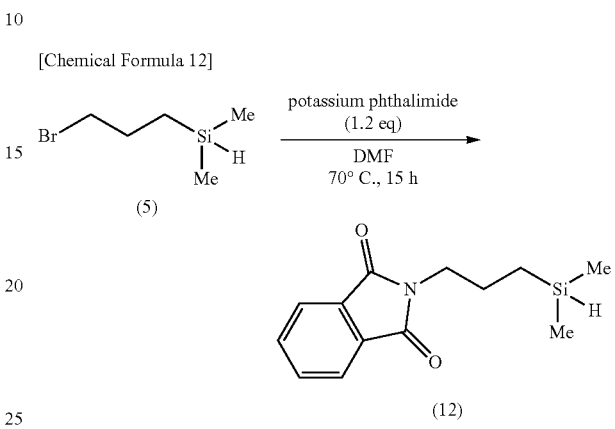

The N-[3-(dimethylsilyl)propyl]phthalimide obtained was identified by $^1$H-NMR measurement. The chemical shifts determined were as follows.

δ (ppm): 7.83-7.87 (m, 2H), 7.69-7.73 (m, 2H), 3.83-3.88 (m, 1H), 3.66-3.70 (t, J=7.2 Hz, 2H), 1.67-1.75 (m, 2H), 0.60-0.65 (m, 2H), 0.07-0.08 (d, J=4.0 Hz, 6H)

Production Example 13

Synthesis of (3-nitropropyl)dimethylsilane 3-(bromopropyl)dimethylsilane (1267 mg, 7.0 mmol) as prepared in Production Example 5 was added to a DMF solution (14 mL) of sodium nitrite (NaNO$_2$, 725 mg, 10.5 mmol), followed by stirring at room temperature for 6 hours. Et$_2$O and distilled water were then added for liquid-liquid separation and extraction. The organic layer was washed with brine, dried over Na$_2$SO$_4$, and filtered, followed by concentration under reduced pressure. Subsequently, the resulting crude product was purified by column chromatography (developing solvent: hexane/EtOAc=5/1 (volume ratio)) to obtain 329 mg (2.2 mmol) of (3-nitropropyl)dimethylsilane (13) in a yield of 32%. The reaction formula for the reaction is shown below.

[Chemical Formula 13]

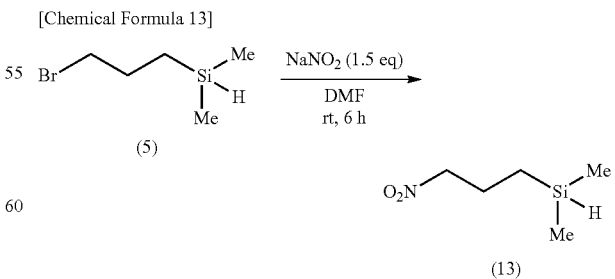

The (3-nitropropyl)dimethylsilane obtained was identified by 1H-NMR measurement. The chemical shifts determined were as follows.

δ (ppm): 4.36-4.40 (t, J=7.2 Hz, 2H), 3.87-3.92 (m, 1H), 2.02-2.10 (m, 2H), 0.62-0.66 (m, 2H), 0.11-0.12 (d, J=3.6 Hz, 6H)

Production Example 14

Preparation of 3-(dimethylsilylpropyl)magnesium chloride

THF (1 mL) and a piece of 12 were added to magnesium (365 mg, 15 mmol) under nitrogen atmosphere, and they were allowed to stand for 5 minutes. Next, THF (9 mL) and (3-chloropropyl)dimethylsilane (1365 mg, 10 mmol) as prepared in Production Example 4 were added, followed by stirring at 70° C. for 2 hours to obtain 3-(dimethylsilylpropyl)magnesium chloride (14) serving as a Grignard reagent. The reaction formula for the reaction is shown below.

[Chemical Formula 14]

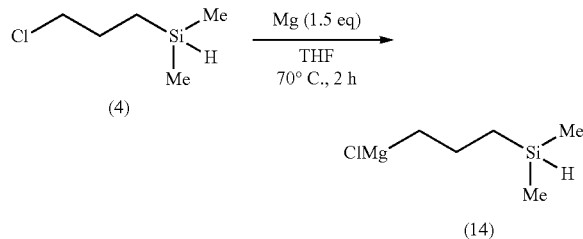

Production Example 15

Synthesis of 4-(dimethylsilyl)butyric acid

A THF solution of 3-(dimethylsilylpropyl)magnesium chloride as prepared in Production Example 14 (10 mL, 9.0 mmol) was stirred under carbon dioxide atmosphere at ordinary pressure and room temperature for 12 hours. An aqueous HCl solution (with a concentration of 10 weight %) was then added, and the aqueous layer was extracted with Et$_2$O. Next, the organic layer collected was subjected to liquid-liquid separation by adding a saturated aqueous solution of sodium hydrogen carbonate (NaHCO$_3$), then the aqueous layer was neutralized with an aqueous HCl solution (with a concentration of 10 weight %) and was subsequently extracted with Et$_2$O. The remaining organic layer was washed with brine and dried over Na$_2$SO$_4$. This was followed by filtration and then by concentration under reduced pressure, and the resulting mixture was purified by column chromatography (developing solvent: hexane/EtOAc=3/1 (volume ratio)) to obtain 618 mg (4.2 mmol) of 4-(dimethylsilyl)butyric acid (15) in a yield of 47%. The reaction formula for the reaction is shown below.

[Chemical Formula 15]

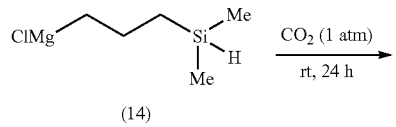

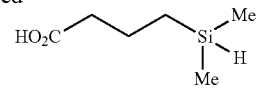

The 4-(dimethylsilyl)butyric acid obtained was identified by $^1$H-NMR measurement. The chemical shifts determined were as follows.

δ (ppm): 11.96 (s, 1H), 3.77-3.82 (m, 1H), 2.17-2.21 (t, J=7.2 Hz, 2H), 1.46-1.54 (m, 2H), 0.52-0.57 (m, 2H), 0.02-0.03 (d, J=3.6 Hz, 6H)

Production Example 16

Synthesis of ethyl 4-(dimethylsilyl)butyrate)

Under nitrogen atmosphere, a THF solution of 3-(dimethylsilylpropyl)magnesium chloride as prepared in Production Example 14 (10 mL, 9.0 mmol) was added dropwise slowly to a THF solution (2 mL) of ethyl chloroformate (1172 mg, 10.8 mmol) cooled to −30° C., followed by stirring at −30° C. for 1 hour. Next, the stirred mixture was taken out of a cooling chamber and was further stirred for 1 hour while being allowed to return to room temperature. Subsequently, the resulting mixed solution was concentrated under reduced pressure and then subjected to liquid-liquid separation by adding Et$_2$O and an aqueous HCl solution (with a concentration of 10 weight %). The aqueous layer was extracted with Et$_2$O, and the resulting organic layer was washed with brine and dried over Na$_2$SO$_4$. This was followed by filtration and then by concentration under reduced pressure, and the resulting mixture was purified by chromatography (developing solvent: hexane/EtOAc=30/1 (volume ratio)) to obtain 1394 mg (8.9 mmol) of ethyl 4-(dimethylsilyl)butyrate (16) in a yield of 89%. The reaction formula for the reaction is shown below.

[Chemical Formula 16]

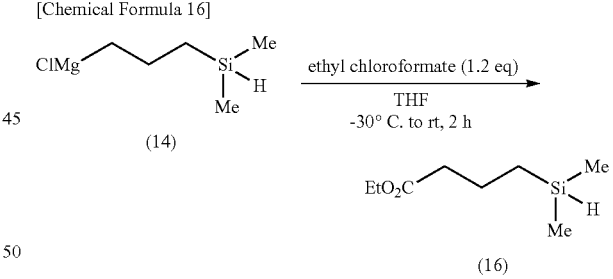

The ethyl 4-(dimethylsilyl)butyrate obtained was identified by 1H-NMR measurement. The chemical shifts determined were as follows.

δ (ppm): 4.11-4.15 (q, J=6.8 Hz, 2H), 3.84-3.89 (m, 1H), 2.32-2.36 (t, J=7.2 Hz, 2H), 1.65-1.73 (m, 2H), 1.25-1.29 (t, J=7.2 Hz, 3H), 0.60-0.65 (m, 2H), 0.08-0.09 (d, J=4.0 Hz, 6H)

Production Example 17

Synthesis of [3-(dimethylsilyl)propyl]diethylphosphate

Under nitrogen atmosphere, a THF solution of 3-(dimethylsilylpropyl)magnesium chloride as prepared in Production Example 14 (10 mL, 9.0 mmol) was added dropwise slowly to a THF solution (2 mL) of diethyl chlorophosphate (1864 mg, 10.8 mmol) cooled to −30° C., followed by stirring at −30° C. for 1 hour. Next, the stirred mixture was taken out of a cooling chamber and was stirred for 1 hour while being allowed to return to room temperature. Subsequently, the resulting mixed solution was concentrated under reduced pressure, and CH$_2$Cl$_2$ was added to the concentrated solution, which was subjected to liquid-liquid separation using an aqueous HCl solution (with a concentration of 10 weight %) and NaHCO$_3$. The aqueous layer was extracted with CH$_2$Cl$_2$, and the resulting organic layer was washed with brine and dried over Na$_2$SO$_4$. This was followed by filtration and then by concentration under reduced pressure, and the resulting mixture was purified by chromatography (developing solvent: hexane/EtOAc=1/2 (volume ratio)) to obtain 1992 mg (8.4 mmol) of [3-(dimethylsilyl)propyl] diethylphosphate (17) in a yield of 93%. The reaction formula for the reaction is shown below.

[Chemical Formula 17]

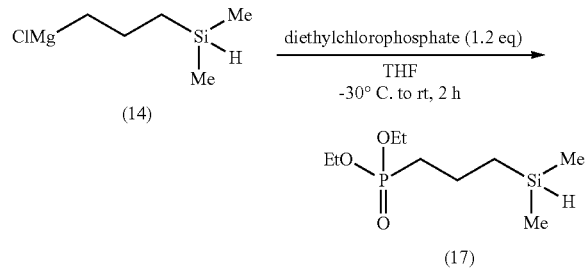

The [3-(dimethylsilyl)propyl] diethylphosphate obtained was identified by 10 $^1$H-NMR measurement. The chemical shifts determined were as follows.

δ (ppm): 4.02-4.16 (m, 4H), 3.83-3.88 (m, 1H), 1.61-1.83 (m, 4H), 1.31-1.34 (t, J=7.2 Hz, 6H), 0.68-0.73 (m, 2H), 0.08-0.09 (d, J=3.6 Hz, 6H)

Production Example 18

Synthesis of 3-mercaptopropyldimethylsilane

Under nitrogen atmosphere, a THF solution of 3-(dimethylsilylpropyl)magnesium chloride as prepared in Production Example 14 (10 mL, 9 mmol) was added to a THF solution (2 mL) of sulfur (346 mg, 10.8 mmol) cooled to 0° C., followed by stirring at room temperature for 12 hours. The resulting reaction mixture was then subjected to liquid-liquid separation using Et$_2$O and an aqueous HCl solution (with a concentration of 10 weight %). Subsequently, the aqueous layer was extracted with Et$_2$O, and the resulting organic layer was washed with brine and dried over Na$_2$SO$_4$. This was followed by filtration and then by concentration under reduced pressure to obtain a 3-(mercaptopropyl)dimethylsilane mixture (1073 mg) including a disulfide. The resulting mixture (1073 mg) was then added to a Et$_2$O solution (16 mL) of LiAH$_4$ (304 mg, 8 mmol), followed by stirring at 40° C. for 1 hour. Subsequently, the resulting reaction mixture was subjected to liquid-liquid separation by adding an aqueous HCl solution (with a concentration of 10 weight %). The aqueous layer was extracted with Et$_2$O, and the organic layer collected was washed with brine and dried over Na$_2$SO$_4$. After that, the solution was filtered, followed by distillation under reduced pressure to obtain 820 mg (6.1 mmol) of (3-mercaptopropyl)dimethylsilane (18) in a yield of 68%. The reaction formula for the reaction is shown below.

[Chemical Formula 18]

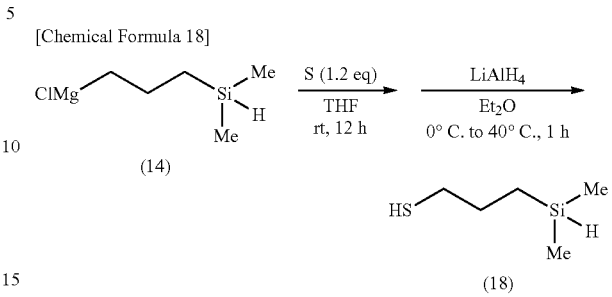

The (3-mercaptopropyl)dimethylsilane obtained was identified by $^1$H-NMR measurement. The chemical shifts determined were as follows.

δ (ppm): 3.84-3.89 (m, 1H), 2.52-2.57 (q, J=7.6 Hz, 2H), 1.62-1.70 (m, 2H), 1.33-1.37 (t, J=7.6 Hz, 1H), 0.66-0.71 (m, 2H), 0.08-0.09 (d, J=3.6 Hz, 6H)

Production Example 19

Synthesis of 4-(dimethylsilyl)butanol

Under nitrogen atmosphere, a THF solution of 3-(dimethylsilylpropyl)magnesium chloride as prepared in Production Example 14 (10 mL, 9.2 mmol) was added to a THF solution (2 mL) of paraformaldehyde (332 mg, 11.0 mmol) cooled to 0° C., followed by stirring at room temperature for 18 hours. The reaction mixture was then subjected to liquid-liquid separation and extraction by adding Et$_2$O and an aqueous HCl solution (with a concentration of 10 weight %), and the organic layer collected was washed with brine and then dried over Na$_2$SO$_4$. This was followed by filtration, then by concentration under reduced pressure, and then by distillation to obtain 1095 mg (8.3 mmol) of 4-(dimethylsilyl)butanol (19) in a yield of 90%. The reaction formula for the reaction is shown below.

[Chemical Formula 19]

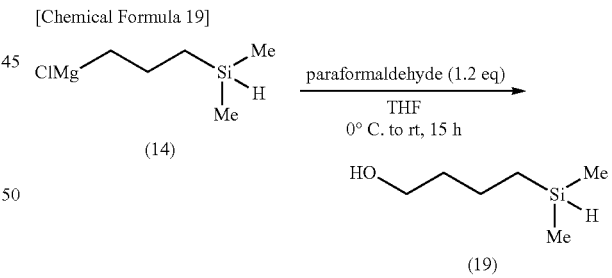

The 4-(dimethylsilyl)butanol obtained was identified by 1H-NMR measurement. The chemical shifts determined were as follows.

δ (ppm): 3.83-3.88 (m, 1H), 3.64-3.67 (t, J=6.4 Hz, 2H), 1.58-1.65 (m, 2H), 1.39-1.47 (m, 2H), 1.19 (bs, 1H), 0.59-0.64 (m, 2H), 0.07-0.08 (d, J=3.6 Hz, 6H)

Production Example 20

Synthesis of (3-benzoylpropyl)dimethylsilane

A two-necked flask containing magnesium (365 mg, 15 mmol) was heated under vacuum atmosphere and then purged with nitrogen, and Et$_2$O (2 mL) and a small amount of I$_2$ were added. Next, the mixture was heated to 45° C., and a Et$_2$O solution (10 mL) of (3-chloropropyl)dimethylsilane (1365 mg, 10 mmol) as prepared in Production Example 4 was added slowly to the mixture, followed by stirring at 45° C. for 4 hours. The resulting supernatant solution was then added slowly to an ice-cooled Et$_2$O solution (2 mL) of benzonitrile (1236 mg, 12.0 mmol), followed by stirring at 45° C. for 15 hours. Subsequently, the resulting reaction mixture was subjected to liquid-liquid separation by adding Et$_2$O and an aqueous HCl solution (with a concentration of 10 weight %). The resulting organic layer was washed with brine and dried over Na$_2$SO$_4$. This was followed by concentration under reduced pressure and then purification by chromatography (developing solvent: hexane/EtOAc=20/1 (volume ratio)) to obtain 1339 mg (6.5 mmol) of (3-benzoylpropyl)dimethylsilane (20) in a yield of 65%. The reaction formula for the reaction is shown below.

[Chemical Formula 20]

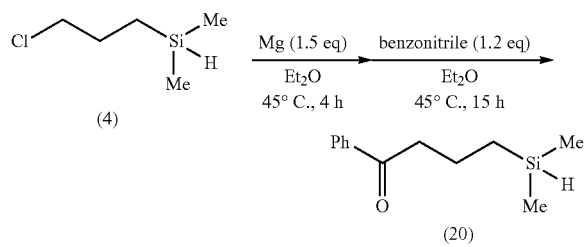

The (3-benzoylpropyl)dimethylsilane obtained was identified by $^1$H-NMR measurement. The chemical shifts determined were as follows.

δ (ppm): 7.95-7.98 (m, 2H), 7.54-7.58 (s, 1H), 7.44-7.49 (m, 2H), 3.86-3.91 (m, 1H), 3.00-3.03 (t, J=7.2 Hz, 2H), 1.77-1.85 (m, 2H), 0.66-0.71 (m, 2H), 0.09-0.10 (d, J=3.6 Hz, 6H)

Production Example 21

Synthesis of 7-[(3-dimethylsilyl)propoxy]coumarin

Under nitrogen atmosphere, umbelliferone (486 mg, 3.0 mmol) was added little by little to a DMF solution (9 mL) of sodium hydride (72 mg, 3.0 mmol) cooled to 0° C., followed by stirring for 30 minutes. (3-bromopropyl)dimethylsilane (655 mg, 3.6 mmol) as prepared in Production Example 5 was then added, followed by stirring at 60° C. for 12 hours. Subsequently, the resulting reaction mixture was subjected to liquid-liquid separation and extraction by adding distilled water and CH$_2$Cl$_2$, and the organic layer was washed with brine and then dried over Na$_2$SO$_4$. This was followed by filtration, then concentration under reduced pressure, and then purification by chromatography (developing solvent: hexane/EtOAc=8/1 (volume ratio)) to obtain 677 mg (2.58 mmol) of 7-[(3-dimethylsilyl)propoxy]coumarin (21) in a yield of 86%. The reaction formula for the reaction is shown below.

[Chemical Formula 21]

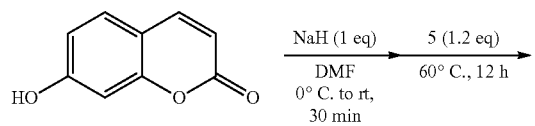

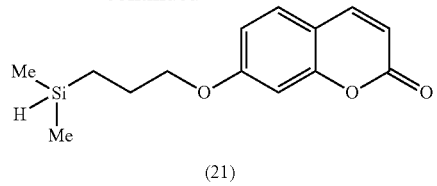

The 7-[(3-dimethylsilyl)propoxy]coumarin obtained was identified by $^1$H-NMR measurement. The chemical shifts determined were as follows.

δ (ppm): 7.63-7.65 (d, J=9.6 Hz, 2H), 7.36-7.38 (d, J=8.8 Hz, 2H), 6.80-6.85 (m, 2H), 6.24-6.26 (d, J=9.2 Hz, 1H), 3.98-4.01 (t, J=6.8 Hz, 2H), 3.89-3.94 (m, 1H), 1.83-1.91 (m, 2H), 0.70-0.75 (m, 2H), 0.11-0.12 (d, J=3.6 Hz, 6H)

The hydrosilane compounds prepared in Production Examples 1 to 9, 11 to 13, and 15 to 21 are collectively listed in Table 1 given below. Among the hydrosilane compounds listed in Table 1, 1-(dimethylsilyl)pyrene (Production Example 2), (dimethylsilyl)ferrocene (Production Example 3), 1-(3-dimethylsilylpropyl)naphthalene (Production Example 6), (3-azidopropyl)dimethylsilane (Production Example 7), [3-(dimethylsilyl)propyl]acrylamide (Production Example 9), 1-(3-dimethylsilylpropyl)-3-methylimidazolium iodide (Production Example 11), (3-nitropropyl)dimethylsilane (Production Example 13), 4-(dimethylsilyl)butyric acid (Production Example 15), ethyl 4-(dimethylsilyl)butyrate (Production Example 16), [3-(dimethylsilyl)propyl] diethylphosphate (Production Example 17), 4-(dimethylsilyl)butanol (Production Example 19), and (3-benzoylpropyl)dimethylsilane (Production Example 20) are new compounds. 1-(3-dimethylsilylpropyl)imidazole (Production Example 10), which is a precursor of 1-(3-dimethylsilylpropyl)-3-methylimidazolium iodide prepared in Production Example 11, is also a new compound.

TABLE 1

| | |
|---|---|
| Production Example 1 | 1-(dimethylsilyl)naphthalene |
| Production Example 2 | 1-(dimethylsilyl)pyrene |
| Production Example 3 | (Dimethylsilyl)ferrocene |
| Production Example 4 | (3-chloropropyl)dimethylsilane |
| Production Example 5 | (3-bromopropyl)dimethylsilane |
| Production Example 6 | 1-(3-dimethylsilylpropyl)naphthalene |
| Production Example 7 | (3-azidopropyl)dimethylsilane |
| Production Example 8 | (3-aminopropyl)dimethylsilane |
| Production Example 9 | [3-(dimethylsilyl)propyl]acrylamide |
| Production Example 11 | 1-(3-dimethylsilylpropyl)-3-methylimidazolium iodide |
| Production Example 12 | N-[3-(dimethylsilyl)propyl]phthalimide |
| Production Example 13 | (3-nitropropyl)dimethylsilane |
| Production Example 15 | 4-(dimethylsilyl)butyric acid |
| Production Example 16 | Ethyl 4-(dimethylsilyl)butyrate |
| Production Example 17 | [3-(dimethylsilyl)propyl] diethylphosphate |
| Production Example 18 | 3-mercaptopropyldimethylsilane |

TABLE 1-continued

| Production Example 19 | 4-(dimethylsilyl)butanol |
| --- | --- |
| Production Example 20 | (3-benzoylpropyl)dimethylsilane |
| Production Example 21 | 7-[(3-dimethylsilyl)propoxy]coumarin |

Example 1

Modification of Surface of Silica Gel

A silica gel (MCM-41, 100 mg), which is mesoporous silica, was dried under reduced pressure at 180° C. for 6 hours and then further dried using a heat gun. The dried silica gel was then cooled to room temperature. After that, under nitrogen atmosphere, $CH_2Cl_2$ (3.0 mL), a hydrosilane compound (0.5 mmol, corresponding to about 1 equivalent relative to the Si—OH groups of the silica), and trispentafluorophenylborane ($B(C_6F_5)_3$, 1.3 mg, 5 μmol, corresponding to about 1 mol % relative to the Si—OH groups of the silica) were sequentially added, followed by standing at room temperature for 5 minutes. Example 1 employed 24 types of hydrosilane compounds (Examples 1-1 to 1-24). In every case, hydrogen was evolved upon the addition of $B(C_6F_5)_3$. After confirmation of cessation of the evolution of hydrogen, the resulting silica gel was filtered and washed thoroughly with $CH_2Cl_2$. Next, the washed silica was dried under reduced pressure at room temperature for 2 hours to obtain a silica gel having its surface modified (functionalized) with the molecular structure A of the hydrosilane compound.

The reaction formula for the reaction is shown below. In the reaction formulae given hereinafter, the hydrosilane compound is denoted by "$SiH(CH_3)_2$-FG" ("FG" is a functional group). In Example 1-8, "$SiH_2CH_3$—FG" was used as the hydrosilane compound.

[Chemical Formula 22]

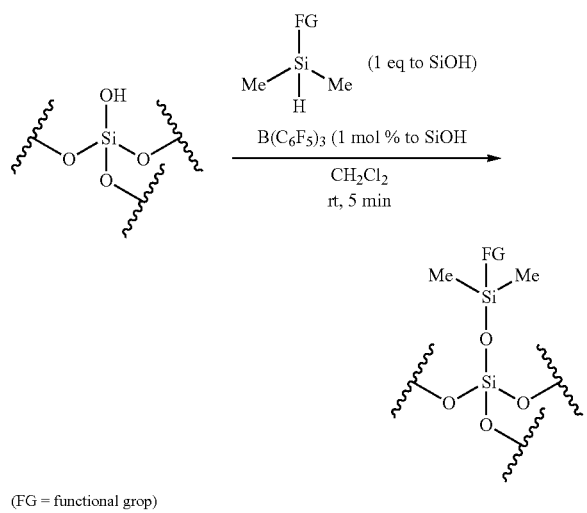

(FG = functional grop)

Example 1-1

1-(dimethylsilyl)naphthalene as prepared in Production Example 1 was used as the hydrosilane compound.

Example 1-2

1-(dimethylsilyl)pyrene as prepared in Production Example 2 was used as the hydrosilane compound.

Example 1-3

Commercially-available 1-(dimethylsilyl)benzene was used as the hydrosilane compound.

Example 1-4

(Dimethylsilyl)ferrocene as prepared in Production Example 3 was used as the hydrosilane compound.

Example 1-5

Commercially-available 1-(dimethylsilylmethyl)benzene was used as the hydrosilane compound.

Example 1-6

(3-chloropropyl)dimethylsilane as prepared in Production Example 4 was used as the hydrosilane compound.

Example 1-7

Commercially-available (3-chloropropyl)methylsilane was used as the hydrosilane compound.

Example 1-8

(3-bromopropyl)dimethylsilane as prepared in Production Example 5 was used as the hydrosilane compound.

Example 1-9

(3-azidopropyl)dimethylsilane as prepared in Production Example 7 was used as the hydrosilane compound.

Example 1-10

(3-aminopropyl)dimethylsilane as prepared in Production Example 8 was used as the hydrosilane compound.

Example 1-11

3-mercaptopropyldimethylsilane as prepared in Production Example 18 was used as the hydrosilane compound.

Example 1-12

(3-nitropropyl)dimethylsilane as prepared in Production Example 13 was used as the hydrosilane compound.

Example 1-13

[3-(dimethylsilyl)propyl] diethylphosphate as prepared in Production Example 17 was used as the hydrosilane compound.

Example 1-14

Ethyl 4-(dimethylsilyl)butyrate as prepared in Production Example 16 was used as the hydrosilane compound.

Example 1-15

4-(dimethylsilyl)butyric acid as prepared in Production Example 15 was used as the hydrosilane compound.

Example 1-16

7-[(3-dimethylsilyl)propoxy]coumarin as prepared in Production Example 21 was used as the hydrosilane compound.

Example 1-17

4-(dimethylsilyl)butanol as prepared in Production Example 19 was used as the hydrosilane compound.

Example 1-18

Commercially-available 1-(dimethylsilyl)dotriacontane was used as the hydrosilane compound.

Example 1-19

1-(3-dimethylsilylpropyl)naphthalene as prepared in Production Example 6 was used as the hydrosilane compound.

Example 1-20

[3-(dimethylsilyl)propyl]acrylamide as prepared in Production Example 9 was used as the hydrosilane compound.

Example 1-21

N-[3-(dimethylsilyl)propyl]phthalimide as prepared in Production Example 12 was used as the hydrosilane compound.

Example 1-22

1-(3-dimethylsilylpropyl)-3-methylimidazolium iodide as prepared in Production Example 11 was used as the hydrosilane compound.

Example 1-23

Commercially-available 2-methyl-2-(dimethylsilyl)propane was used as the hydrosilane compound.

Example 1-24

(3-benzoylpropyl)dimethylsilane as prepared in Production Example 20 was used as the hydrosilane compound.

In all of Examples 1-1 to 1-24, hydrogen was evolved upon the addition of $B(C_6F_5)_3$, which confirmed that a dehydrocondensation reaction takes place between the Si—OH group present on the surface of the silica gel and the hydrosilane compound. In all of Examples, the evolution of hydrogen ceased during standing at room temperature for 5 minutes, which confirmed that the reaction is progressed at room temperature in a short time. Results of infrared spectroscopy (IR) evaluation of the surface-modified silica gels fabricated in Examples 1-1 to 1-24 are shown in FIGS. 3 to 26, respectively. The IR profiles shown in FIGS. 3 to 26 verify that the modification of the surface of the silica gel with the molecular structure A of the hydrosilane compound was accomplished in each Example. Even when the molecular structure A contained a group reactive with the Si—OH group of the silica gel (such as Example 1-15 in which the molecular structure A contained a carboxyl group), the dehydrocondensation reaction took place selectively between the Si—OH group of the silica gel and the hydrosilyl group. That is, in Example 1-15, the modification of the surface of the base material was achieved by the molecular structure A containing a carboxyl group. Given that such surface modification in which a carboxyl group remains in the modifying structure has hitherto been impossible, these Examples demonstrate that the method according to the present disclosure has very high industrial utility. The IR measurement was performed by diffuse reflectance spectroscopy using FT/IR-4000 manufactured by JASCO Corporation. This is the same for Examples and Comparative Examples described later.

Besides the IR evaluation, element analysis was performed on the surface-modified silica gels fabricated in Examples 1-1 to 1-24 to evaluate the amount of the molecular structure A supported on the surface of each silica gel. The evaluation results are shown in Table 2 below.

TABLE 2

| Example No. | Supported amount mmol · g$^{-1}$ |
|---|---|
| 1-1 | 0.73 |
| 1-2 | 0.53 |
| 1-3 | 1.29 |
| 1-4 | 0.57 |
| 1-5 | 1.51 |
| 1-6 | 1.61 |
| 1-7 | 1.70 |
| 1-8 | 1.72 |
| 1-9 | 1.75 |
| 1-10 | 1.15 |
| 1-11 | 1.51 |
| 1-12 | 1.34 |
| 1-13 | 1.23 |
| 1-14 | 1.48 |
| 1-15 | 1.25 |
| 1-16 | 1.13 |
| 1-17 | 1.64 |
| 1-18 | 0.77 |
| 1-19 | 1.56 |
| 1-20 | 0.53 |
| 1-21 | 1.26 |
| 1-22 | 0.98 |
| 1-23 | 0.39 |
| 1-24 | 1.10 |

Comparative Example 1

Use of Platinum Catalyst

A silica gel (MCM-41, 100 mg) was dried under reduced pressure at 180° C. for 6 hours and then further dried using a heat gun. The dried silica gel was then cooled to room temperature. After that, under nitrogen atmosphere, toluene (3.0 mL), (3-chloropropyl)dimethylsilane as prepared in Production Example 4 (63 mg, 0.5 mmol, corresponding to about 1 equivalent relative to the Si—OH groups of the silica), and di-μ-chloro-dichloro-bis(ethylene)diplatinum(II) as a platinum catalyst (2.94 mg, 5 μmol, corresponding to about 1 mol % relative to the Si—OH groups of the silica) were sequentially added, followed by stirring at room temperature for 10 minutes. Next, after confirmation of cessation of the evolution of hydrogen, the resulting silica gel was filtered and thoroughly washed with toluene. Subsequently, the washed silica was dried under reduced pressure at room temperature for 2 hours to obtain a silica gel having its surface modified (functionalized) with the molecular structure A of the hydrosilane compound. The platinum catalyst exhibits a catalytic activity similar to that of cis-dichlorobis (styrene)platinum(II) used in Patent Literature 1.

The reaction formula for the reaction is shown below.

[Chemical Formula 23]

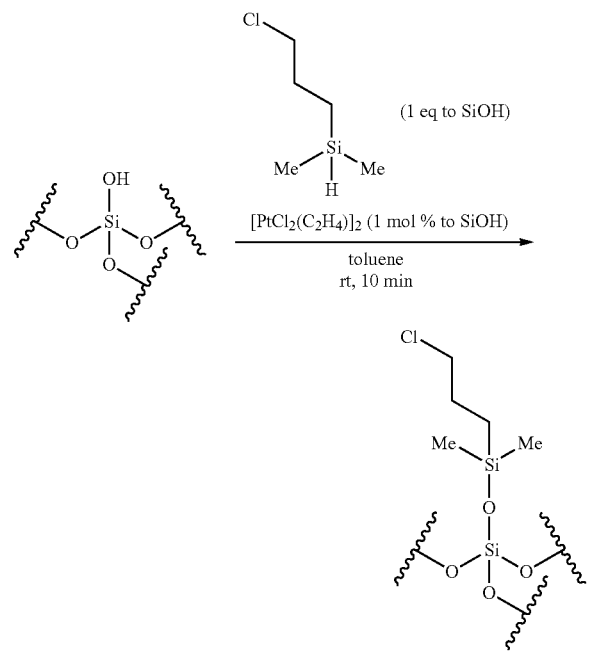

Figure 27:
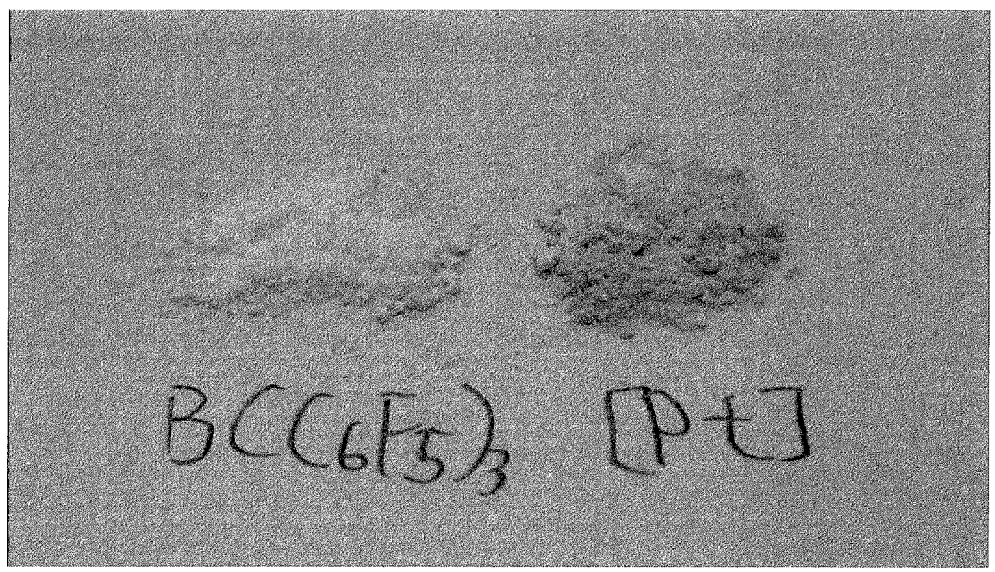
FIG. 27 shows the appearances of a surface-modified silica gel fabricated in Comparative Example 1 and a surface-modified silica gel fabricated in Example 1-6.

FIG. 27 shows the appearances of the surface-modified silica gel fabricated in Comparative Example 1 and the surface-modified silica gel fabricated in Example 1-6 using the same hydrosilane compound as used in Comparative Example 1. As shown in FIG. 27, the surface-modified silica gel of Example 1-6 (the sample on the left in FIG. 27) fabricated using a borane catalyst was white like the silica gel that had yet to be surface-modified, while the surface-modified silica gel of Comparative Example 1 (the sample on the right in FIG. 27) fabricated using a platinum catalyst was colored. The occurrence of this coloring was thought to be due to adsorption of a metal compound (platinum compound) on the surface of the silica gel.

Figure 8:
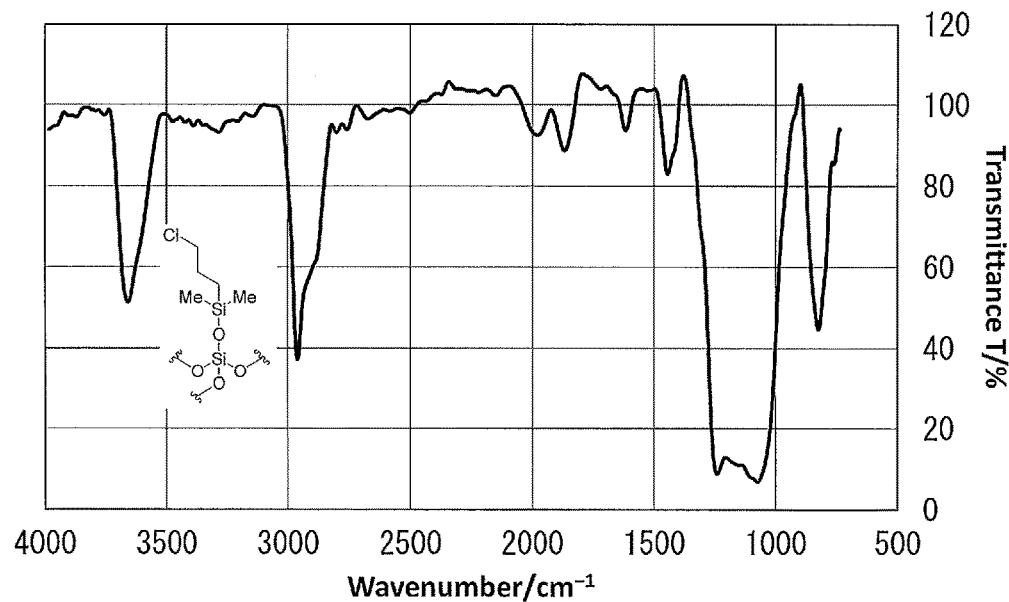
FIG. 8 shows an IR spectrum of a surface-modified silica gel fabricated in Example 1-6.
Figure 9:
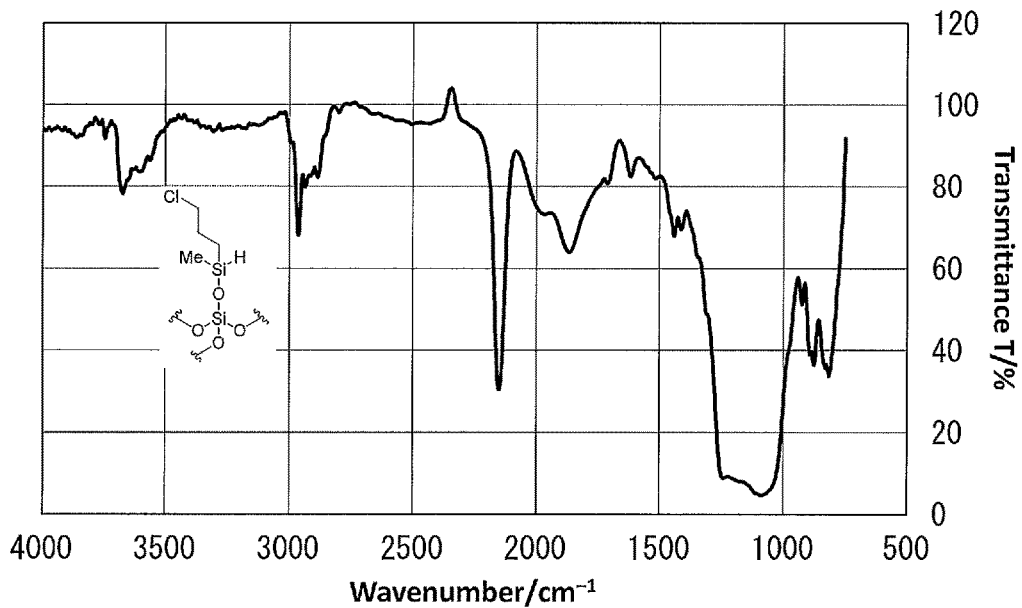
FIG. 9 shows an IR spectrum of a surface-modified silica gel fabricated in Example 1-7.
Figure 10:
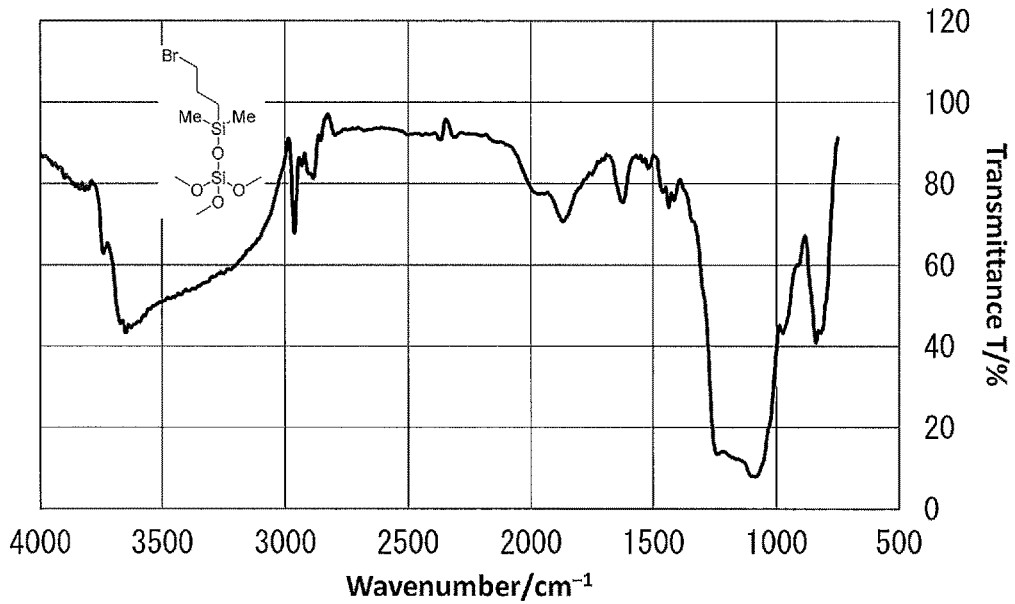
FIG. 10 shows an IR spectrum of a surface-modified silica gel fabricated in Example 1-8.
Figure 11:
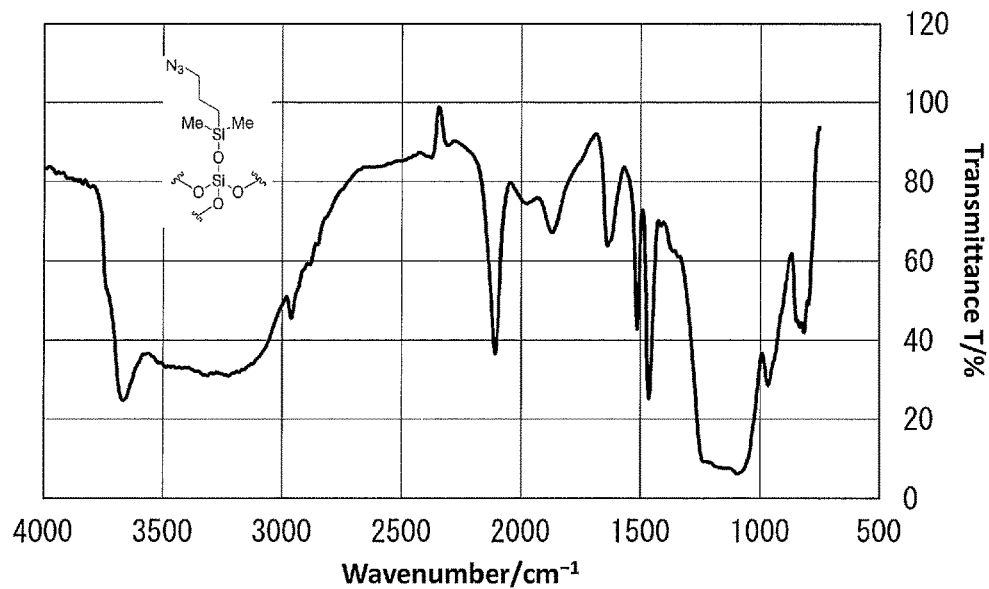
FIG. 11 shows an IR spectrum of a surface-modified silica gel fabricated in Example 1-9.
Figure 12:
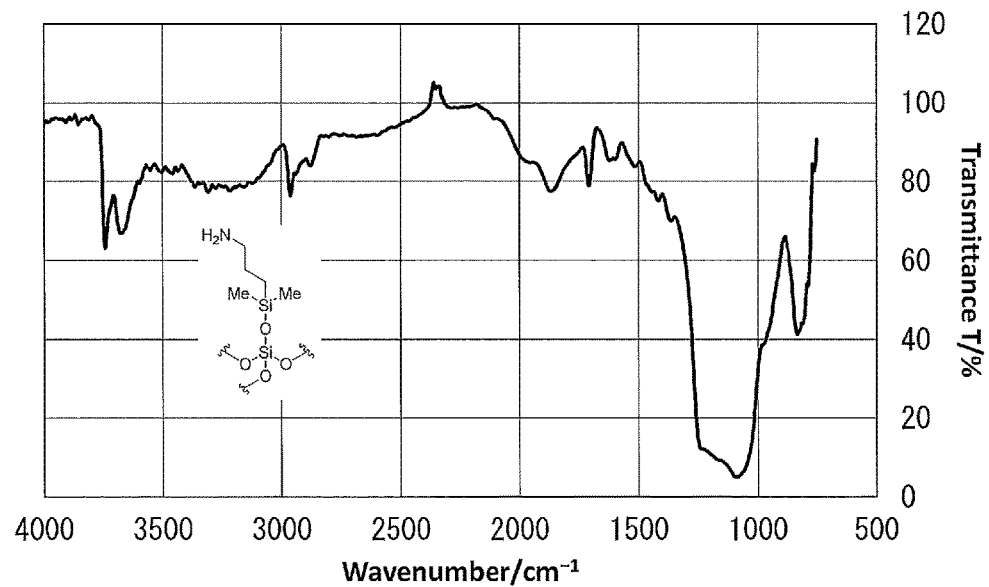
FIG. 12 shows an IR spectrum of a surface-modified silica gel fabricated in Example 1-10.
Figure 13:
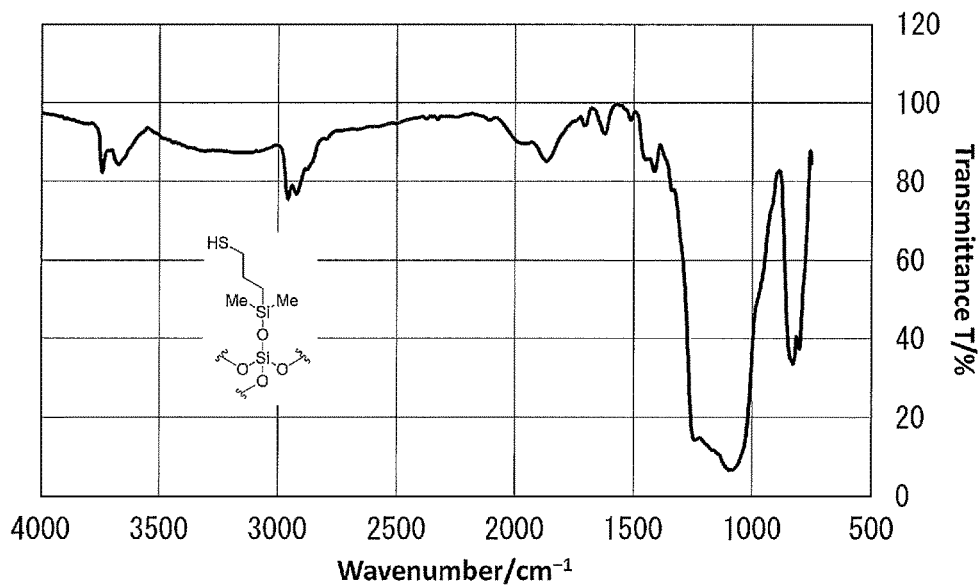
FIG. 13 shows an IR spectrum of a surface-modified silica gel fabricated in Example 1-11.
Figure 14:
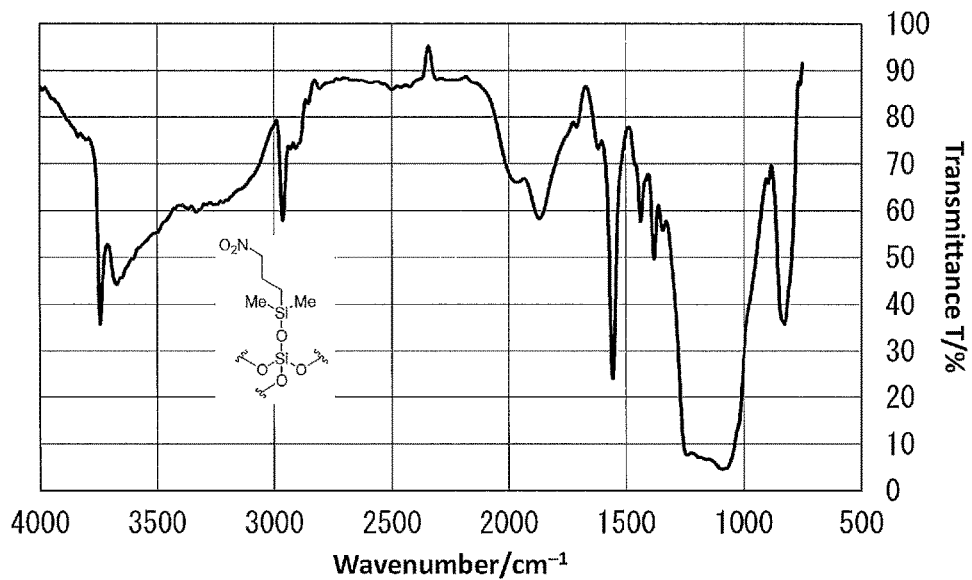
FIG. 14 shows an IR spectrum of a surface-modified silica gel fabricated in Example 1-12.
Figure 15:
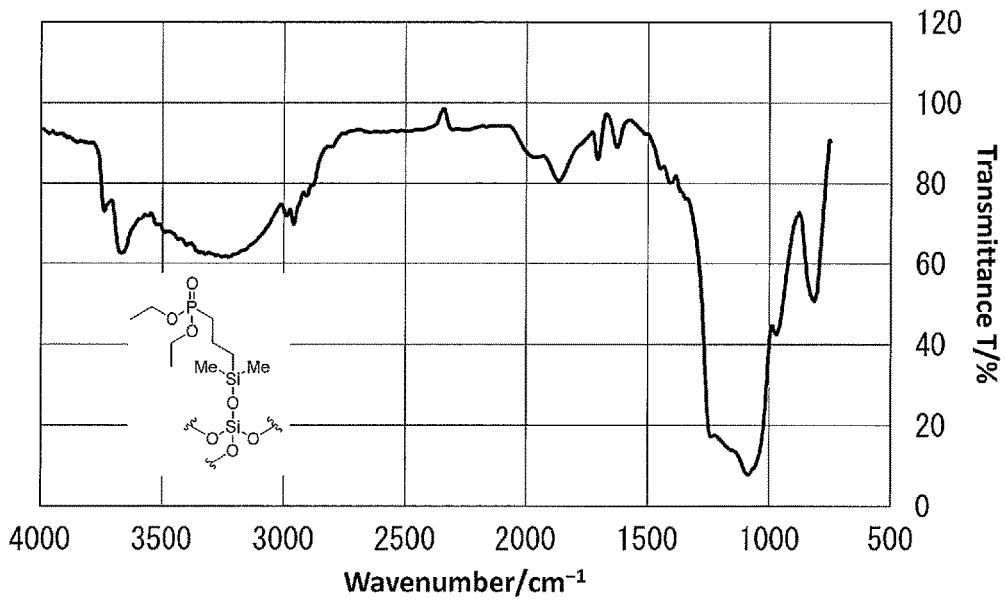
FIG. 15 shows an IR spectrum of a surface-modified silica gel fabricated in Example 1-13.
Figure 16:
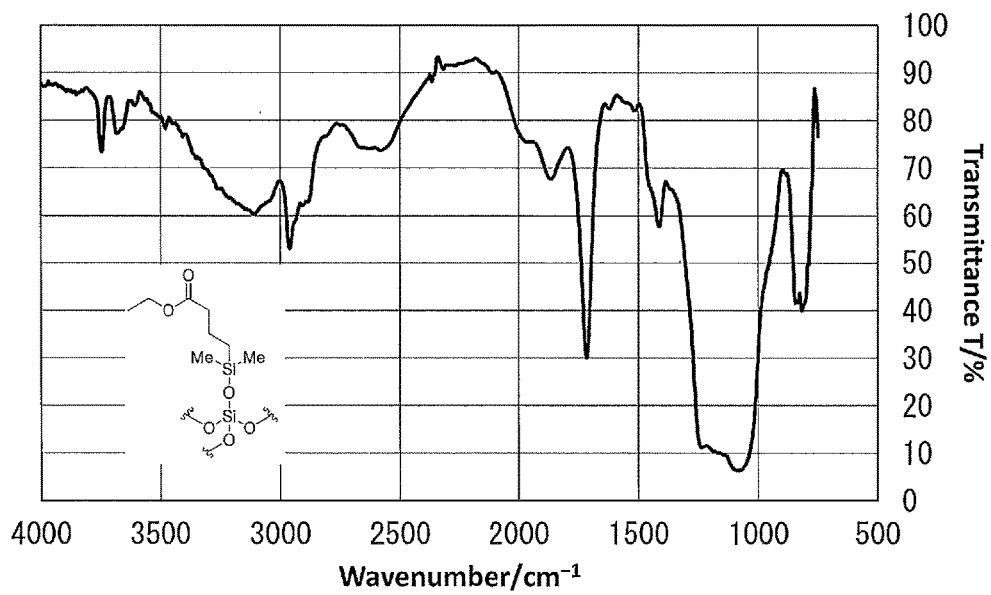
FIG. 16 shows an IR spectrum of a surface-modified silica gel fabricated in Example 1-14.
Figure 17:
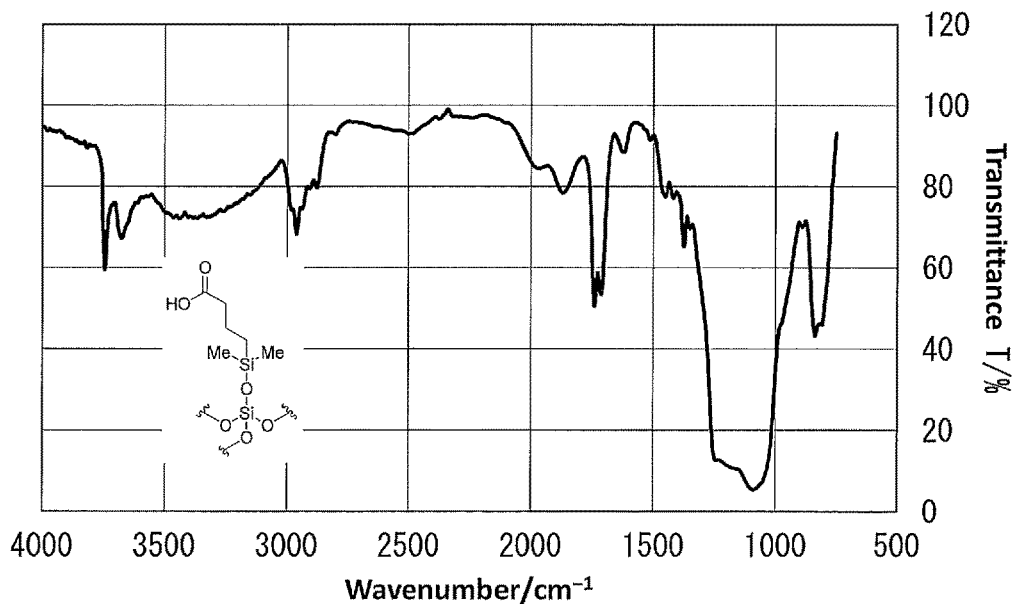
FIG. 17 shows an IR spectrum of a surface-modified silica gel fabricated in Example 1-15.
Figure 18:
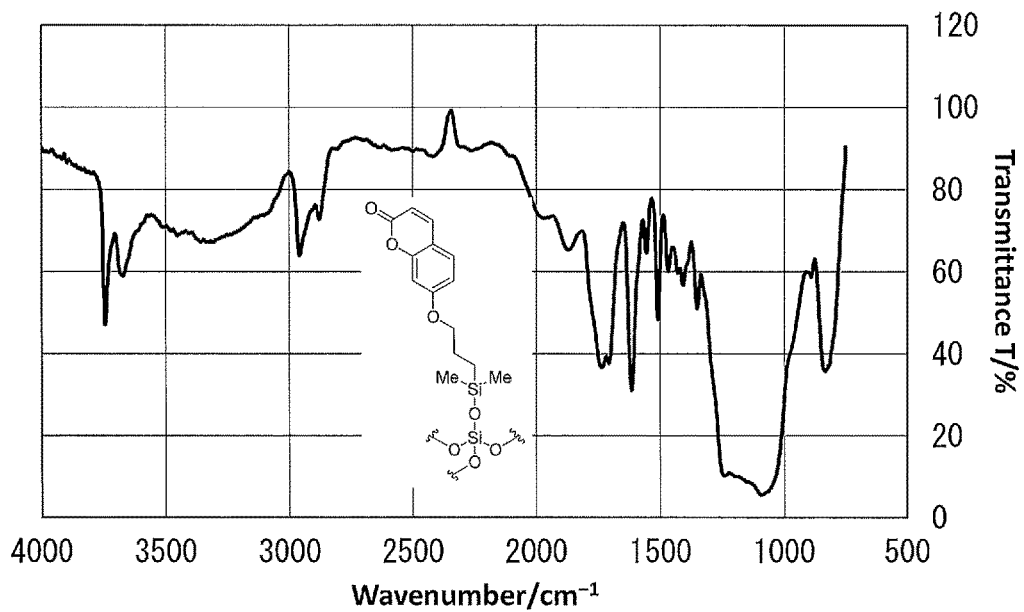
FIG. 18 shows an IR spectrum of a surface-modified silica gel fabricated in Example 1-16.
Figure 19:
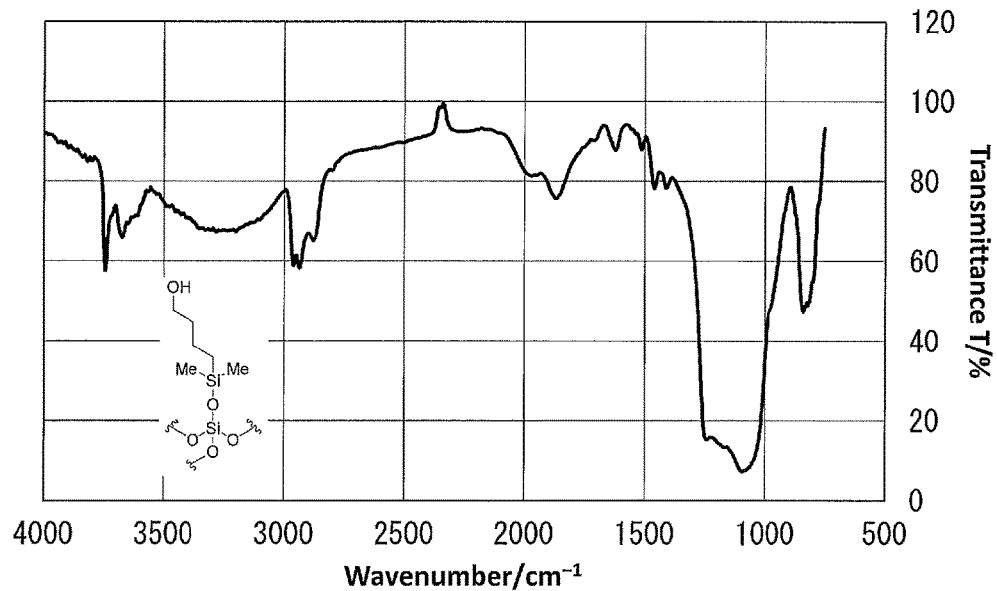
FIG. 19 shows an IR spectrum of a surface-modified silica gel fabricated in Example 1-17.
Figure 20:
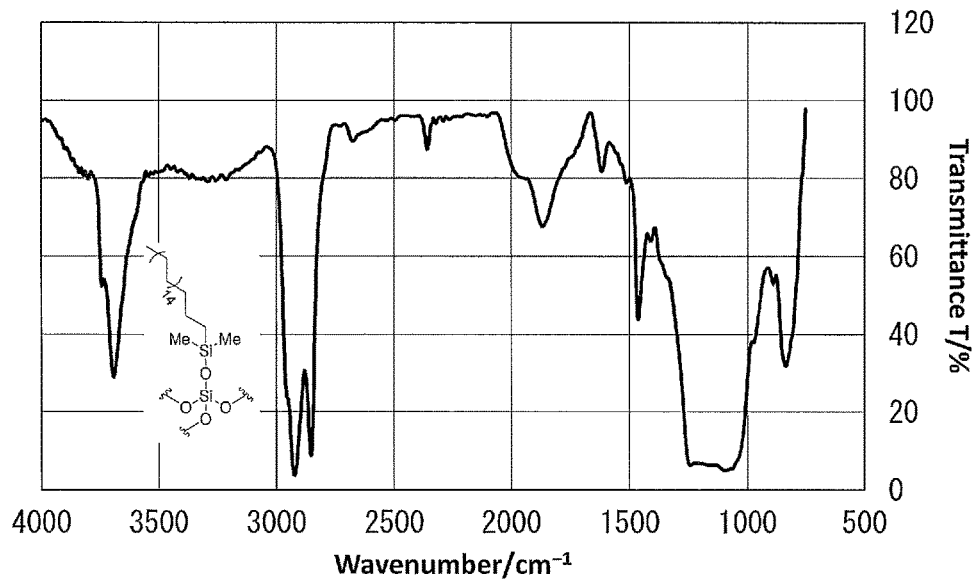
FIG. 20 shows an IR spectrum of a surface-modified silica gel fabricated in Example 1-18.
Figure 21:
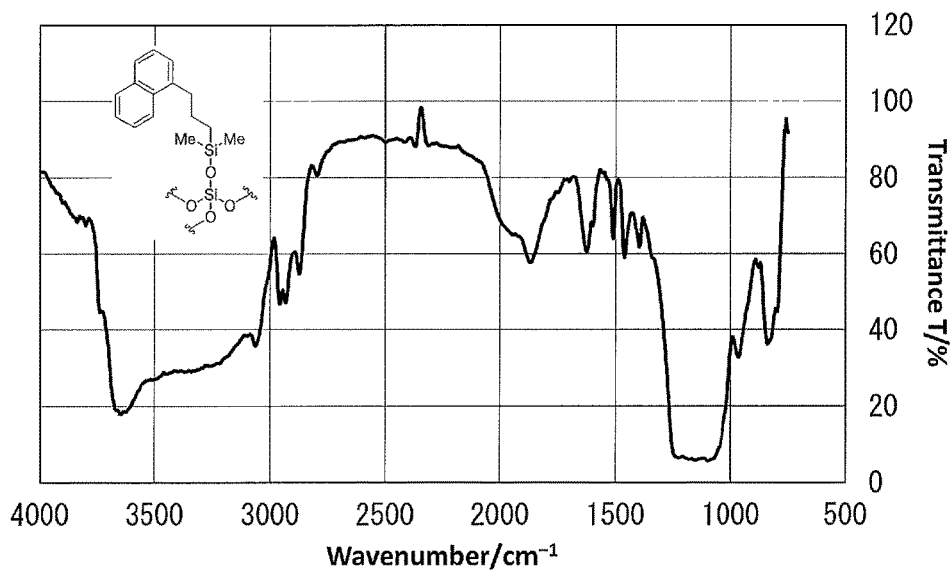
FIG. 21 shows an IR spectrum of a surface-modified silica gel fabricated in Example 1-19.
Figure 22:
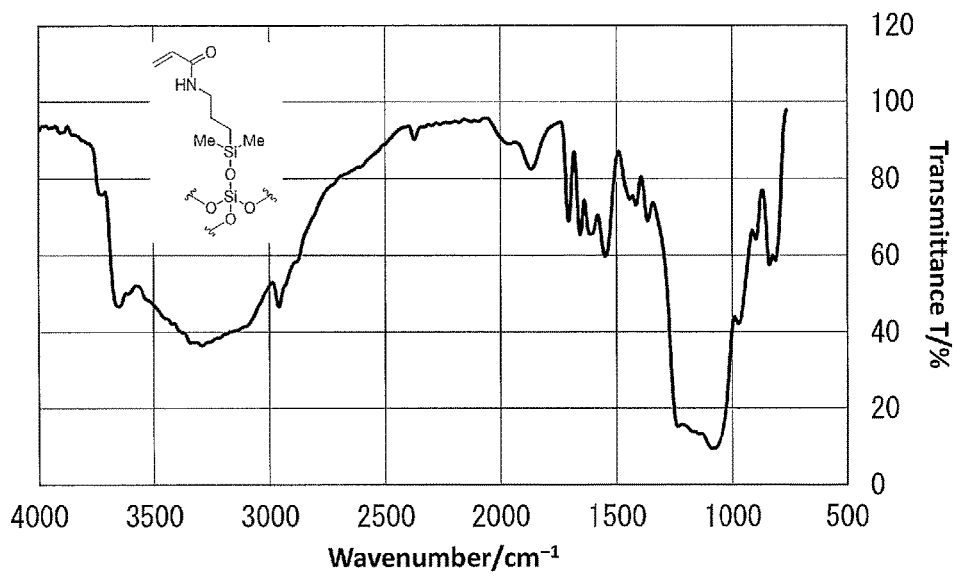
FIG. 22 shows an IR spectrum of a surface-modified silica gel fabricated in Example 1-20.
Figure 23:
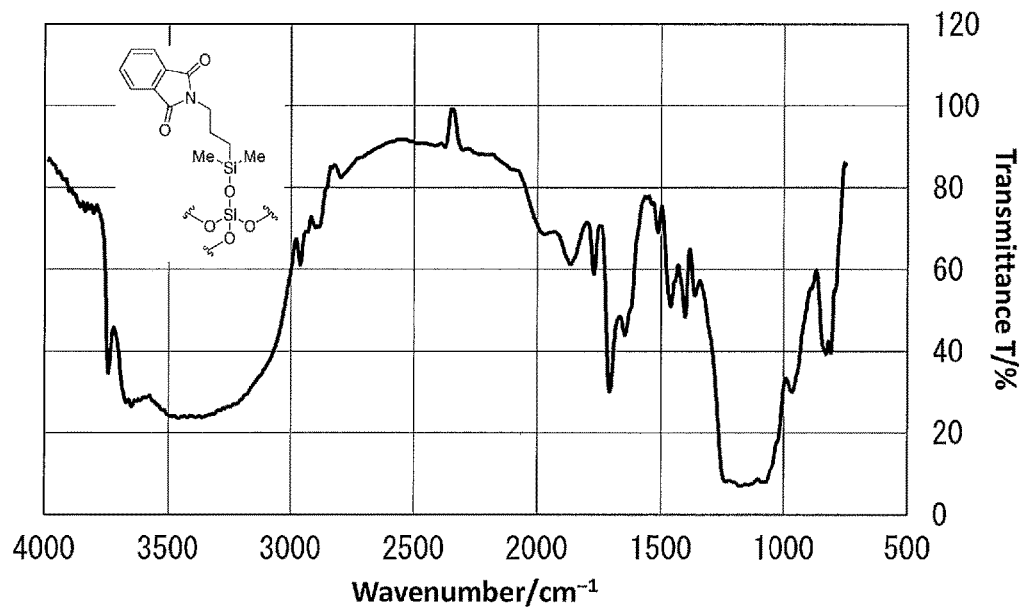
FIG. 23 shows an IR spectrum of a surface-modified silica gel fabricated in Example 1-21.
Figure 24:
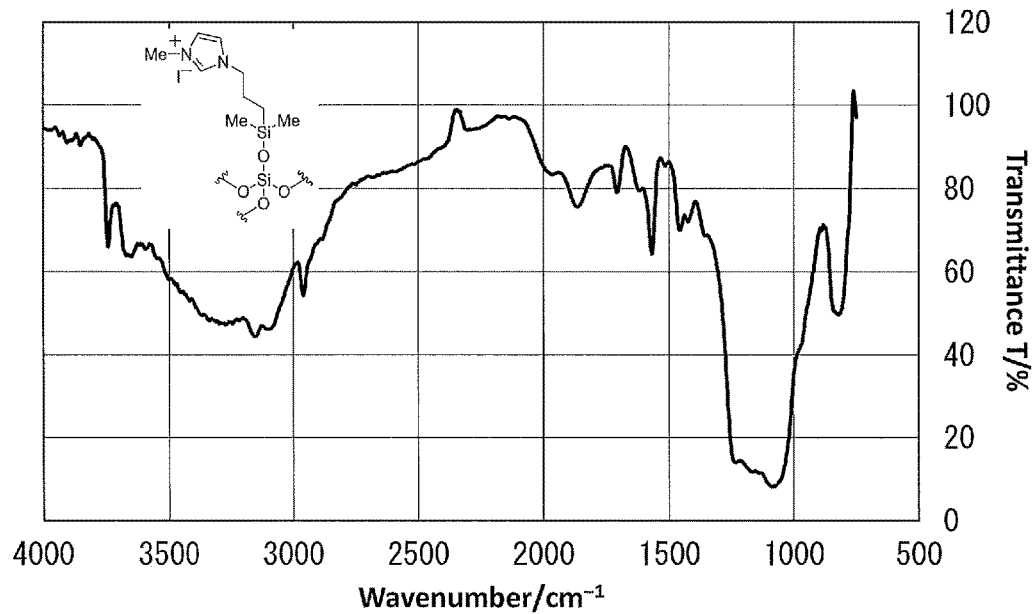
FIG. 24 shows an IR spectrum of surface-modified silica gel fabricated in Example 1-22.
Figure 25:
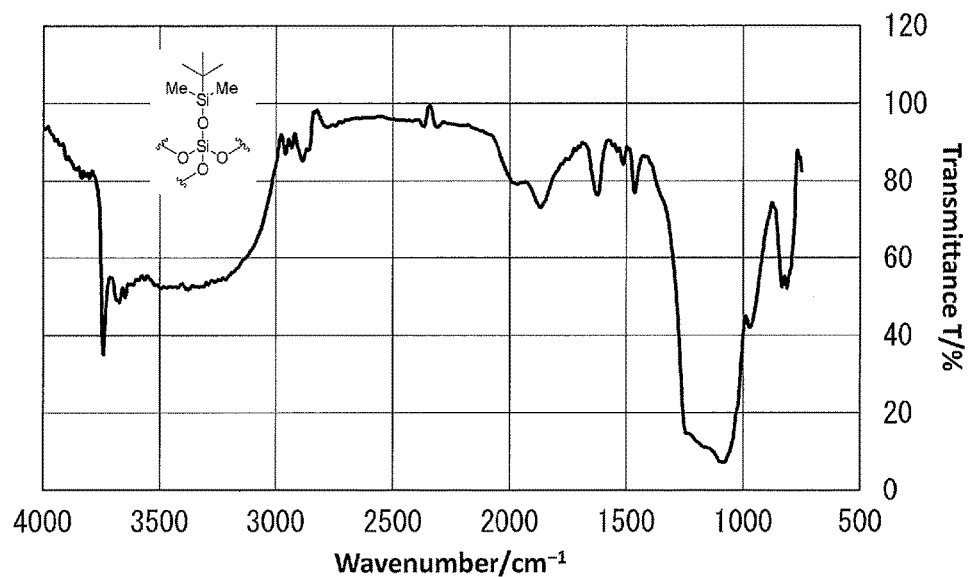
FIG. 25 shows an IR spectrum of a surface-modified silica gel fabricated in Example 1-23.
Figure 26:
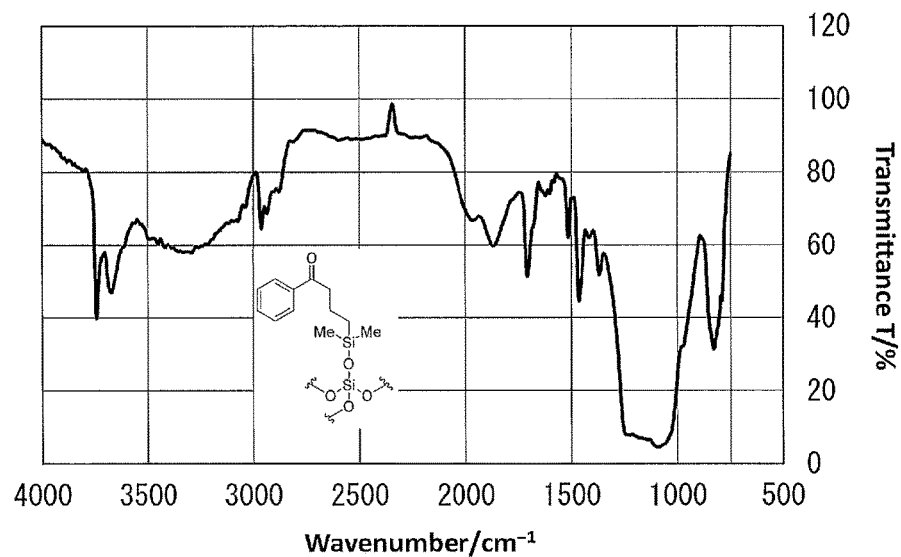
FIG. 26 shows an IR spectrum of a surface-modified silica gel fabricated in Example 1-24.
Figure 28:
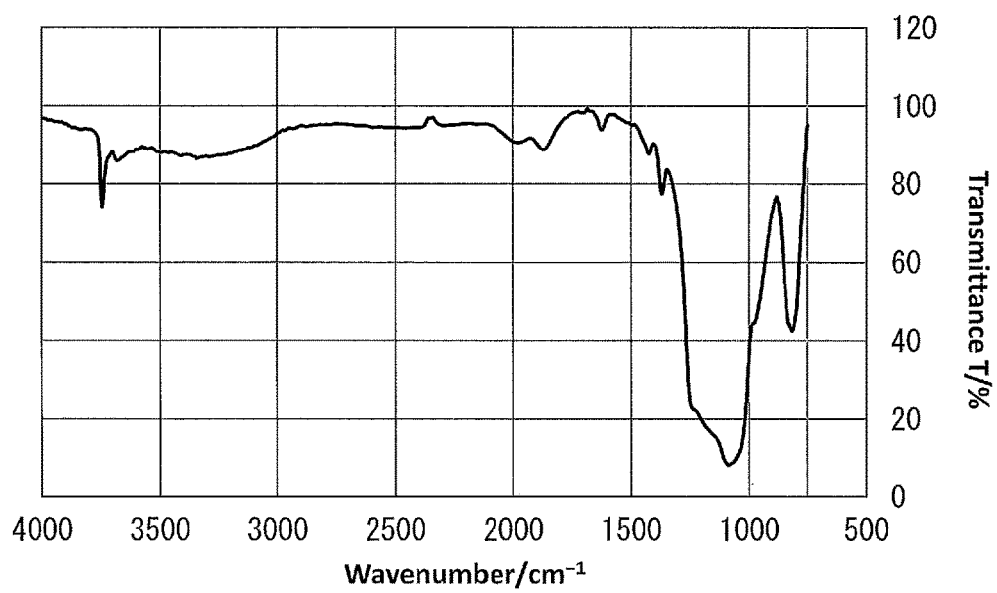
FIG. 28 shows an IR spectrum of the surface-modified silica gel fabricated in Comparative Example 1.

FIG. 28 subsequently shows the result of IR evaluation of the surface-modified silica gel fabricated in Comparative Example 1. Referring to the result of IR evaluation of the surface-modified silica gel fabricated in Example 1-6 (FIG. 8) for comparison, an absorption peak attributed to C—H stretching vibration is explicitly seen at a wavenumber of around 3000 cm$^{-1}$ for Example 1-6 in which a borane catalyst was used (FIG. 8). This suggests that efficient support of the molecular structure A was achieved. By contrast, any similar absorption peak was not observed for Comparative Example 1 in which a platinum catalyst was used (FIG. 28), and this revealed that support of the molecular structure A was not achieved almost at all.

Figure 29:
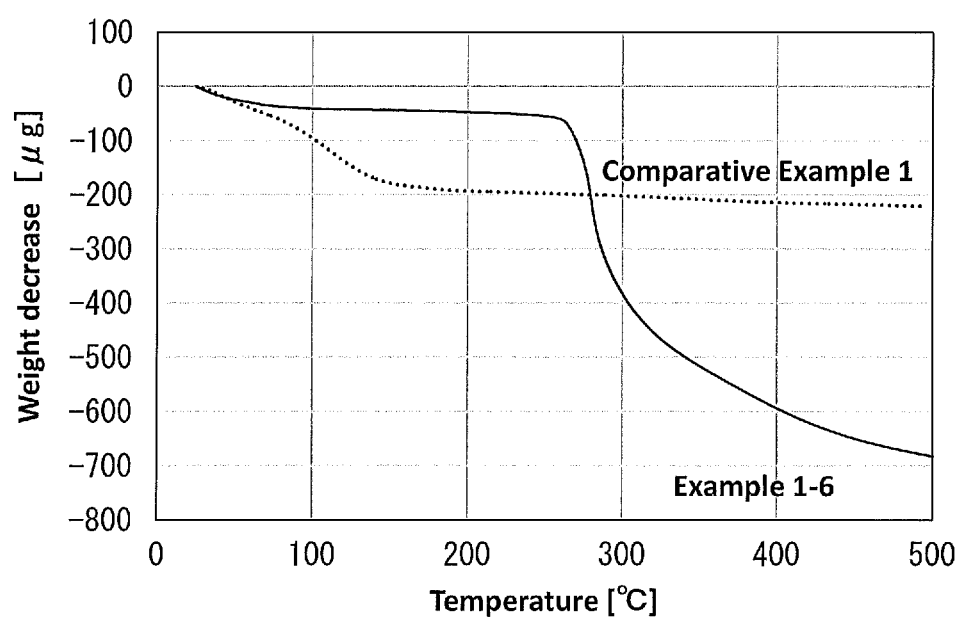
FIG. 29 shows the results of thermogravimetry of the surface-modified silica gel fabricated in Comparative Example 1 and the surface-modified silica gel fabricated in Example 1-6.

Next, a 5 mg fraction was sampled from each of the surface-modified silica gels fabricated in Comparative Example 1 and Example 1-6, and the decrease in weight of each fraction caused by a temperature rise to 500° C. was evaluated using a thermogravimetric apparatus (TG/DTA 7200, manufactured by SII NanoTechnology Inc.). The temperature rise was controlled as follows: the temperature was raised from 25° C. at a rate of 10° C. per 1 minute; upon reaching 200° C., the temperature was kept at 200° C. for 10 minutes; after that, the temperature was further raised at a rate of 10° C. per 1 minute; and upon reaching 500° C., the temperature was kept at 500° C. for 10 minutes. The results of evaluation are shown in FIG. 29. As for the weight decrease occurring after the temperature reached around 260° C. above which organic functional groups undergo burning, a decrease of about 650 µg was observed for Example 1-6, while almost no decrease was observed for Comparative Example 1, as shown in FIG. 29. That is, it was confirmed that modification of the surface of the silica gel with the molecular structure A was not achieved almost at all in Comparative Example 1.

Comparative Example 2

Reaction Between Triethylsilanol and Hydrosilane Compound

What was attempted in Comparative Example 2 was a reaction between a hydrosilane compound and the triethylsilanol molecule having a Si—OH group, rather than the use of a hydrosilane compound for modification of the surface of a base material. Specifically, it was attempted to allow a reaction to take place between two compounds in the same manner as in Examples 1, except that (3-aminopropyl) dimethylsilane as prepared in Production Example 8 was used as the hydrosilane compound, and that triethylsilanol was used instead of a silica gel in an equivalent amount relative to the hydrosilane compound. However, the intended reaction did not take place, and the raw materials were recovered as such. This was presumably because in the so-called homogeneous reaction between low-molecular substances, amino groups coordinated with and poisoned the borane catalyst, causing reduction in the catalytic ability of the borane catalyst. In Example 1-10, by contrast, modification of the surface of a silica gel with (3-aminopropyl) dimethylsilane was achieved. This was presumably because the presence of OH groups on the surface of the base material lead to formation of a huge number of ion pairs of the OH groups and amino groups, thus preventing the amino groups from acting as a catalyst poison. The result for Comparative Example 2 confirmed that modification of the surface of a base material and a reaction in a homogeneous system show entirely different behaviors in terms of reactivity.

Example 2

Use as Atom-Transfer Radical Polymerization (ATRP) Agent (Preparation of Hydrosilane Compound Having Molecular Structure a Functioning as ATRP Agent)

An amount of 1.00 equivalent of 4-dimethylsilylbutanol (265 mg, 2.00 mmol), 1.05 equivalents of triethylamine (0.293 mL, 2.1 mmol), and 1.60 mL of dichloromethane as a solvent were placed and stirred in a well-dried Schlenk tube (with an internal volume of 20 mL) under nitrogen atmosphere at room temperature. Besides this, 1.05 equivalents of 2-bromoisobutyryl bromide (0.258 mL, 2.1 mmol) was placed in a well-dried eggplant-shaped flask (with an internal volume of 30 mL) under nitrogen atmosphere at room temperature, and 8.00 mL of dichloromethane as solvent was added, followed by stirring. Next, the above Schlenk tube was cooled to 0° C., and the solution of 2-bromoisobutyl bromide contained in the eggplant-shaped flask was then added dropwise, followed by stirring at room temperature for 12 hours. Next, extraction with dichloromethane was performed, and the organic layer was washed with brine. Subsequently, the resulting extract was dehydrated with anhydrous Na$_2$SO$_4$ and filtered, and then the filtrate was concentrated using an evaporator and vacuum-dried. The resulting crude product was then purified by silica gel column chromatography (developing solvent: hexane/AcOEt=10/1 (volume ratio), Rf value=0.6) to obtain 500 mg (1.78 mmol) of (4-dimethylsilyl)butyl 2-bromo-2-methylpropionate in an isolated yield of 89%. The reaction formula for the reaction is shown below. As represented by the reaction formula, the hydrosilane compound prepared has a molecular structure A functioning as an ATRP agent, and the molecular structure A has a carbonyl group.

[Chemical Formula 24]

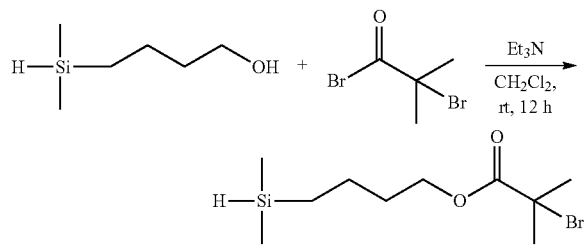

The (4-dimethylsilyl)butyl 2-bromo-2-methylpropionate obtained was identified by $^1$H-NMR measurement. The chemical shifts determined were as follows.

δ (ppm): 0.073 (d, J=3.6 Hz, 6H), 0.597-0.646 (m, 2H), 1.424-1.503 (m, 2H), 1.691-1.761 (m, 2H), 1.934 (s, 6H), 3.825-3.879 (m, 1H), 4.170-4.202 (t, 2H)

Figure 30:
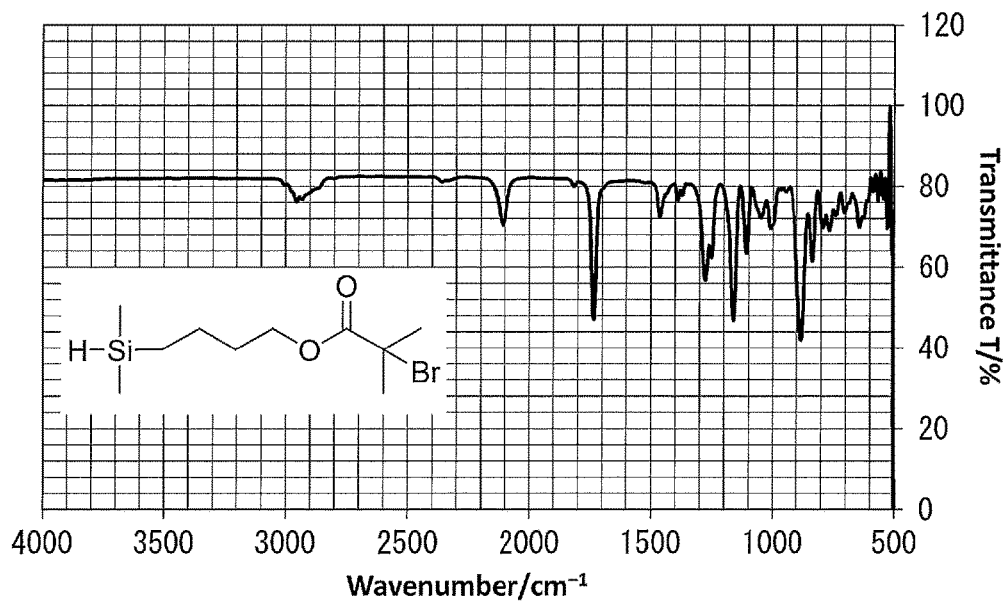
FIG. 30 shows an IR spectrum of a hydrosilane compound prepared in Example 2.

Identification of the (4-dimethylsilyl)butyl 2-bromo-2-methylpropionate obtained was performed also by IR measurement. The IR spectrum obtained is shown in FIG. 30.

(Modification of Surface of Silica Gel)

An amount of 1 equivalent of a silica gel (MCM-41, 100 mg) was placed in a Schlenk tube (with an internal volume of 20 mL), vacuum-dried at 180° C. for 4 hours, and then further dried using a heat gun. Next, the dried silica gel was cooled to room temperature, and CH$_2$Cl$_2$ (3.0 mL) was then added under nitrogen atmosphere, followed by stirring. Subsequently, 1 equivalent of (4-dimethylsilyl)butyl 2-bromo-2-methylpropionate (141 mg, 0.5 mmol) was added dropwise under stirring inside the Schlenk tube. Next, B(C$_6$F$_5$)$_3$ (2.56 mg, 1 mol %) was quickly added, followed by standing at room temperature, during which evolution of hydrogen continued for 5 minutes. After confirmation of cessation of the evolution of hydrogen, the contents of the Schlenk tube were filtered using CH$_2$Cl$_2$, and the collected solid was vacuum-dried. In this way, a silica gel having its surface modified (functionalized) with the molecular structure A of the hydrosilane compound was obtained.

The reaction formula for the reaction is shown below.

[Chemical Formula 25]

MCM-41 +

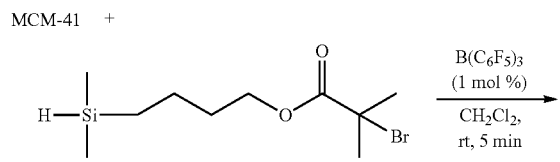

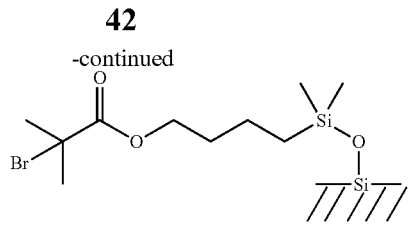

Figure 31:
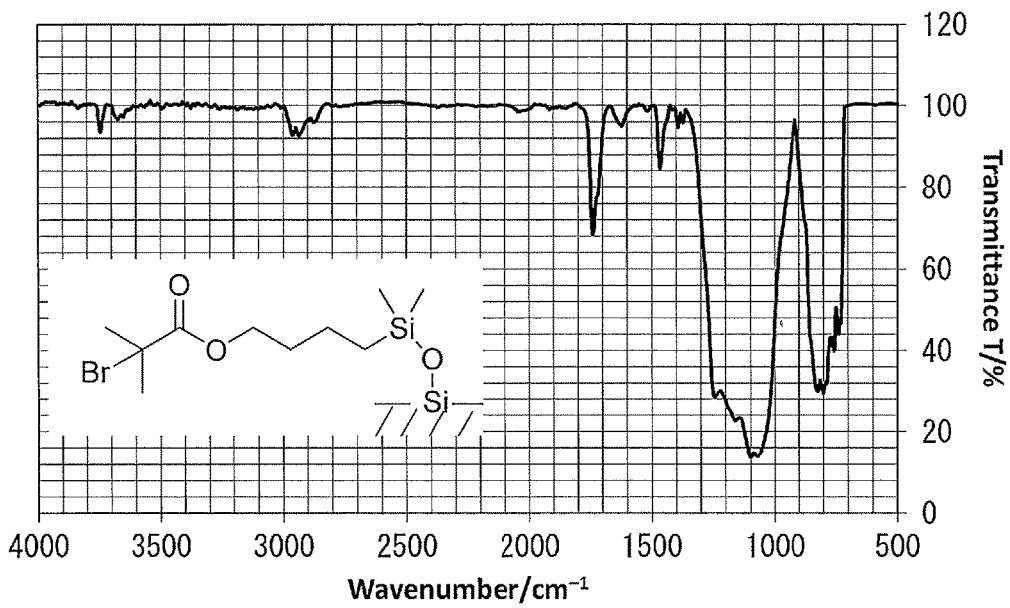
FIG. 31 shows an IR spectrum of a surface-modified silica gel fabricated in Example 2.

The result of IR evaluation of the obtained surface-modified silica gel is shown in FIG. 31. The IR profile shown in FIG. 31 confirms that modification of the surface of the silica gel with the molecular structure A of the hydrosilane compound was achieved. The carbonyl group in the molecular structure A remained as such, which confirmed that the Si—H group of the hydrosilane compound selectively reacted with the Si—OH group of the silica gel as a base material, rather than with the carbonyl group.

(Reaction as ATRP Agent)

CuBr (2.75 mg, 0.0192 mmol) and a styrene monomer (0.687 mL, 6 mmol) were placed in a well-dried Schlenk tube (with an internal volume of 20 mL), and 0.825 mL of anisole as a solvent was added at room temperature under nitrogen atmosphere, followed by stirring. Next, N,N,N',N",N"-pentamethylethylenetriamine (PMDETA, 8.07 μL, 0.0384 mmol) was added dropwise, followed by a temperature rise to 100° C. and then by stirring to make the reaction system homogeneous. Besides this, the surface-modified silica gel fabricated as above was placed in a well-dried Schlenk tube (with an internal volume of 20 mL) at room temperature, the tube was purged with nitrogen and, under the nitrogen atmosphere, the liquid mixture of CuBr and the styrene monomer prepared as above was added dropwise with a cannula. Subsequently, ethyl 2-bromo-2-methylpropionate (1.23 μL, 0.0084 mmol) was added dropwise under stirring, then the resulting mixed solution was raised in temperature to 100° C. and further stirred for 12 hours. After the lapse of 12 hours, centrifugation was repeated four times using dichloromethane, and the resulting solid was vacuum-dried. The reaction formula for the reaction is shown below.

[Chemical Formula 26]

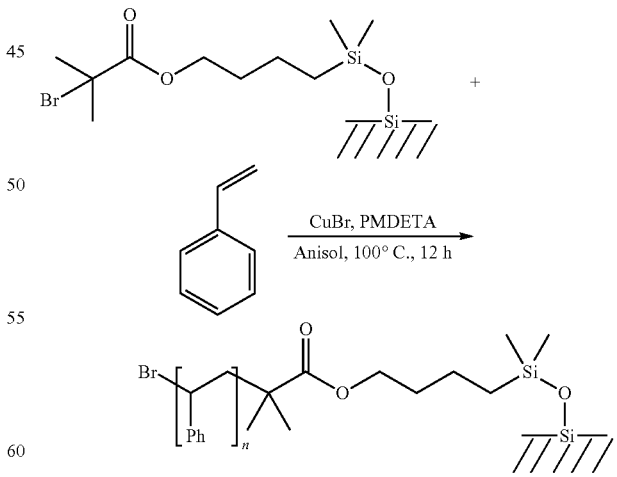

Figure 32:
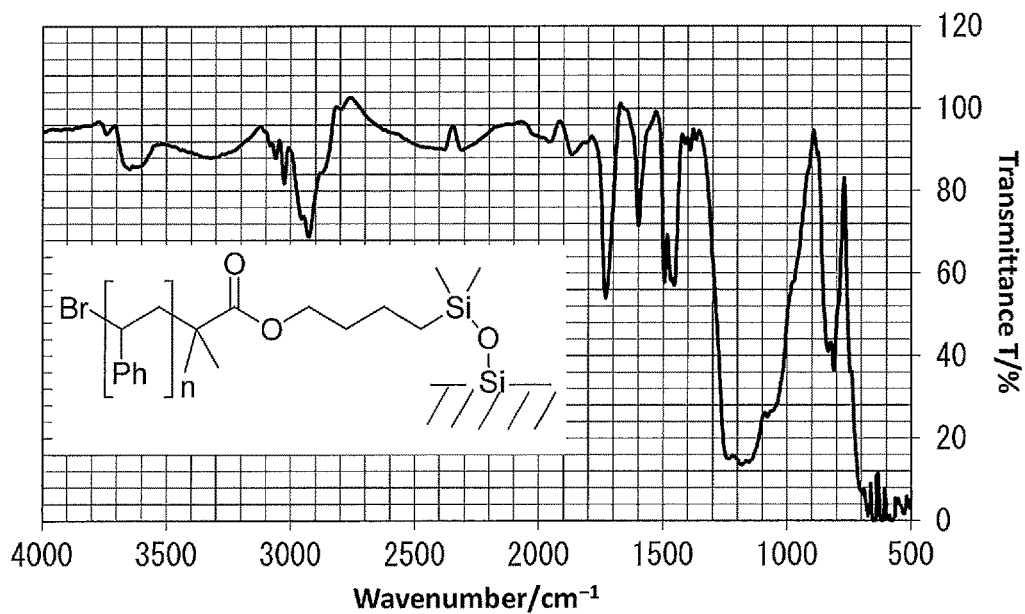
FIG. 32 shows an IR spectrum of the surface-modified silica gel fabricated in Example 2 that had been subjected to a polymerization reaction using the surface-modifying portion of the gel as an atom-transfer radical polymerization (ATRP) agent.

The result of IR evaluation of the obtained surface-modified silica gel is shown in FIG. 32. The IR profile shown in FIG. 32 confirms that the modification shown in the right-hand side of the reaction formula was accomplished on the surface of the silica gel.

Example 3

Surface Modification with Molecular Structure a Containing Acrylate Structure (Preparation of Hydrosilane Compound)

An amount of 1.00 equivalent of 4-dimethylsilylbutanol (265 mg, 2.00 mmol), 1.05 equivalents of triethylamine (0.293 mL, 2.1 mmol), and 1.60 mL of dichloromethane as a solvent were placed and stirred in a well-dried Schlenk tube (with an internal volume of 20 mL) under nitrogen atmosphere at room temperature. Besides this, 1.05 equivalents of acryloyl chloride (0.170 mL, 2.1 mmol) was placed in a well-dried eggplant-shaped flask (with an internal volume of 30 mL) under nitrogen atmosphere at room temperature, and 8.00 mL of dichloromethane as a solvent was added, followed by stirring. Next, the above Schlenk tube was cooled to 0° C., and the solution of acryloyl chloride contained in the eggplant-shaped flask was then added dropwise, followed by stirring at room temperature for 12 hours. Next, extraction with dichloromethane was performed, and the organic layer was washed with brine. Subsequently, the resulting extract was dehydrated with anhydrous $Na_2SO_4$ and filtered, and then the filtrate was concentrated using an evaporator and vacuum-dried. The resulting crude product was then purified by silica gel column chromatography (developing solvent: chloroform, Rf value=0.7) to obtain 150 mg (0.805 mmol) of (4-dimethylsilyl)butyl acrylate in an isolated yield of 40%. The reaction formula for the reaction is shown below.

[Chemical Formula 27]

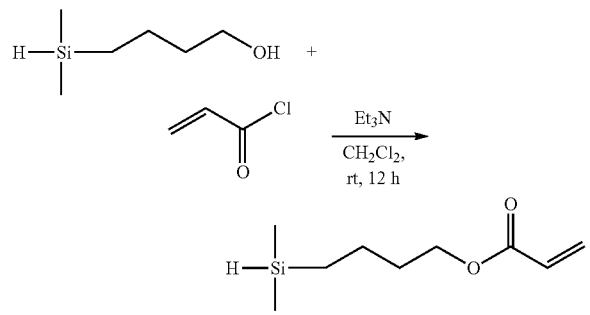

The (4-dimethylsilyl)butyl acrylate obtained was identified by $^1$H-NMR measurement. The chemical shifts determined were as follows.

δ (ppm): 0.073 (d, J=3.6 Hz, 6H), 0.596-0.645 (m, 2H), 1.419-1.403 (m, 2H), 1.676-1.747 (m, 2H), 3.823-3.875 (m, 1H), 4.147-4.180 (t, 2H), 5.806-5.836 (q, 1H), 6.091-6.160 (q, 1H), 6.379-6.426 (q, 1H)

Figure 33:
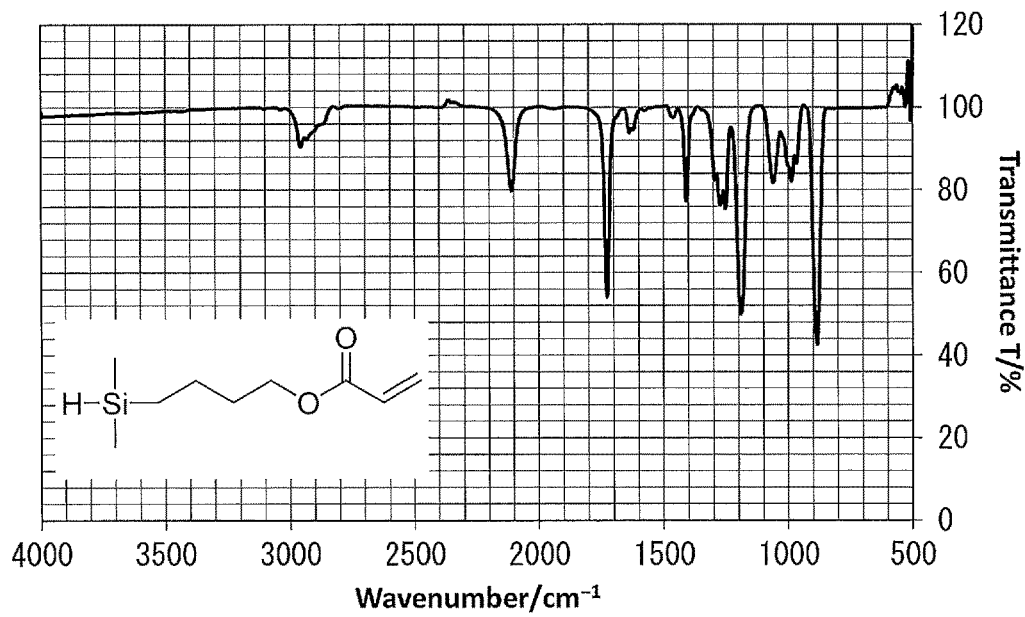
FIG. 33 shows an IR spectrum of a hydrosilane compound prepared in Example 3.

Identification of the obtained (4-dimethylsilyl)butyl acrylate was performed also by IR measurement. The IR spectrum obtained is shown in FIG. 33.

(Modification of Surface of Silica Gel)

An amount of 1 equivalent of silica gel (MCM-41, 100 mg) was placed in a Schlenk tube (with an internal volume of 20 mL), vacuum-dried at 180° C. for 4 hours, and then further dried using a heat gun. Next, the dried silica gel was cooled to room temperature, and $CH_2Cl_2$ (3.0 mL) was then added under nitrogen atmosphere, followed by stirring. Subsequently, 1 equivalent of (4-dimethylsilyl)butyl acrylate (93.2 mg, 0.5 mmol) was added dropwise under stirring inside the Schlenk tube. Next, $B(C_6F_5)_3$ (2.56 mg, 1 mol %) was quickly added, followed by standing at room temperature, during which evolution of hydrogen continued for 5 minutes. After confirmation of cessation of the evolution of hydrogen, the contents of the Schlenk tube were filtered using $CH_2Cl_2$, and the collected solid was vacuum-dried. In this way, a silica gel having its surface modified (functionalized) with the molecular structure A of the hydrosilane compound was obtained.

The reaction formula for the reaction is shown below.

[Chemical Formula 28]

MCM-41 +

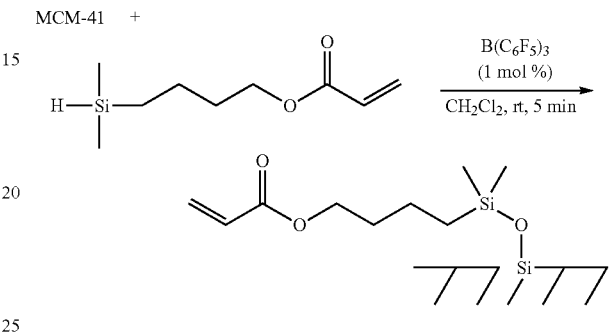

Figure 34:
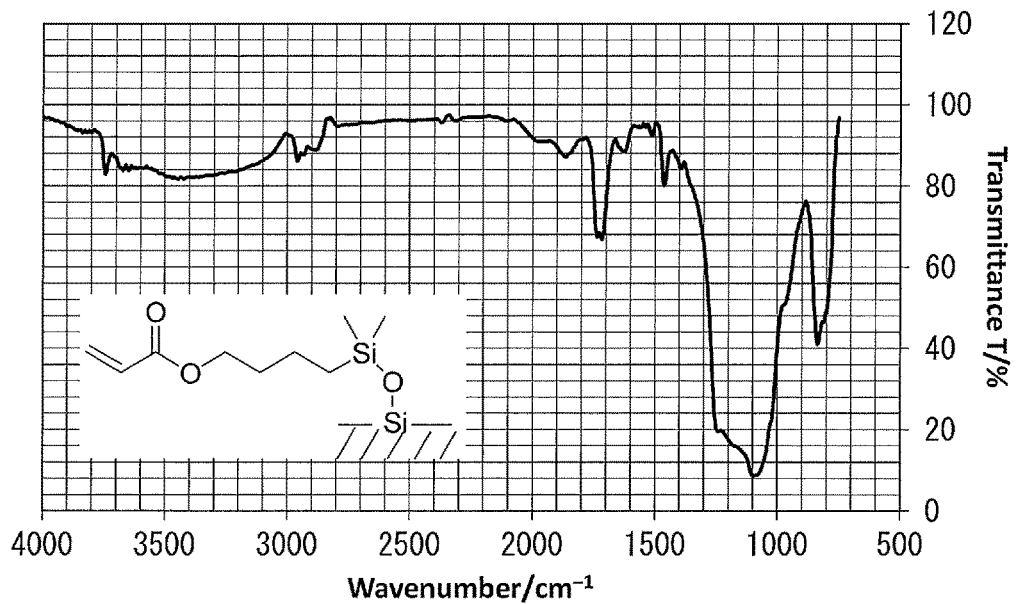
FIG. 34 shows an IR spectrum of a surface-modified silica gel fabricated in Example 3.

The result of IR evaluation of the obtained surface-modified silica gel is shown in FIG. 34. The IR profile shown in FIG. 34 confirms that modification of the surface of the silica gel with the molecular structure A of the hydrosilane compound was achieved.

Example 4

Use as Reversible Addition-Fragmentation Chain Transfer Polymerization (RAFT) Agent (Preparation of Hydrosilane Compound Having Molecular Structure a Functioning as RAFT Agent)

3-mercaptopropyldimethylsilane (402.94 mg, 3 mmol) as prepared in Production Example 18 and carbon disulfide (456.84 mg, 6 mmol) were dissolved in $CHCl_3$ (2 mL) under nitrogen atmosphere, and triethylamine (607.14 mg, 6 mmol) was added dropwise at room temperature, followed by stirring for 3 hours. Next, (1-bromoethyl)benzene (555.18 mg, 3 mmol) was added dropwise at room temperature, followed by stirring for 20 hours. Completion of the reaction was followed by addition of an aqueous hydrochloric acid solution (with a concentration of 10 weight %) and liquid-liquid separation using $CHCl_3$. The organic layer collected was washed with brine, dried over $Na_2SO_4$, and filtered, followed by concentration to obtain a crude product. The crude product obtained was purified by silica gel flash column chromatography to obtain 878.5 mg of 3-dimethylhydrosilylpropyl-1-phenylethyl trithiocarbonate in a yield of 93%. The reaction formula for the reaction is shown below. As represented by the reaction formula, the hydrosilane compound prepared has a molecular structure A functioning as a RAFT agent.

[Chemical Formula 29]

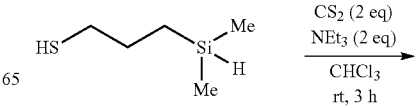

-continued

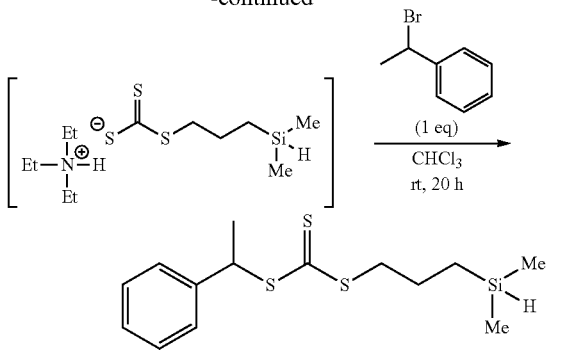

The 3-dimethylhydrosilylpropyl-1-phenylethyl trithiocarbonate obtained was identified by $^1$H-NMR measurement. The chemical shifts determined were as follows.

δ (ppm): 0.073 (d, J=3.6 Hz, 6H), 0.722-0.671 (m, 2H), 1.687-1.764 (m, 5H), 3.357 (t, 2H), 3.869-3.834 (m, 1H), 5.333 (q, 1H), 7.396-7.282 (m, 5H)

Figure 35:
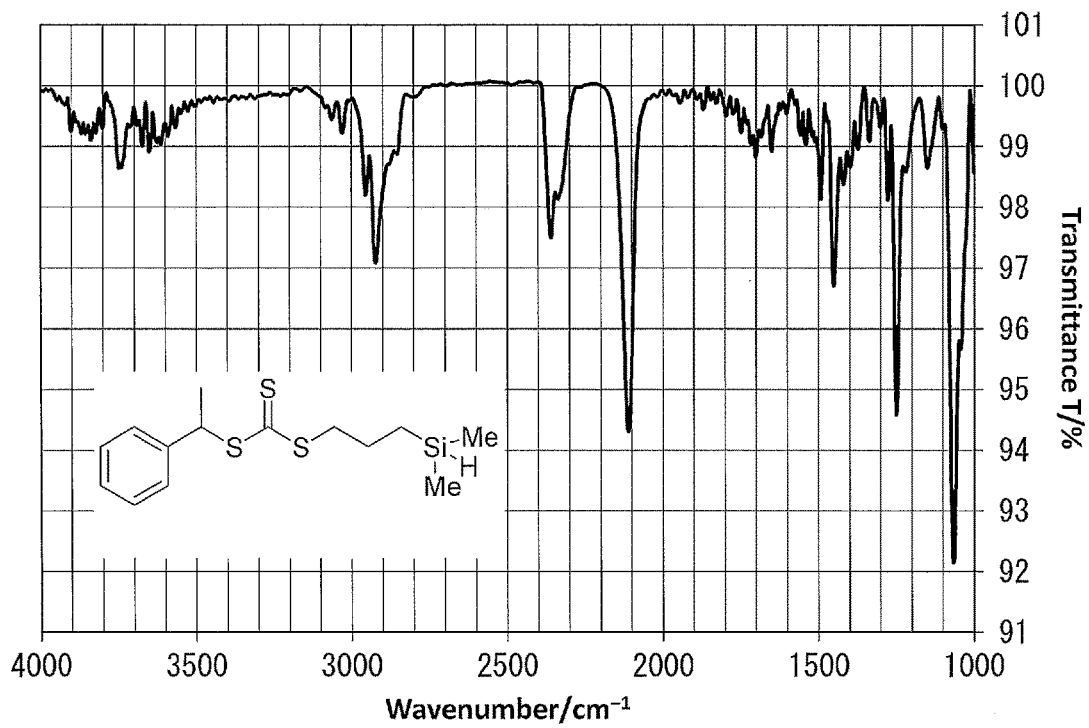
FIG. 35 shows an IR spectrum of a hydrosilane compound prepared in Example 4.

Identification of the obtained 3-dimethylhydrosilylpropyl-1-phenylethyl trithiocarbonate was performed also by IR measurement. The IR spectrum obtained is shown in FIG. 35.

(Modification of Surface of Silica Gel)

An amount of 1 equivalent of a silica gel (MCM-41, 80 mg) was placed in a Schlenk tube (with an internal volume of 20 mL), vacuum-dried at 180° C. for 4 hours, and then further dried using a heat gun. Next, the dried silica gel was cooled to room temperature, and CH$_2$Cl$_2$(2.4 mL) was then added under nitrogen atmosphere, followed by stirring. Subsequently, 1 equivalent of 3-dimethylhydrosilylpropyl-1-phenylethyl trithiocarbonate (126 mg, 0.4 mmol) was added dropwise under stirring inside the Schlenk tube. Next, B(C$_6$F$_5$)$_3$(2.05 mg, 1 mol %) was quickly added, followed by standing at room temperature, during which evolution of hydrogen continued for 5 minutes. After confirmation of cessation of the evolution of hydrogen, the contents of the Schlenk tube were filtered using CH$_2$Cl$_2$, and the collected solid was vacuum-dried. In this way, a silica gel having its surface modified (functionalized) with the molecular structure A of the hydrosilane compound was obtained.

The reaction formula for the reaction is shown below.

[Chemical Formula 30]

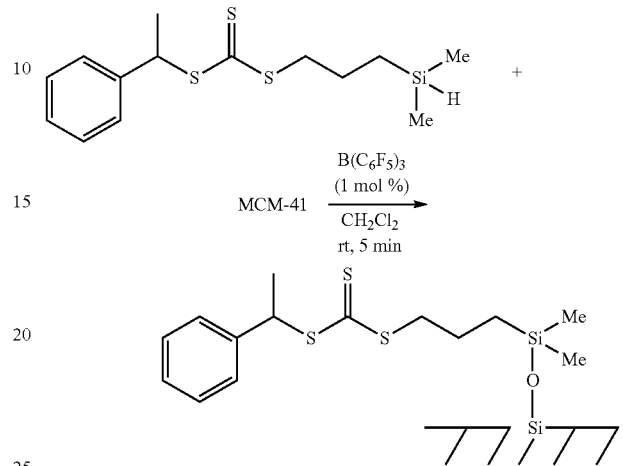

Figure 36:
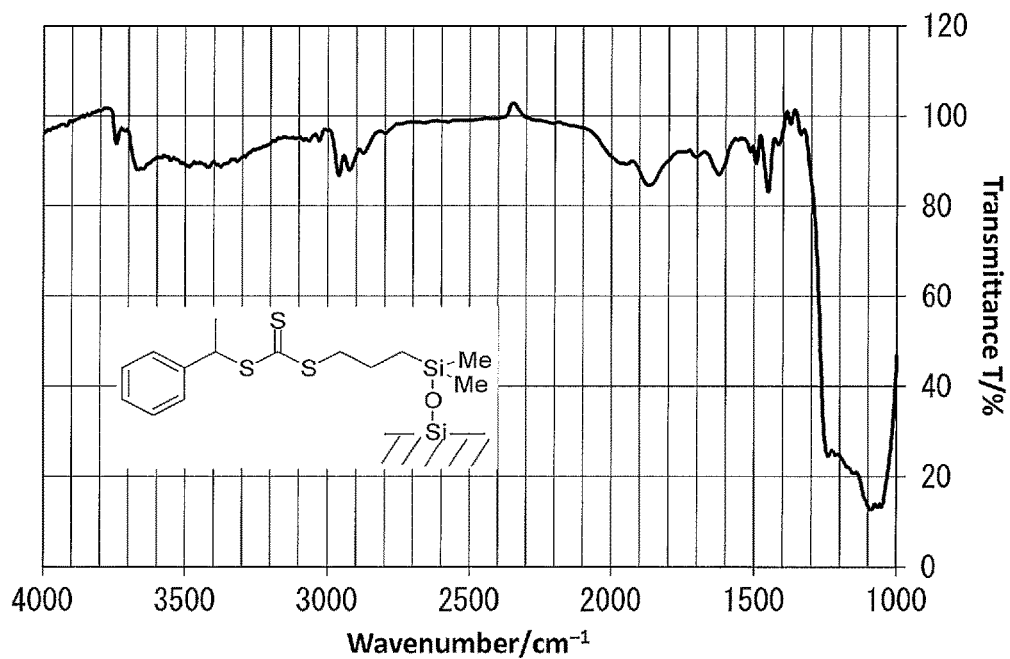
FIG. 36 shows an IR spectrum of a surface-modified silica gel fabricated in Example 4.

The result of IR evaluation of the obtained surface-modified silica gel is shown in FIG. 36. The IR profile shown in FIG. 36 confirms that modification of the surface of the silica gel with the molecular structure A of the hydrosilane compound was achieved.

(Reaction as RAFT Agent)

The surface-modified silica gel (40 mg) fabricated as above, n-butyl acrylate (1026 mg), and azobisisobutyronitrile (1 mg) were mixed with 1,4-dioxane, followed by stirring at 70° C. for 16 hours. This was followed by centrifugation using CH$_2$Cl$_2$, and the resulting silica gel was washed four times. The reaction formula for the reaction is shown below.

[Chemical Formula 31]

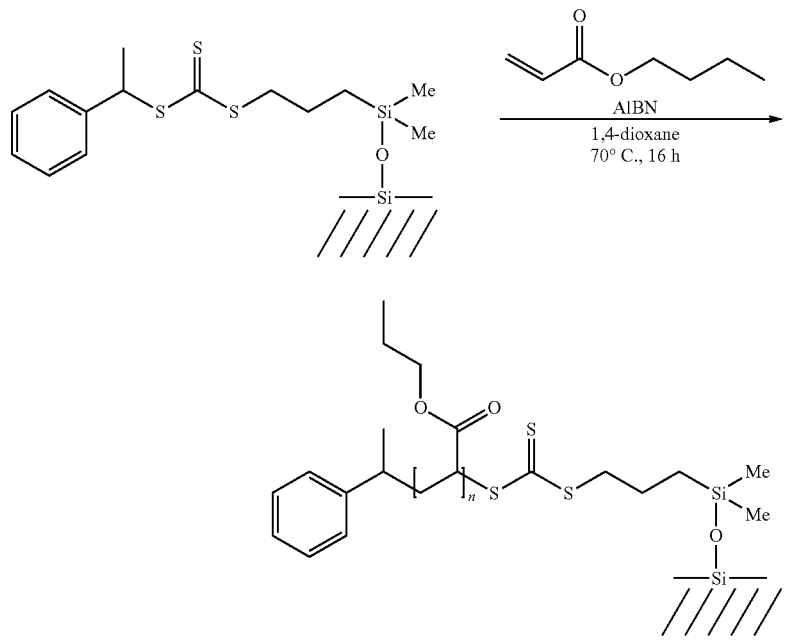

Figure 37:
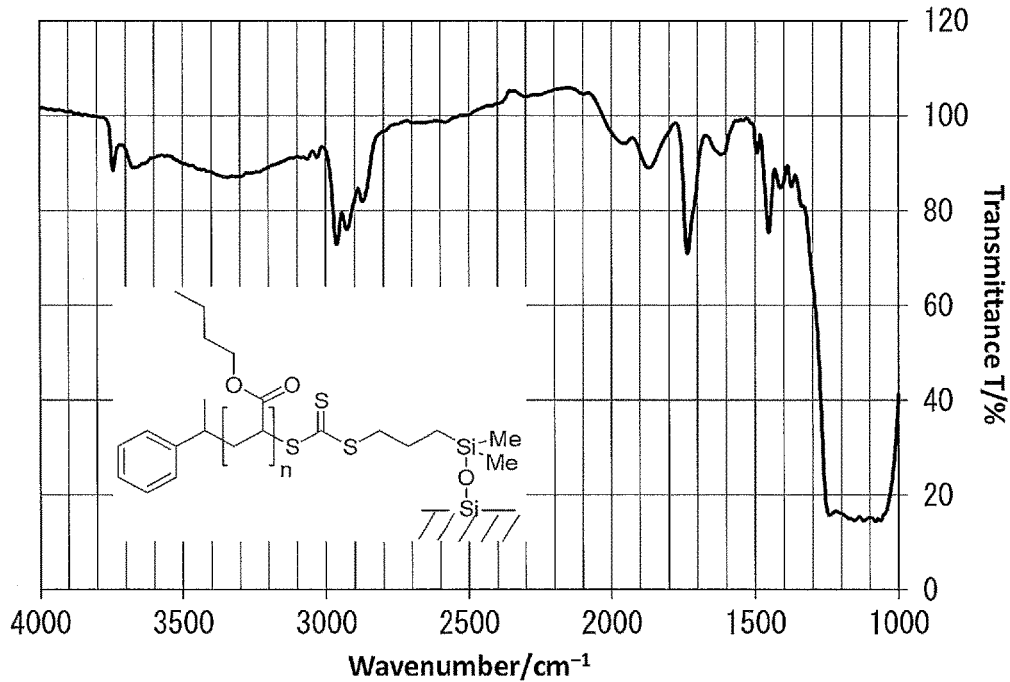
FIG. 37 shows an IR spectrum of the surface-modified silica gel fabricated in Example 4 that had been subjected to a polymerization reaction using the surface-modifying portion of the gel as a reversible addition-fragmentation chain transfer polymerization (RAFT) agent.
Figure 38:
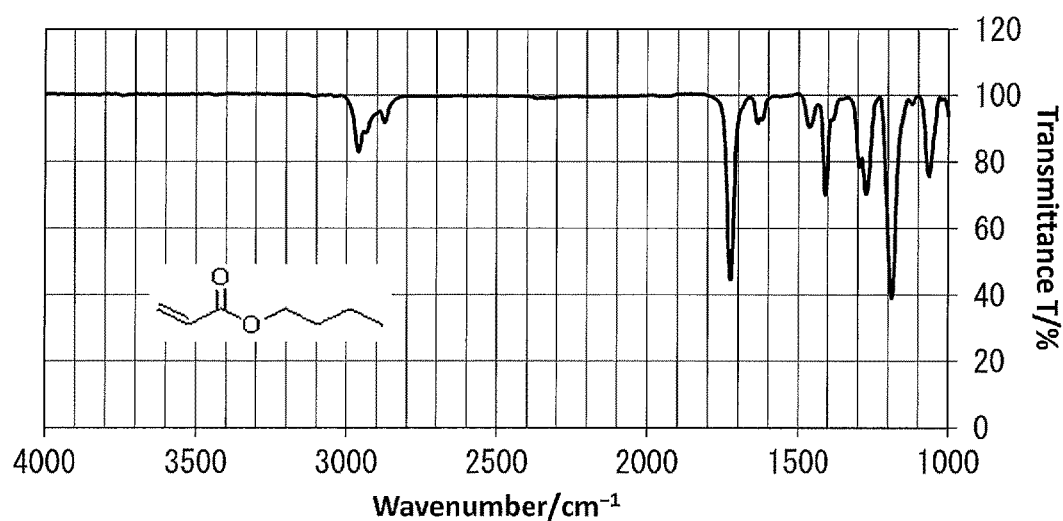
FIG. 38 shows an IR profile of n-butyl acrylate used in Example 4.

The result of IR evaluation of the obtained surface-modified silica gel is shown in FIG. 37. The IR profile shown in FIG. 37 confirms that the modification shown in the right-hand side of the reaction formula was accomplished on the surface of the silica gel. An IR profile of n-butyl acrylate is also shown in FIG. 38.

Example 5

Modification of Surface of Paper

In Example 5, paper (manufactured by NIPPON PAPER CRECIA CO., LTD., Kimwipes) was used as the base material, and the surface of the paper was modified with the molecular structure A of a hydrosilane compound.

Example 5-1

Figure 39:
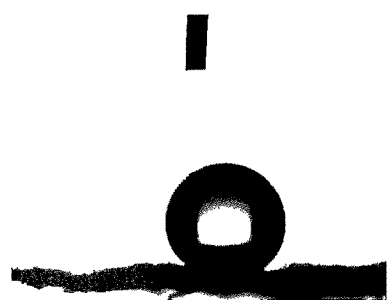
FIG. 39 shows how a water droplet contacts the principal surface of surface-modified paper fabricated in Example 5-1.

Kimwipes was cut into a piece having a principal surface with an area of 1.2 cm$^2$, and the piece of Kimwipes was immersed in a liquid mixture of polymethylhydrosiloxane (PMHS, 100 mg, 0.02 mmol), B(C$_6$F$_5$)$_3$(10 mg, 0.02 mmol), and anhydrous methylene chloride (manufactured by Sigma-Aldrich Co. LLC., 1 mL) under nitrogen atmosphere, and allowed to stand at room temperature for 5 minutes. Hydrogen was evolved upon the immersion, and the evolution of hydrogen ceased to be observed within the lapse of 5 minutes. After standing, the Kimwipes was taken out of the liquid mixture, washed with methylene chloride, and dried. The contact angle of water on the principal surface of the obtained Kimwipes was then evaluated using a wettability evaluation system (manufactured by NiCK Corporation, LSE-ME 1), and the contact angle was determined to be 136° (the contact angle measurement in Examples described hereinafter was performed in the same manner). FIG. 39 shows how the contact angle was formed on the principal surface of the surface-modified Kimwipes.

Example 5-2

Kimwipes surface-modified with the molecular structure A of PMHS was obtained in the same manner as in Example 5-1, except that the immersion of Kimwipes was performed under air. The contact angle of water on the principal surface of the obtained Kimwipes was 138°.

Example 5-3

Kimwipes surface-modified with the molecular structure A of PMHS was obtained in the same manner as in Example 5-2, except that the methylene chloride used in the liquid mixture was normal (non-anhydrous) methylene chloride. The contact angle of water on the principal surface of the obtained Kimwipes was 119°.

Example 5-4

Kimwipes surface-modified with the molecular structure A of PMHS was obtained in the same manner as in Example 5-2, except that the liquid mixture was prepared using anhydrous hexane (manufactured by Sigma-Aldrich Co. LLC.) instead of anhydrous methylene chloride, and that hexane was used instead of methylene chloride for the post-immersion washing. The contact angle of water on the principal surface of the obtained Kimwipes was 138°.

Example 5-5

Kimwipes surface-modified with the molecular structure A of PMHS was obtained in the same manner as in Example 5-4, except that the hexane used in the liquid mixture was normal (non-anhydrous) hexane. The contact angle of water on the principal surface of the obtained Kimwipes was 119°.

Example 5-6

Kimwipes was cut into a piece having a principal surface with an area of 3.5 cm$^2$, and the piece of Kimwipes was immersed in a liquid mixture of polymethylhydrosiloxane (PMHS, 1000 mg, 0.20 mmol), B(C$_6$F$_5$)$_3$ (10 mg, 0.02 mmol), and anhydrous methylene chloride (manufactured by Sigma-Aldrich Co. LLC., 4 mL) under nitrogen atmosphere, and allowed to stand at room temperature for 5 minutes. Hydrogen was evolved upon the immersion, and the evolution of hydrogen ceased to be observed within the lapse of 5 minutes. After standing, the Kimwipes was taken out of the liquid mixture, washed with methylene chloride, and dried. The contact angle of water on the principal surface of the obtained Kimwipes was then evaluated, and the contact angle was determined to be 134°.

In each of Examples 5-1 to 5-6, a large surface contact angle was achieved. This large contact angle was thought to be due to the principal surface of the Kimwipes being hydrophobized and rendered water-repellent as a result of modification with the molecular structure A of PHMS. As is well-known and apparent from its name, Kimwipes yet to be modified absorbs water very well.

Example 5-7

Figure 40:
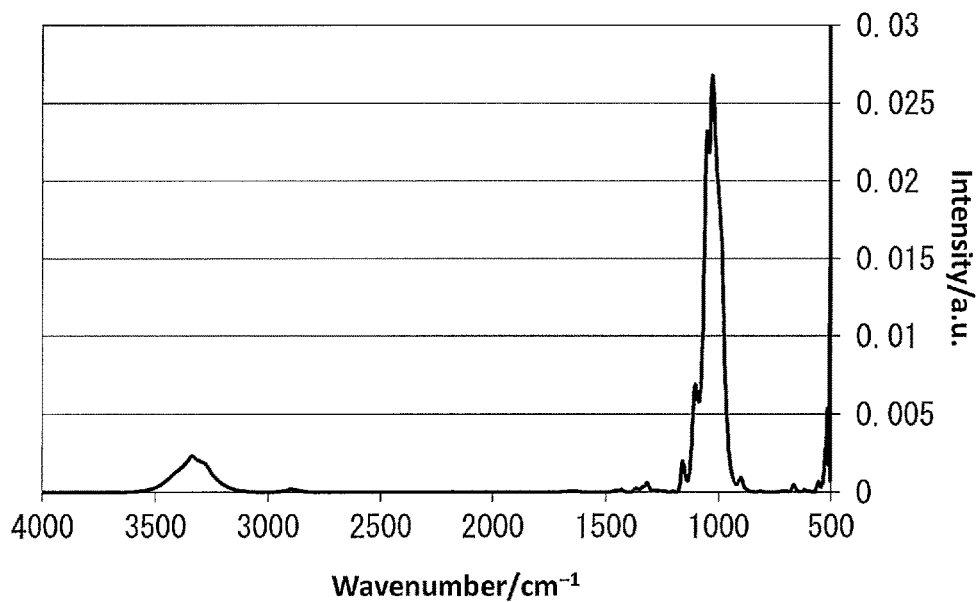
FIG. 40 shows an IR spectrum of of surface-modified paper fabricated in Example 5-7.

Kimwipes was cut into a piece having a principal surface with an area of 14 cm$^2$, and the piece of Kimwipes was immersed in a liquid mixture of polymethylhydrosiloxane (PMHS, 500 mg, 0.10 mmol), B(C$_6$F$_5$)$_3$ (5 mg, 0.01 mmol), and anhydrous methylene chloride (manufactured by Sigma-Aldrich Co. LLC., 2 mL) under nitrogen atmosphere, and allowed to stand at room temperature for 5 minutes. Hydrogen was evolved upon the immersion, and the evolution of hydrogen ceased to be observed within the lapse of 5 minutes. After standing, the Kimwipes was taken out of the liquid mixture, washed with methylene chloride, and dried to obtain surface-modified Kimwipes. The result of IR evaluation of the surface-modified Kimwipes obtained is shown in FIG. 40. As shown in FIG. 40, a strong absorption peak attributed to the Si—O—Si bond of PMHS was observed at a wavenumber of around 1000 cm$^{-1}$, which confirmed that the surface of the Kimwipes was modified with the molecular structure A derived from PMHS.

Example 6

Modification of Surface of Non-Woven Fabric

In Example 6, non-woven fabrics (manufactured by Hirose Paper Mfg Co., Ltd. and made of vinylon 1036, vinylon 1048, polyester (PET) 80, PET 100, or cotton) were used as the base material, and the surface of each non-woven fabric was modified with the molecular structure A of a hydrosilane compound.

Example 6-1

Figure 41:
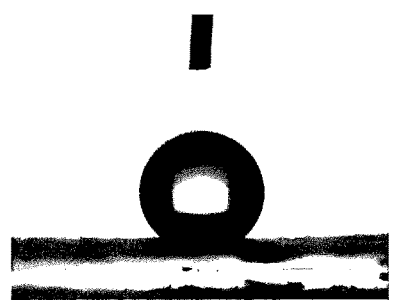
FIG. 41 shows how a water droplet contacts the principal surface of a surface-modified woven fabric fabricated in Example 6-1.

A non-woven fabric of vinylon 1036 was cut into a piece having a principal surface with an area of 1.2 cm$^2$, and the piece of non-woven fabric was immersed in a liquid mixture of polymethylhydrosiloxane (PMHS, 100 mg, 0.02 mmol), B(C$_6$F$_5$)$_3$ (10 mg, 0.02 mmol), and anhydrous methylene chloride (1 mL) under nitrogen atmosphere, and allowed to stand at room temperature for 5 minutes. Hydrogen was evolved upon the immersion, and the evolution of hydrogen gradually subsided and ceased to be observed within the lapse of 5 minutes. After standing, the non-woven fabric of vinylon 1036 was taken out of the liquid mixture, washed with methylene chloride, and dried. The contact angle of water on the principal surface of the obtained non-woven fabric of vinylon 1036 was then evaluated, and the contact angle was determined to be 136°. FIG. 41 shows how the contact angle was formed on the principal surface of the surface-modified non-woven fabric of vinylon 1036.

Figure 42:
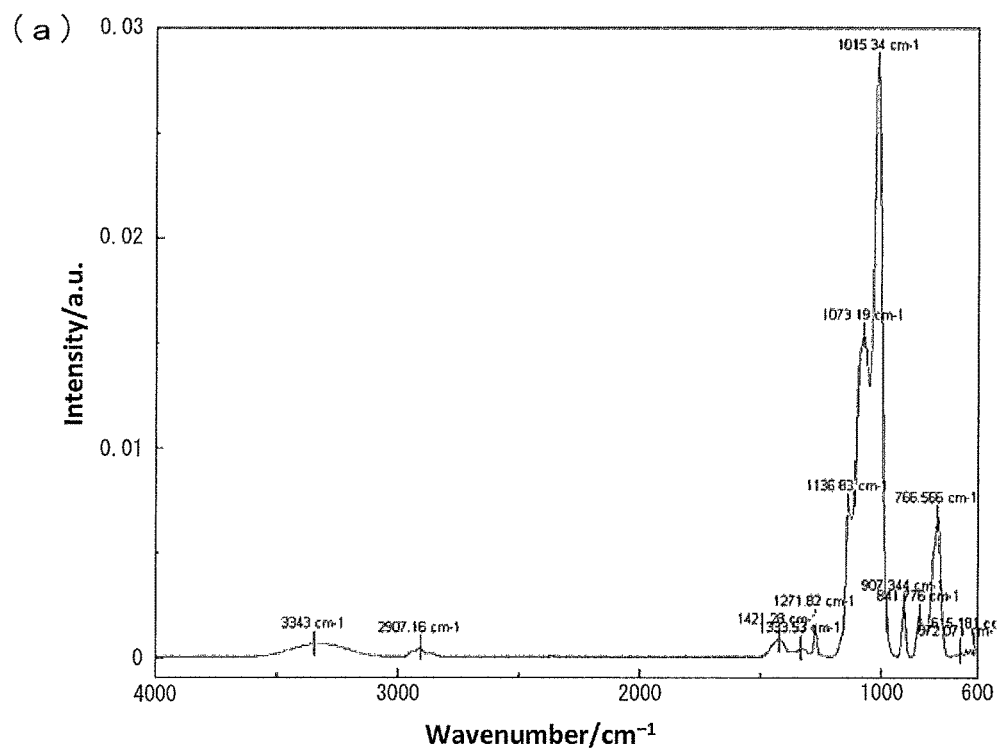
FIG. 42 shows: (a) an IR spectrum of a non-woven fabric of vinylon 1036 yet to be surface-modified; and (b) an IR spectrum of a surface-modified non-woven fabric of vinylon 1036 fabricated in Example 6-1.
Figure 42:
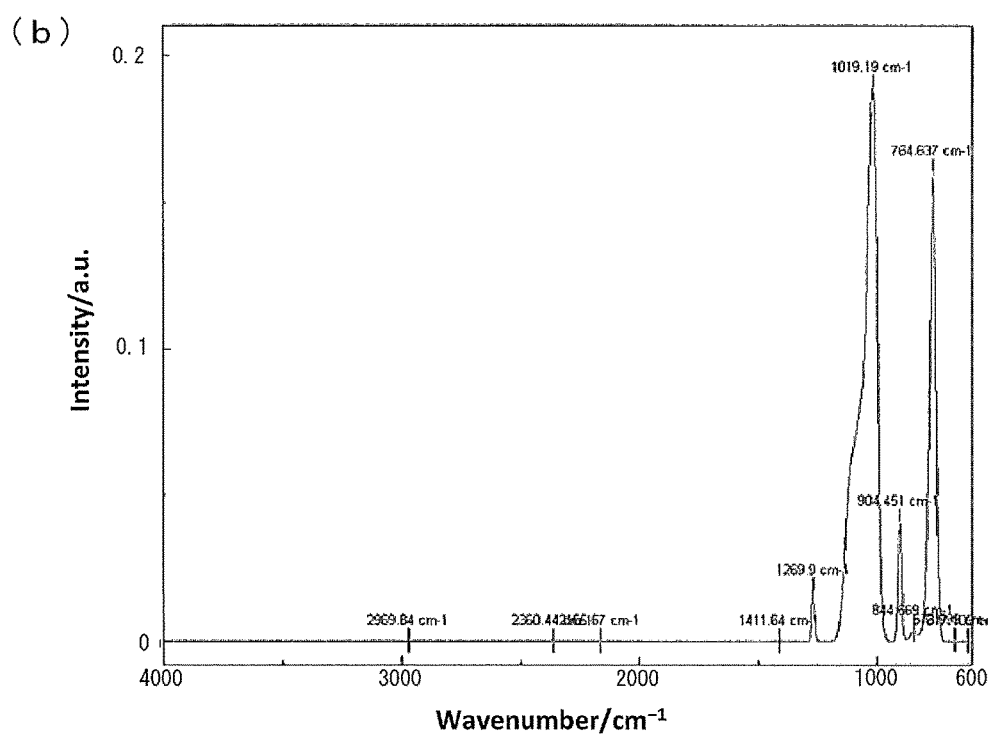

The result of IR evaluation of the non-woven fabric of vinylon 1036 that had yet to be surface-modified is shown in FIG. 42(a), while the result of IR evaluation of the surface-modified non-woven fabric of vinylon 1036 is shown in FIG. 42(b). As shown in FIG. 42(b), a peak attributed to the molecular structure A of PMHS, which was not observed before surface modification, and a change in peak shape at a wavenumber of around 1100 cm$^{-1}$ were observed for the surface-modified non-woven fabric of vinylon 1036.

Example 6-2

A non-woven fabric surface-modified with the molecular structure A of PMHS was obtained in the same manner as in Example 6-1, except that a non-woven fabric of vinylon 1048 was used instead of the non-woven fabric of vinylon 1036. The contact angle of water on the principal surface of the obtained non-woven fabric was 136°.

Figure 43:
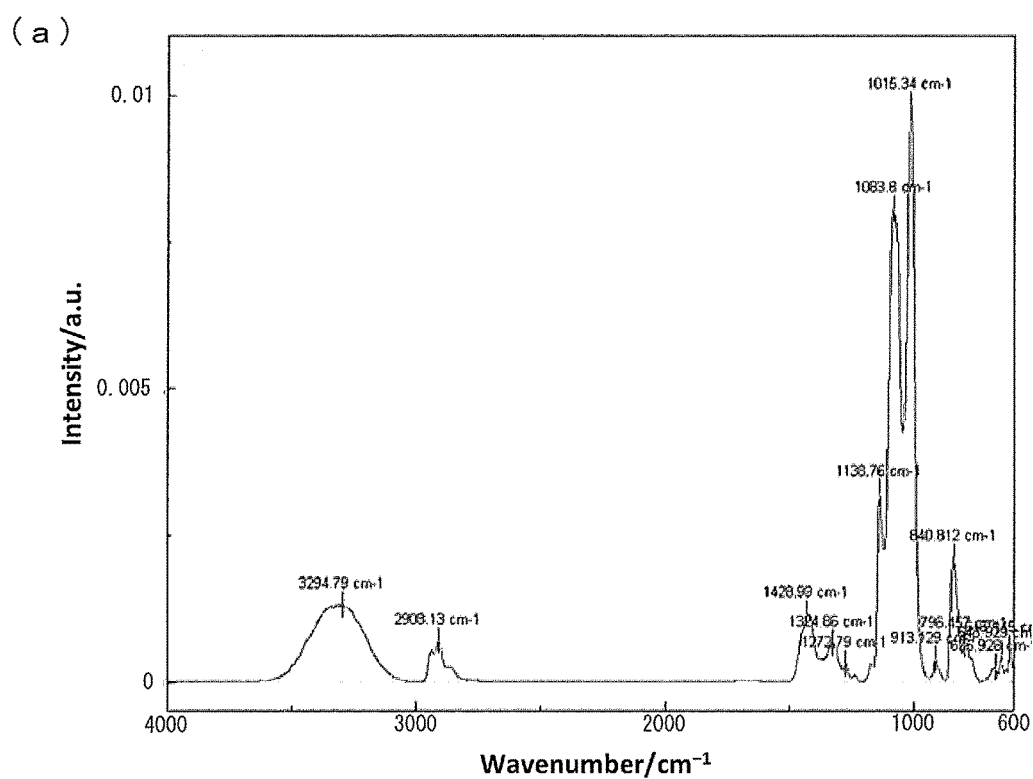
FIG. 43 shows: (a) an IR spectrum of a non-woven fabric of vinylon 1048 yet to be surface-modified; and (b) an IR spectrum of a surface-modified non-woven fabric of vinylon 1048 fabricated in Example 6-2.
Figure 43:
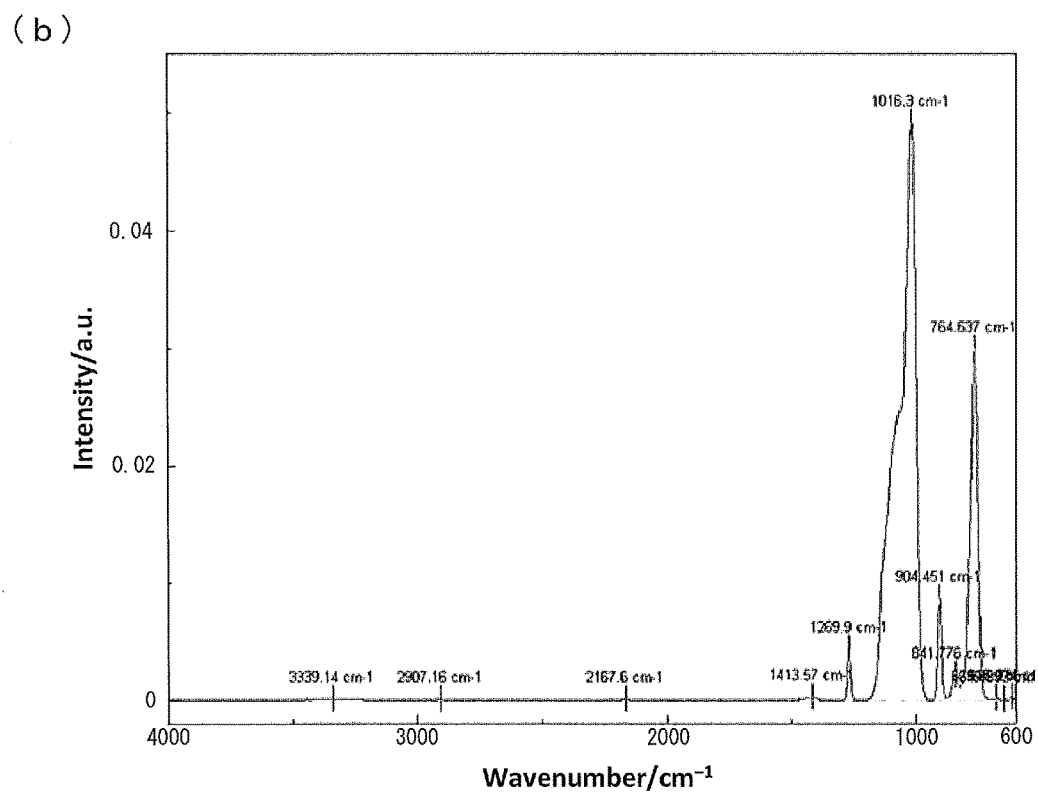

The result of IR evaluation of the non-woven fabric of vinylon 1048 that had yet to be surface-modified is shown in FIG. 43(a), while the result of IR evaluation of the surface-modified non-woven fabric of vinylon 1048 is shown in FIG. 43(b). As shown in FIG. 43(b), a peak attributed to the molecular structure A of PMHS, which was not observed before surface modification, and a change in peak shape at a wavenumber of around 1100 cm$^{-1}$ were observed for the surface-modified non-woven fabric of vinylon 1048.

Example 6-3

A non-woven fabric surface-modified with the molecular structure A of PMHS was obtained in the same manner as in Example 6-1, except that a non-woven fabric of polyester (polyethylene terephthalate: PET) 80 was used instead of the non-woven fabric of vinylon 1036. The contact angle of water on the principal surface of the obtained non-woven fabric was 132°.

Figure 44:
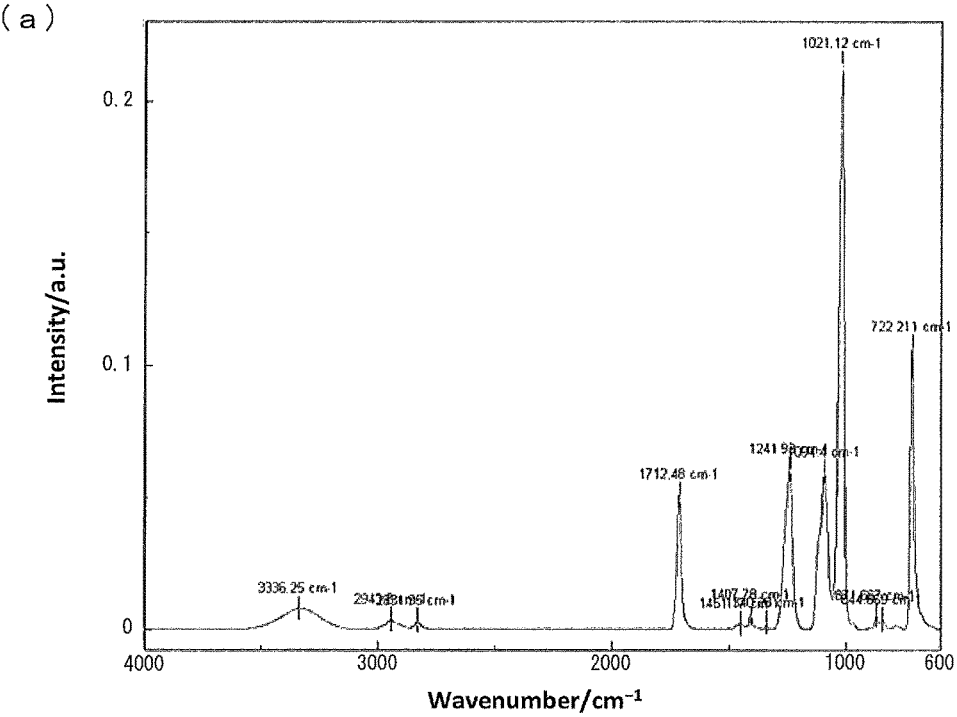
FIG. 44 shows: (a) an IR spectrum of a non-woven fabric of polyester 80 yet to be surface-modified; and (b) an IR spectrum of a surface-modified non-woven fabric of polyester 80 fabricated in Example 6-3.
Figure 44:
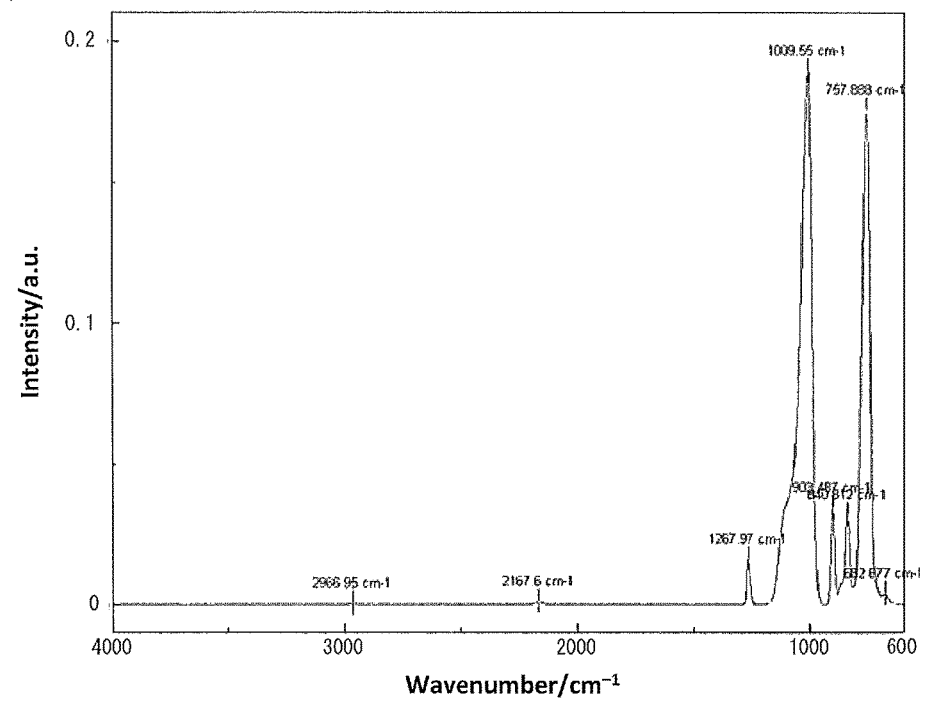

The result of IR evaluation of the non-woven fabric of PET 80 that had yet to be surface-modified is shown in FIG. 44(a), while the result of IR evaluation of the surface-modified non-woven fabric of PET 80 is shown in FIG. 44(b). As shown in FIG. 44(b), a peak attributed to the molecular structure A of PMHS, which was not observed before surface modification, and a change in peak shape at a wavenumber of around 1100 cm$^{-1}$ were observed for the surface-modified non-woven fabric of PET 80.

Example 6-4

A non-woven fabric surface-modified with the molecular structure A of PMHS was obtained in the same manner as in Example 6-1, except that a non-woven fabric of polyester 100 was used instead of the non-woven fabric of vinylon 1036. The contact angle of water on the principal surface of the obtained non-woven fabric was 136°.

Figure 45:
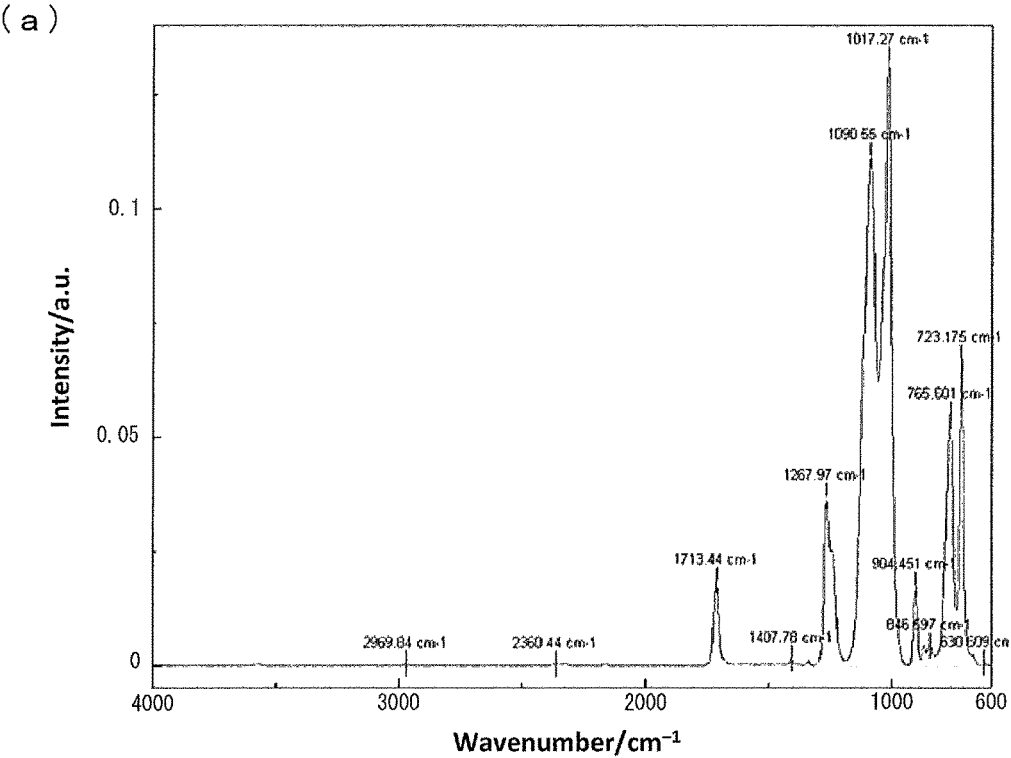
FIG. 45 shows: (a) an IR spectrum of a non-woven fabric of polyester 100 yet to be surface-modified; and (b) an IR spectrum of a surface-modified non-woven fabric of polyester 100 fabricated in Example 6-4.
Figure 45:
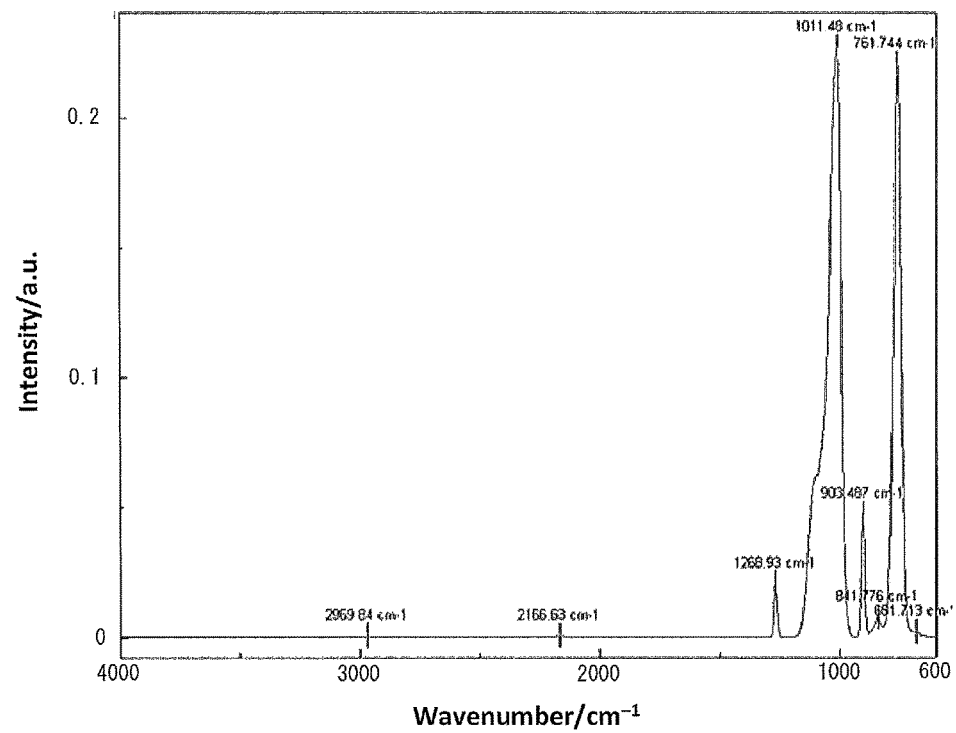

The result of IR evaluation of the non-woven fabric of PET 100 that had yet to be surface-modified is shown in FIG. 45(a), while the result of IR evaluation of the surface-modified non-woven fabric of PET 100 is shown in FIG. 45(b). As shown in FIG. 45(b), a peak attributed to the molecular structure A of PMHS, which was not observed before surface modification, and a change in peak shape at a wavenumber of around 1100 cm$^{-1}$ were observed for the surface-modified non-woven fabric of PET 100.

Example 6-5

Figure 46:
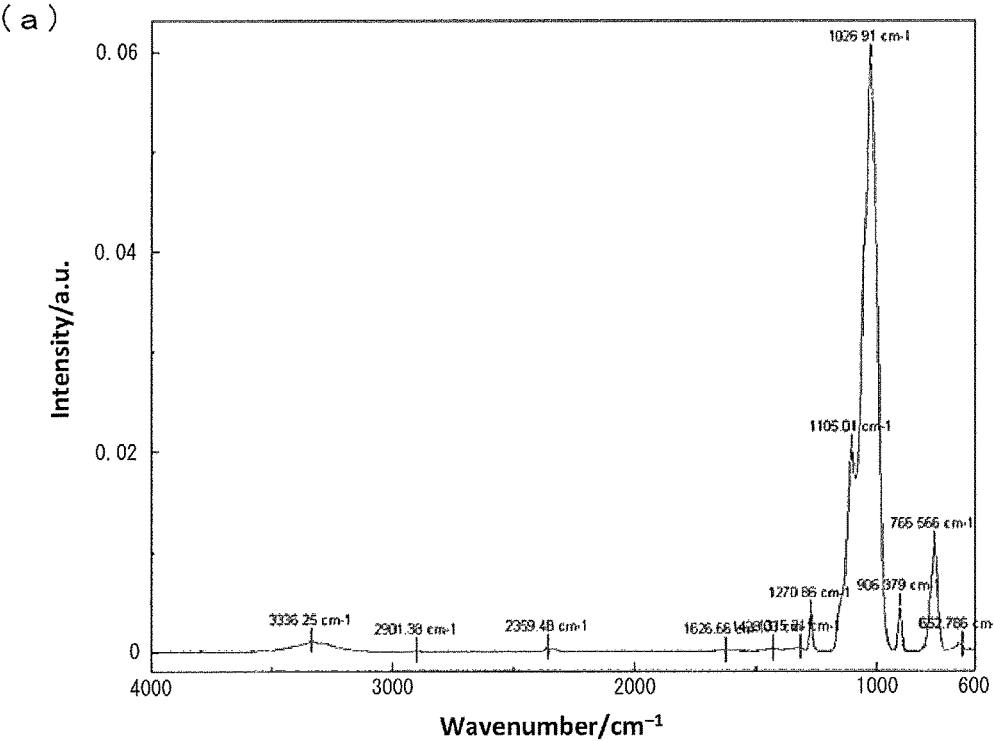
FIG. 46 shows: (a) an IR spectrum of a non-woven fabric of cotton yet to be surface-modified; and (b) an IR spectrum of a surface-modified non-woven fabric of cotton fabricated in Example 6-5.
Figure 46:
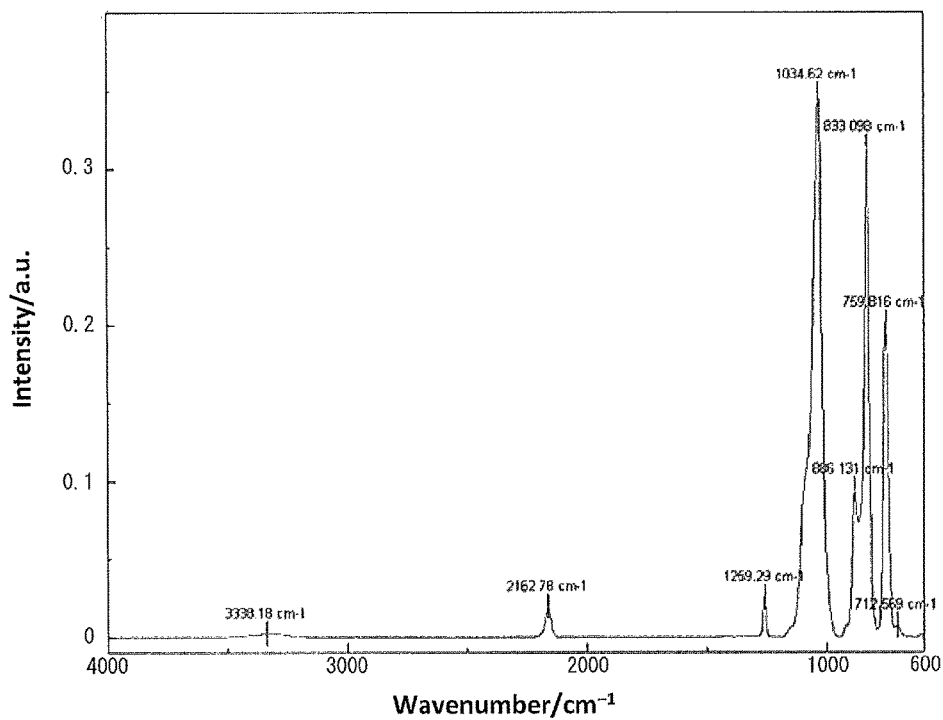

A non-woven fabric surface-modified with the molecular structure A of PMHS was obtained in the same manner as in Example 6-1, except that a non-woven fabric of cotton was used instead of the non-woven fabric of vinylon 1036. The result of IR evaluation of the non-woven fabric of cotton that had yet to be surface-modified is shown in FIG. 46(a), while the result of IR evaluation of the surface-modified non-woven fabric of cotton is shown in FIG. 46(b). As shown in FIG. 46(b), a peak attributed to the molecular structure A of PMHS, which was not observed before surface modification, and a change in peak shape at a wavenumber of around 1100 cm$^{-1}$ were observed for the surface-modified non-woven fabric of cotton.

Example 7

Modification of Surface of Glass

In Example 7, automobile side glass was used as the base material, and the surface of the glass was modified with the molecular structure A of a hydrosilane compound.

Figure 47:
FIG. 47 shows how a water droplet contacts the surface of surface-modified glass fabricated in Example 7.

First, a masking tape was used to define an exposed surface with an area of 12 cm×12 cm in the side glass. Next, the exposed surface was subjected to corona discharge treatment (9 kV) using a corona discharge treatment apparatus (manufactured by Shinko Electric & Instrumentation Co., Ltd., Corona Fit CFG-500). A liquid mixture of PMHS (2000 mg, 6.54 mmol), B(C$_6$F$_5$)$_3$ (30 mg, 0.06 mmol), and anhydrous methylene chloride (manufactured by Sigma-Aldrich Co. LLC., 5 mL) was then applied to the treated surface of the glass, which was left for 1 minute. The surface was then washed with methylene chloride and hexane and was dried. The surface of the glass subjected to such treatment repelled water, which confirmed that the surface was hydrophobized and rendered water-repellent by modification with the molecular structure A of PMHS. The treated surface of the glass is shown in FIG. 47. As shown in FIG. 47, droplets of water attached to the treated area in the side glass formed a large contact angle and thus quickly run down.

Example 8

Modification of Surface of Powder

Example 8-1

A powder of silica gel (300 mg) was heated to dryness under vacuum atmosphere, and then PMHS (150 mg, 0.06 mmol) and anhydrous methylene chloride (manufactured by Sigma-Aldrich Co. LLC., 3 mL) were added, followed by stirring. To the stirred mixture was then added dropwise a mixed solution of B(C$_6$F$_5$)$_3$ (10 mg, 0.02 mmol) and anhydrous methylene chloride (manufactured by Sigma-Aldrich Co. LLC., 0.5 mL), followed by stirring at room temperature for 5 minutes. The evolution of hydrogen ceased before end of the stirring. Subsequently, the supernatant was removed, and methylene chloride was added in approximately the same amount as the removed supernatant, followed by stirring to wash the silica gel powder. This washing was repeated three times, followed by drying to obtain a silica gel powder surface-modified with the molecular structure A of PMHS.

Figure 48:
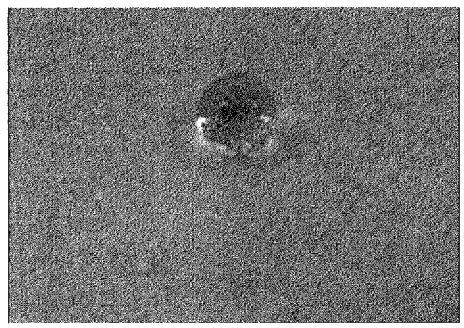
FIG. 48 shows how a water droplet contacts a surface-modified silica gel powder fabricated in Example 8-1.

The obtained silica gel powder was spread thinly on a non-woven fabric, onto which a water droplet was dropped. As shown in FIG. 48, the droplet formed a contact angle of more than 140° as visually observed, which confirmed that water repellency was imparted to the silica gel powder as a result of surface modification.

Example 8-2

Figure 49:
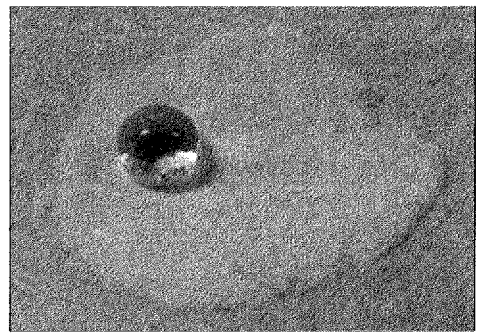
FIG. 49 shows how a water droplet contacts a surface-modified alumina powder fabricated in Example 8-2.

An alumina powder surface-modified with the molecular structure A of PMHS was obtained in the same manner as in Example 8-1, except that an alumina powder (300 mg) was used instead of the silica gel powder. The obtained alumina powder was spread thinly on a non-woven fabric, onto which a water droplet was dropped. As shown in FIG. 49, the droplet formed a contact angle of more than 140° as visually observed, which confirmed that water repellency was imparted to the alumina powder as a result of surface modification.

Example 9

Fabrication of Joined Body

Example 9-1

Figure 50:
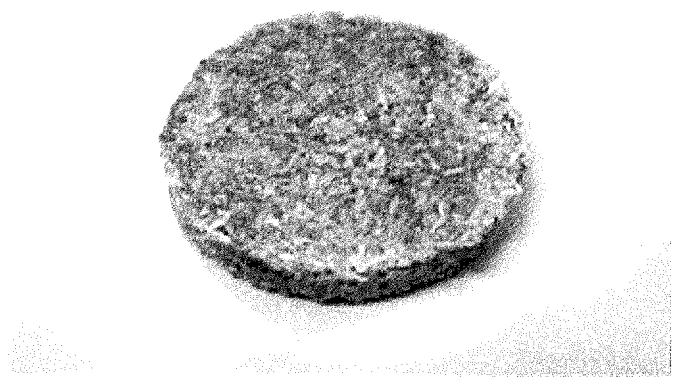
FIG. 50 shows a joined body of wood powder fabricated in Example 9-1.

A wood powder (2.0 g) and PMHS (3.0 g, 6.0 mmol) were mixed at room temperature. To the mixture was slowly added a liquid mixture of $B(C_6F_5)_3$ (10 mg, 0.02 mmol) and anhydrous methylene chloride (manufactured by Sigma-Aldrich Co. LLC., 2 mL). The addition was followed by standing at room temperature under air for 3 minutes. As a result, a joined body of wood powder hardened in the shape of a container in which the above steps were carried out was obtained. The obtained joined body is shown in FIG. 50. The obtained joined body was rigid and was not able to be broken with hands.

Example 9-2

Figure 51:
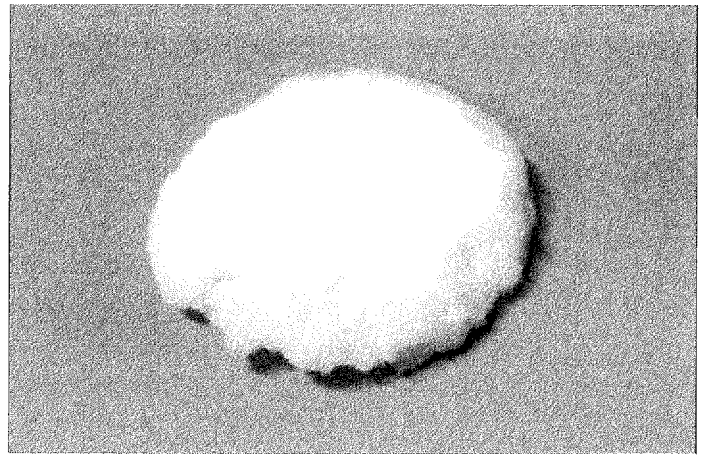
FIG. 51 shows a joined body of silica gel particles fabricated in Example 9-2.

Silica gel particles (manufactured by KANTO CHEMICAL CO., INC., Silica Gel 60 N, 100 to 210 μm, 2.0 g) and PMHS (3.0 g, 6.0 mmol) were mixed at room temperature. To the mixture was slowly added a liquid mixture of $B(C_6F_5)_3$ (10 mg, 0.02 mmol) and anhydrous methylene chloride (manufactured by Sigma-Aldrich Co. LLC., 2 mL). The addition was followed by standing at room temperature under air for 3 minutes. As a result, a joined body of silica gel powder hardened in the shape of a container in which the above steps were carried out was obtained. The obtained joined body is shown in FIG. 51. The obtained joined body was rigid and was not able to be broken with hands.

Example 9-3

Figure 52:
FIG. 52 shows a joined body of alumina powder fabricated in Example 9-3.

An alumina powder (manufactured by Wako Pure Chemical Industries, Ltd., 012-01965, 4.0 g) and PMHS (3.0 g, 6.0 mmol) were mixed at room temperature. To the mixture was slowly added a liquid mixture of $B(C_6F_5)_3$ (10 mg, 0.02 mmol) and anhydrous methylene chloride (manufactured by Sigma-Aldrich Co. LLC., 2 mL). The addition was followed by standing at room temperature under air for 3 minutes. As a result, a joined body of alumina powder hardened in the shape of a container in which the above steps were carried out was obtained. The obtained joined body is shown in FIG. 52. The obtained joined body was rigid and was not able to be broken with hands.

Example 9-4

A wood powder (2.0 g) and PMHS (3.0 g, 6.0 mmol) were mixed at room temperature. To the mixture was slowly added a liquid mixture of $B(C_6F_5)_3$ (10 mg, 0.02 mmol) and anhydrous methylene chloride (manufactured by Sigma-Aldrich Co. LLC., 2 mL). The addition was followed by standing at room temperature under air for 3 minutes, with a pressure of 0.1 MPa being applied to the mixture. As a result, a joined body of wood powder hardened in the shape of a container in which the above steps were carried out was obtained. The obtained joined body of wood powder was exposed to flame of a gas burner for 3 minutes. The interior of the joined body maintained the same state as before exposure to flame without burning, although a portion kept in direct contact with flame showed a change in appearance. That is, the joined body fabricated was flame-retardant.

Preparation of Hydrosilane Compounds: Part 2

All of the hydrosilane compounds prepared in Production Examples 22 to 38 described hereinafter are new compounds.

Production Example 22

Synthesis of 5,6-epoxyhexyldimethylsilane

THF (12 mL) as a solvent was added under nitrogen atmosphere to CuCN (97.3 mg, 1.09 mmol) and a compound (1.00 g, 10.9 mmol) shown on the left in the left-hand side of the chemical formula given below. Next, the whole mixture was cooled to −78° C., and a THF solution of a compound (17.0 mL, 14.1 mmol) shown on the right in the left-hand side of the below chemical formula was added dropwise, followed by stirring at −20° C. for 3 hours to allow the reaction to proceed. After completion of the reaction, a saturated aqueous $NH_4Cl$ solution was added for quenching, and the aqueous layer was extracted with $Et_2O$. The remaining organic layer was washed with a saturated aqueous NaCl solution, dried over $MgSO_4$, and filtered, followed by concentration to obtain a crude product. The crude product obtained was then purified by silica gel column chromatography to obtain 6-chloro-5-hydroxyhexyldimethylsilane in a yield of 92%. The reaction formula for the reaction is shown below.

[Chemical Formula 32]

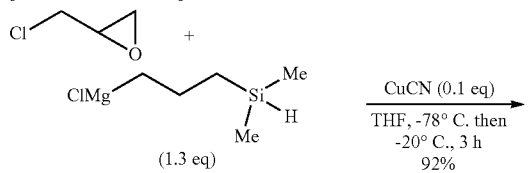

-continued

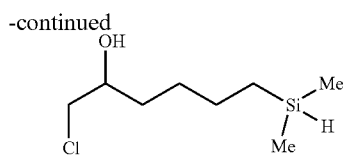

The 6-chloro-5-hydroxyhexyldimethylsilane obtained was identified by $^1$H-NMR measurement. The chemical shifts determined were as follows.

δ (ppm): 0.07-0.06 (d, J=3.6 Hz, 6H), 0.62-0.57 (m, 2H), 1.58-1.36 (m, 6H), 3.50-3.46 (dd, J=6.8, 6.8 Hz, 1H), 3.66-3.63 (dd, J=3.2, 3.2 Hz, 1H), 3.87-3.78 (m, 2H)

Next, the obtained 6-chloro-5-hydroxyhexyldimethylsilane was used to allow a reaction to take place as follows. Specifically, a THF (26.2 mL) as a solvent was put in a reaction vessel containing NaH (251 mg, 10.5 mmol) under nitrogen atmosphere. Next, the 6-chloro-5-hydroxyhexyldimethylsilane (1.93 g, 9.96 mmol) fabricated as above was added, followed by a temperature rise to 80° C. and then by stirring for 4.5 hours to allow the reaction to proceed. After completion of the reaction, a saturated aqueous NH$_4$Cl solution was added for quenching, and the aqueous layer was extracted with an ether. The remaining organic layer was washed with a saturated aqueous NaCl solution, dried over MgSO$_4$, and filtered, followed by concentration to obtain a crude product. The crude product obtained was purified by silica gel column chromatography to obtain 5,6-epoxyhexyldimethylsilane in a yield of 68%. The reaction formula for the reaction is shown below.

[Chemical Formula 33]

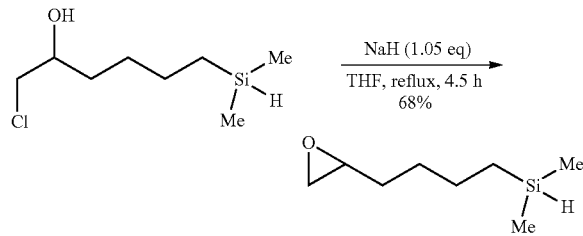

The 5,6-epoxyhexyldimethylsilane obtained was identified by $^1$H-NMR measurement. The chemical shifts determined were as follows.

δ (ppm): 0.07-0.06 (d, J=3.6 Hz, 6H), 0.62-0.58 (m, 2H), 1.60-1.37 (m, 6H), 2.48-2.46 (dd, J=2.8, 2.4 Hz, 1H), 2.76-2.74 (t, 4.0 Hz, 1H), 2.93-2.89 (m, 1H), 3.87-3.82 (m, 1H)

Production Example 23

Synthesis of (3-dimethylsilylpropyl)trifluoroacetamide

A methylene chloride solution (10 mL) of anhydrous trifluoroacetic acid (1.69 mL, 12 mmol) was added dropwise to a methylene chloride solution (10 mL) of (3-aminopropyl)dimethylsilane (1170 mg, 10 mmol) and triethylamine (2.8 mL, 20 mmol) under nitrogen atmosphere at 0° C. Next, the whole mixture was heated to room temperature and stirred for 15 hours. The reaction mixture was then subjected to liquid-liquid separation by adding ion-exchanged water, and the aqueous layer was extracted with methylene chloride. Next, the remaining organic layer was washed with brine, dried over sodium sulfate, and then filtered. The solution obtained by the filtration was concentrated under reduced pressure to quantitatively obtain (3-dimethylsilylpropyl)trifluoroacetamide (2130 mg, 10 mmol). The reaction formula for the reaction is shown below.

[Chemical Formula 34]

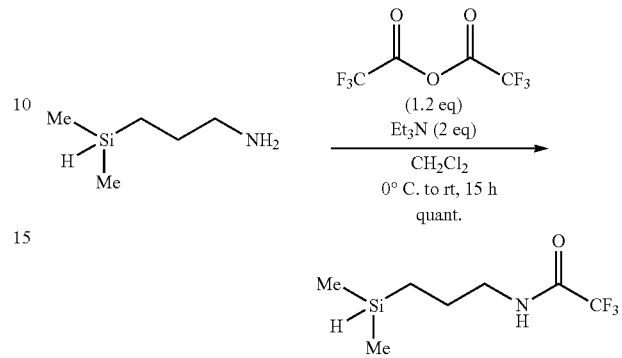

The (3-dimethylsilylpropyl)trifluoroacetamide obtained was identified by $^1$H-NMR measurement. The chemical shifts determined were as follows.

δ (ppm): 6.37 (br, 1H), 3.85-3.90 (m, 1H), 3.34-3.39 (q, J=7.2 Hz, 2H), 1.59-1.67 (m, 2H), 0.58-0.63 (m, 2H), 0.09-0.10 (d, J=4.0 Hz, 6H)

Production Example 24

Synthesis of phthaloylpolymethylhydrosiloxane (PMHS-Pht)

2-propanol (50 μL) was added to chloroplatinic acid hexahydrate (0.7 mg, 1 μmol), to which were then added allyl phthalimide (3748 mg, 20 mmol) and toluene (5 mL). A liquid mixture thus prepared was heated to 60° C., and polymethylhydrosiloxane (2450 mg, 40 mmol) was added dropwise to the liquid mixture, which was stirred under nitrogen atmosphere for 12 hours to allow the reaction to proceed. Next, the reaction mixture was cooled to room temperature, and then filtered through Florisil (registered trademark) using a hexane/ethyl acetate mixture (mixing volume ratio: hexane/ethyl acetate=4/1). The resulting filtrate was then concentrated to obtain 5580 mg of a hydrosilane derivative having a phthaloyl group, PMHS-Pht, in a yield of 90%. The reaction formula for the reaction is shown below.

[Chemical Formula 35]

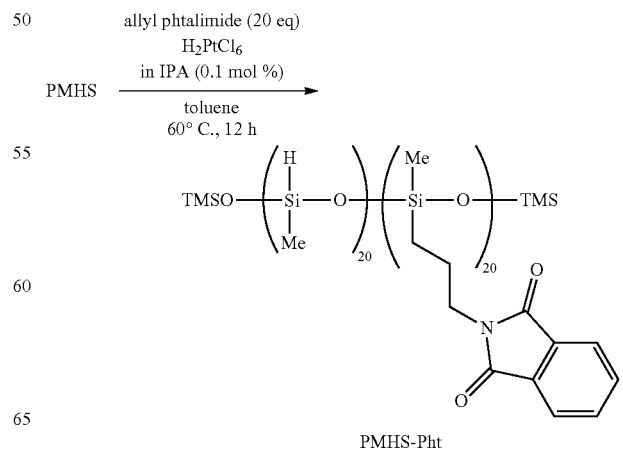

The PMHS-Pht obtained was identified by ¹H-NMR measurement. The chemical shifts determined were as follows.

δ (ppm): 7.55-7.90 (m, 80H), 4.61 (s, 20H), 3.50-3.70 (m, 40H), 1.58-1.78 (m, 40H), 0.45-0.62 (m, 40H), 0.00-0.25 (m, 138H)

In Production Examples 25 to 38 which will be described later, hydride groups of polymethylhydrosiloxane (PMHS) were converted to synthesize various types of organo-modified polymethylhydrosilane. Specifically, various polymeric hydrosilane derivatives were synthesized in such a manner that some of a number of hydrosilyl groups present in PMHS were modified while the hydrosilyl groups other than the modified hydrosilyl groups were allowed to remain. The synthesis was performed by either of the following two methods: a method that uses hydrosilylation reaction; and a method in which the hydrosilyl groups are converted to chlorosilyl groups and then a nucleophile is reacted. Production Examples 25 to 33 employed the former method, while Production Examples 34 to 38 employed the latter method. The latter method is capable of synthesis of a derivative without the use of a transition metal catalyst. A transition metal catalyst such as a platinum catalyst allows a reaction to proceed even when used in a very small catalytic amount, such as in an amount of 0.001 mol %. However, such a catalyst is difficult to fully remove after the reaction, and this may diminish the stability of the resulting derivative and cause gradual evolution of hydrogen gas. Depending on the type of the modified groups, the latter method can avoid such a problem and thus yield a derivative suitable for commercial distribution and storage.

Production Example 25

Synthesis of modified PMHS having 3-chloropropyl group

PMHS (2.45 g, 1 mmol), toluene (1 mL), allyl chloride (1.53 g, 20 mmol), and a 0.01 M isopropyl alcohol solution of chloroplatinic acid (0.1 mL) were put in a dried test tube. The inside of the test tube was purged with nitrogen, and the tube was then sealed, followed by stirring at 100° C. for 12 hours to allow the reaction to proceed. Next, the reaction mixture was filtered through Florisil, and then the remaining unreacted allyl chloride and toluene were distilled off using an evaporator, so that modified PMHS having a 3-chloropropyl group was obtained. The reaction formula for the reaction is shown below. X in the right-hand side is a hydrogen atom, a chlorine atom, or a 3-chloropropyl group, and the abundance ratio among them is 20:5:15.

[Chemical Formula 36]

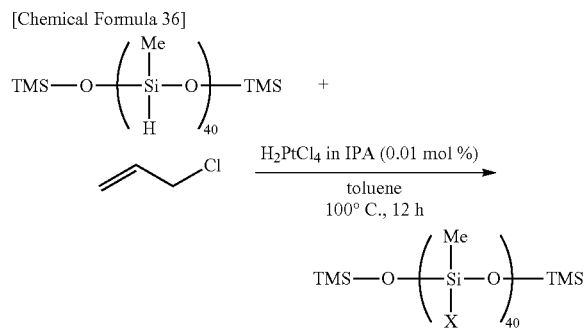

The modified PMHS obtained was identified by ¹H-NMR measurement. The chemical shifts determined were as follows.

δ (ppm): 4.65-4.79 (br, 20H), 3.43-3.63 (br, 30H), 1.76-1.91 (br, 30H), 1.58-1.71 (br, 15H), 0.92-1.01 (br, 30H), 0.03-0.25 (m, 123H)

Production Example 26

Synthesis of modified PMHS having 3-aminopropyl group

PMHS (2.45 g, 1 mmol), toluene (1 mL), allylamine (1.53 g, 20 mmol), and a 0.01 M isopropyl alcohol solution of chloroplatinic acid (0.1 mL) were put in a dried test tube. The inside of the test tube was purged with nitrogen, and the tube was then sealed, followed by stirring at 100° C. for 12 hours to allow the reaction to proceed. Next, the reaction mixture was filtered through Florisil, and then the remaining unreacted allylamine and toluene were distilled off using an evaporator, so that modified PMHS having a 3-aminopropyl group was obtained. The reaction formula for the reaction is shown below. X in the right-hand side is a hydrogen atom or a 3-aminopropyl group, and the abundance ratio between them is 20:20.

[Chemical Formula 37]

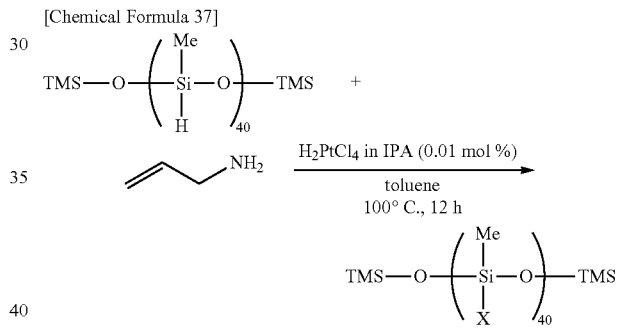

The modified PMHS obtained was identified by ¹H-NMR measurement. The chemical shifts determined were as follows.

δ (ppm): 4.61-4.72 (br, 20H), 2.62-2.73 (br, 40H), 1.34-1.59 (br, 40H), 1.20-1.38 (br, 40H), 0.78-0.99 (br, 40H), 0.03-0.25 (m, 138H)

Production Example 27

Synthesis of modified PMHS having 3-acetoxypropyl group

PMHS (2.45 g, 1 mmol), toluene (1 mL), allyl acetate (1.53 g, 20 mmol), and a 0.01 M isopropyl alcohol solution of chloroplatinic acid (0.1 mL) were put in a dried test tube. The inside of the test tube was purged with nitrogen, and the tube was then sealed, followed by stirring at 100° C. for 12 hours to allow the reaction to proceed. Next, the reaction mixture was filtered through Florisil, and then the remaining unreacted allyl chloride and toluene were distilled off using an evaporator, so that modified PMHS having a 3-acetoxypropyl group was obtained. The reaction formula for the reaction is shown below. X in the right-hand side is a hydrogen atom or a 3-acetoxypropyl group, and the abundance ratio between them is 20:20.

[Chemical Formula 38]

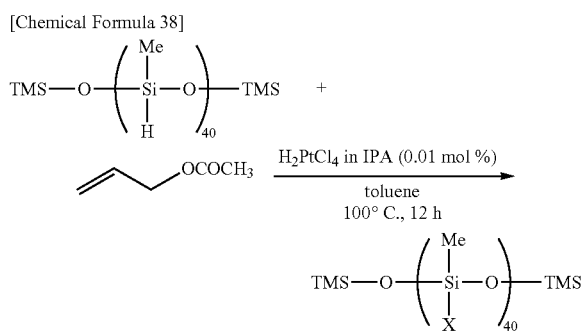

The modified PMHS obtained was identified by $^1$H-NMR measurement. The chemical shifts determined were as follows.

δ (ppm): 4.65-4.79 (br, 20H), 3.97-4.06 (br, 40H), 1.99-2.11 (br, 60H), 1.57-1.77 (br, 40H), 1.31-1.46 (br, 40H), 0.03-0.25 (m, 138H)

Production Example 28

Synthesis of modified PMHS having isopropoxylated chlorosilyl moiety 3-chloropropyl group-containing modified PMHS as fabricated in Production Example 25 (3.77 g, 1 mmol), toluene (1 mL), and 2-propanol (7.7 mL, 10 mmol) were put in a dried 20 mL Schlenk tube, and were stirred under nitrogen atmosphere for 30 minutes. Next, the remaining unreacted 2-propanol and toluene were distilled off using an evaporator, so that modified PMHS having an isopropoxy group was obtained. The reaction formula for the reaction is shown below. X in the left-hand side of the reaction formula is a hydrogen atom, a chlorine atom, or a 3-chloropropyl group, and the abundance ratio among them is 20:5:15. X in the right-hand side is a hydrogen atom, an isopropoxy group, or a 3-chloropropyl group, and the abundance ratio among them is 20:5:15.

[Chemical Formula 39]

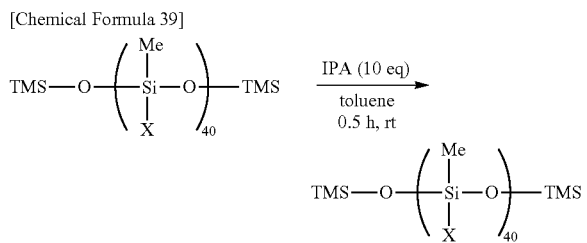

The modified PMHS obtained was identified by $^1$H-NMR measurement. The chemical shifts determined were as follows.

δ (ppm): 4.65-4.79 (br, 20H), 4.08-4.27 (br, 5H), 3.45-3.61 (br, 30H), 1.75-1.92 (br, 30H), 1.13-1.23 (br, 30H), 0.92-1.01 (br, 30H), 0.03-0.25 (m, 138H)

Production Example 29

Synthesis of modified PMHS having 3-azidopropyl group

Modified PMHS (465 mg, 0.1 mmol) as prepared d in Production Example 28, DMF (4 mL), and sodium azide (195 mg, 3 mmol) were put in a dried 20 mL Schlenk tube, and were stirred under nitrogen atmosphere at 65° C. for 12 hours. This was followed by addition of distilled water, then extraction with ethyl acetate, then dehydration with sodium sulfate, then filtration, and then drying under reduced pressure. Modified PMHS having a 3-azidopropyl group was thus obtained. The reaction formula for the reaction is shown below. X in the left-hand side is a hydrogen atom, an isopropoxy group, or a 3-chloropropyl group, and the abundance ratio among them is 20:5:15. X in the right-hand side is a hydrogen atom, an isopropoxy group, or a 3-azidopropyl group, and the abundance ratio among them is 20:5:15.

[Chemical Formula 40]

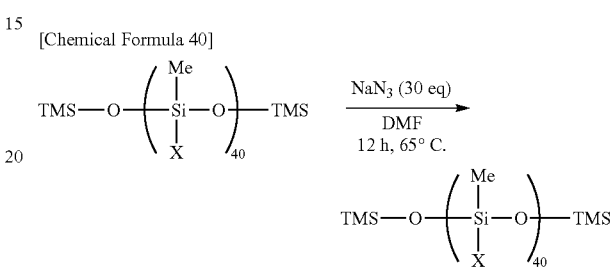

The modified PMHS obtained was identified by $^1$H-NMR measurement. The chemical shifts determined were as follows.

δ (ppm): 4.62-4.73 (br, 20H), 4.09-4.23 (br, 5H), 3.18-3.28 (br, 30H), 1.54-1.73 (br, 30H), 1.13-1.21 (br, 30H), 0.90-0.98 (br, 30H), 0.03-0.25 (m, 138H)

Production Example 30

Synthesis of modified PMHS having 3-bromopropyl group

PMHS (390 mg, 1 mmol), toluene (1 mL), allyl bromide (121 mg, 2 mmol), [IrCl(cod)]$_2$ (0.27 mg, 0.0004 mol), and cyclooctadiene (COD: 0.86 mg, 0.008 mol) were put in a dried test tube. Next, the inside of the test tube was purged with nitrogen, and the tube was then sealed, followed by stirring at 60° C. for 12 hours. This was followed by filtration through Florisil and then by distilling off of the remaining unreacted allyl bromide and toluene using an evaporator. Modified PMHS having a 3-bromopropyl group was thus obtained. The reaction formula for the reaction is shown below. R in the left-hand side and right-hand side of the reaction formula is a bromine atom.

[Chemical Formula 41]

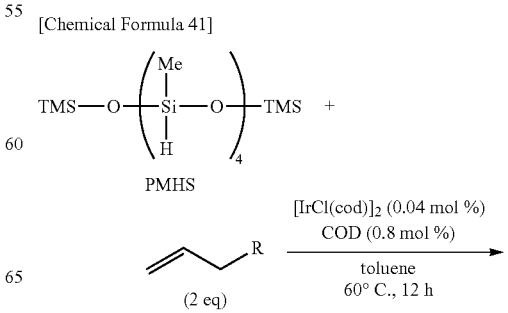

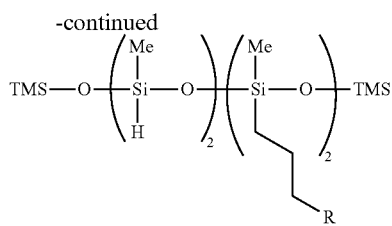

The modified PMHS obtained was identified by $^1$H-NMR measurement. The chemical shifts determined were as follows.

δ (ppm): 4.65-4.72 (br, 2H), 3.35-3.44 (br, 4H), 1.85-1.99 (br, 4H), 0.60-0.76 (br, 4H), 0.03-0.25 (br, 30H)

Production Example 31

Synthesis of modified PMHS having hydrocarbon group (alkyl group represented by $C_{12}H_{25}$)

2-propanol (50 μL) was added to chloroplatinic acid hexahydrate (0.7 mg, 1 μmol), to which were then added dodecene (3367 mg, 20 mmol) and toluene (5 mL). This liquid mixture was heated to 100° C., and polymethylhydrosiloxane (2450 mg, 40 mmol) was added dropwise, followed by stirring under nitrogen atmosphere for 12 hours. Next, the reaction mixture was cooled to room temperature, and then filtered through Florisil using hexane. The filtrate was then concentrated to obtain 5350 mg of a hydrosilane derivative (PMHS-$C_{12}$ 1:1) having a dodecyl group ($C_{12}H_{25}$ group) in a yield of 92%. The reaction formula for the reaction is shown below.

[Chemical Formula 42]

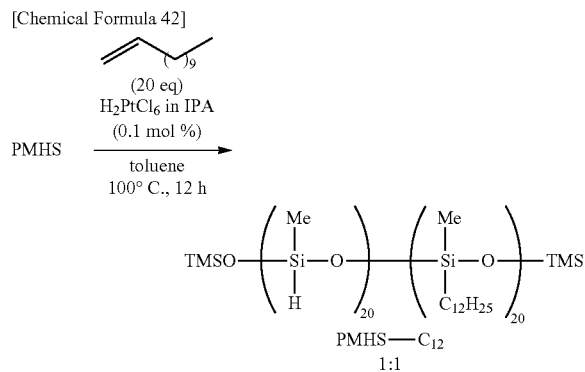

The modified PMHS obtained was identified by $^1$H-NMR measurement. The chemical shifts determined were as follows.

δ (ppm): 4.70 (s, 20H), 1.20-1.30 (m, 400H), 0.86-0.90 (t, J=7.2 Hz, 60H), 0.45-0.58 (br, 40H), 0.02-0.20 (m, 138H)

Production Example 32

Synthesis of modified PMHS having alkyl group ($C_{18}H_{37}$ group)

2-propanol (50 μL) was added to chloroplatinic acid hexahydrate (0.7 mg, 1 μmol), to which were then added octadecene (5050 mg, 20 mmol) and toluene (5 mL). This liquid mixture was heated to 100° C., and polymethylhydrosiloxane (2450 mg, 40 mmol) was added dropwise, followed by stirring under nitrogen atmosphere for 12 hours. Next, the reaction mixture was cooled to room temperature, and then filtered through Florisil using hexane. The filtrate was then concentrated to obtain 7125 mg of a hydrosilane derivative (PMHS-$C_{18}$ 1:1) having an octadecyl group ($C_{18}H_{37}$ group) in a yield of 95%. The reaction formula for the reaction is shown below.

[Chemical Formula 43]

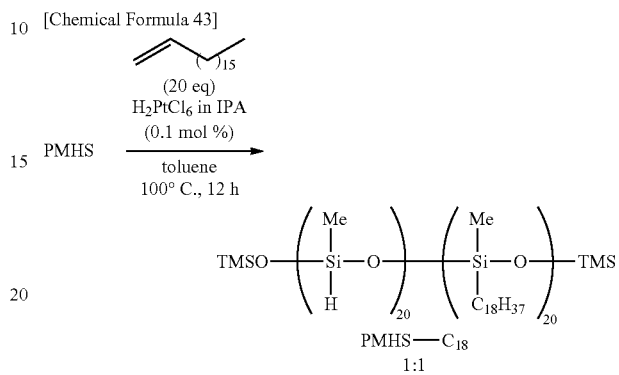

The modified PMHS obtained was identified by $^1$H-NMR measurement. The chemical shifts determined were as follows.

δ (ppm): 4.70 (s, 20H), 1.20-1.38 (m, 640H), 0.86-0.90 (t, J=7.2 Hz, 60H), 0.45-0.58 (br, 40H), 0.02-0.20 (m, 138H)

Production Example 33

Synthesis of modified PMHS having perfluorohexylethyl group (Perfluorohexyl)ethylene (3460 mg, 10 mmol) and polymethylhydrosiloxane (1225 mg, 0.5 mmol) were mixed with toluene (3 mL), and the mixture was heated to 40° C. A Karstedt's catalyst (0.5 mg, 0.5 μmol) was then added, followed by stirring under nitrogen atmosphere for 12 hours. Next, the reaction mixture was cooled to room temperature and then filtered through Florisil using hexane. The filtrate was then concentrated to obtain 3758 mg of a hydrosilane derivative, PMHS-Rf, having a perfluorohexylethyl group in a yield of 88%. The reaction formula for the reaction is shown below.

[Chemical Formula 44]

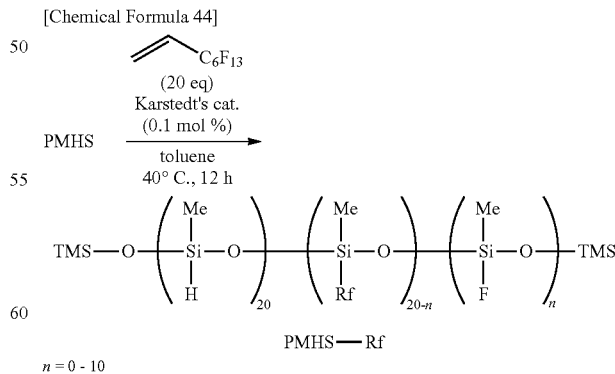

The modified PMHS obtained was identified by $^1$H-NMR measurement. The chemical shifts determined were as follows.

δ (ppm): 4.70 (s, 20H), 1.95-2.80 (m, 15H), 1.52-1.60 (m, 5H), 1.15-1.22 (m, 7H), 0.75-0.90 (m, 13H), 0.05-0.30 (m, 138H)

Production Example 34

Synthesis of polyallylmethylhydrosiloxane

Terminally trimethylsilyl-protected polymethylhydrosiloxane with a Mn of approximately 390 (400 mg, 1.02 mmol) was added dropwise to a solution of trichloroisocyanuric acid (159 mg, 0.68 mmol) in methylene chloride (8 mL) under nitrogen atmosphere at 0° C., followed by stirring at room temperature for 1 hour. Next, the resulting white suspension was subjected to Celite filtration under nitrogen, followed by concentration under reduced pressure to obtain polychloromethylhydrosiloxane. To the polychloromethylhydrosiloxane obtained was added dropwise allylmagnesium bromide (0.86 M solution in Et$_2$O, 2.8 mL, 2.4 mmol) at 0° C., followed by stirring at room temperature for 2 hours. After that, the whole mixture was diluted with diethyl ether, and then subjected to liquid-liquid separation by adding an aqueous hydrochloric acid solution with a concentration of 10 weight %. The organic layer resulting from the liquid-liquid separation was dried over sodium sulfate and then filtered, followed by concentration under reduced pressure to obtain polyallylmethylhydrosiloxane (472 mg).

In this process, polymethylhydrosiloxane and trichloroisocyanuric acid were reacted to chlorinate the hydrosilane groups of polymethylhydrosiloxane, and the reaction product was further reacted with an allyl Grignard reagent acting as a nucleophile to obtain polyallylmethylhydrosiloxane. In the process, the number of hydrosilane groups subjected to chlorination can be controlled by adjusting the mixing ratio between polymethylhydrosiloxane and trichloroisocyanuric acid. Also in the process, many types of PMHS composites differing in functional group composition can be synthesized by reaction with various nucleophiles.

Figure 53:
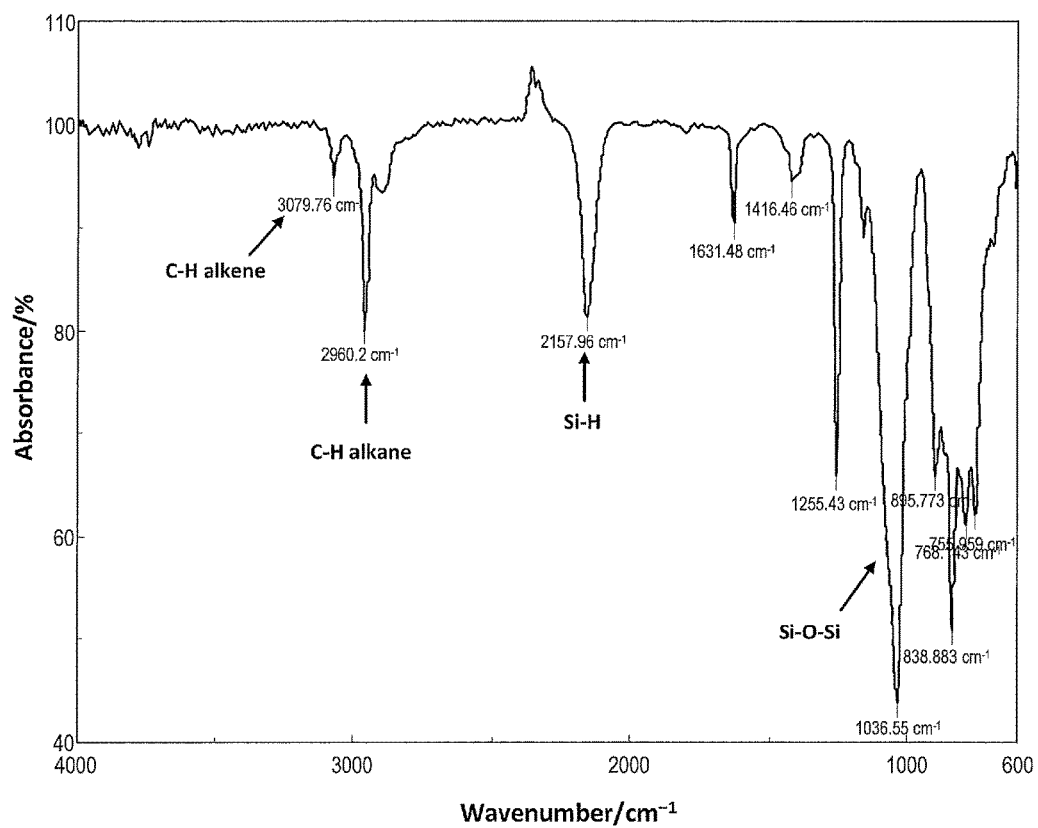
FIG. 53 shows an IR spectrum of a hydrosilane compound prepared in Production Example 34.
Figure 54:
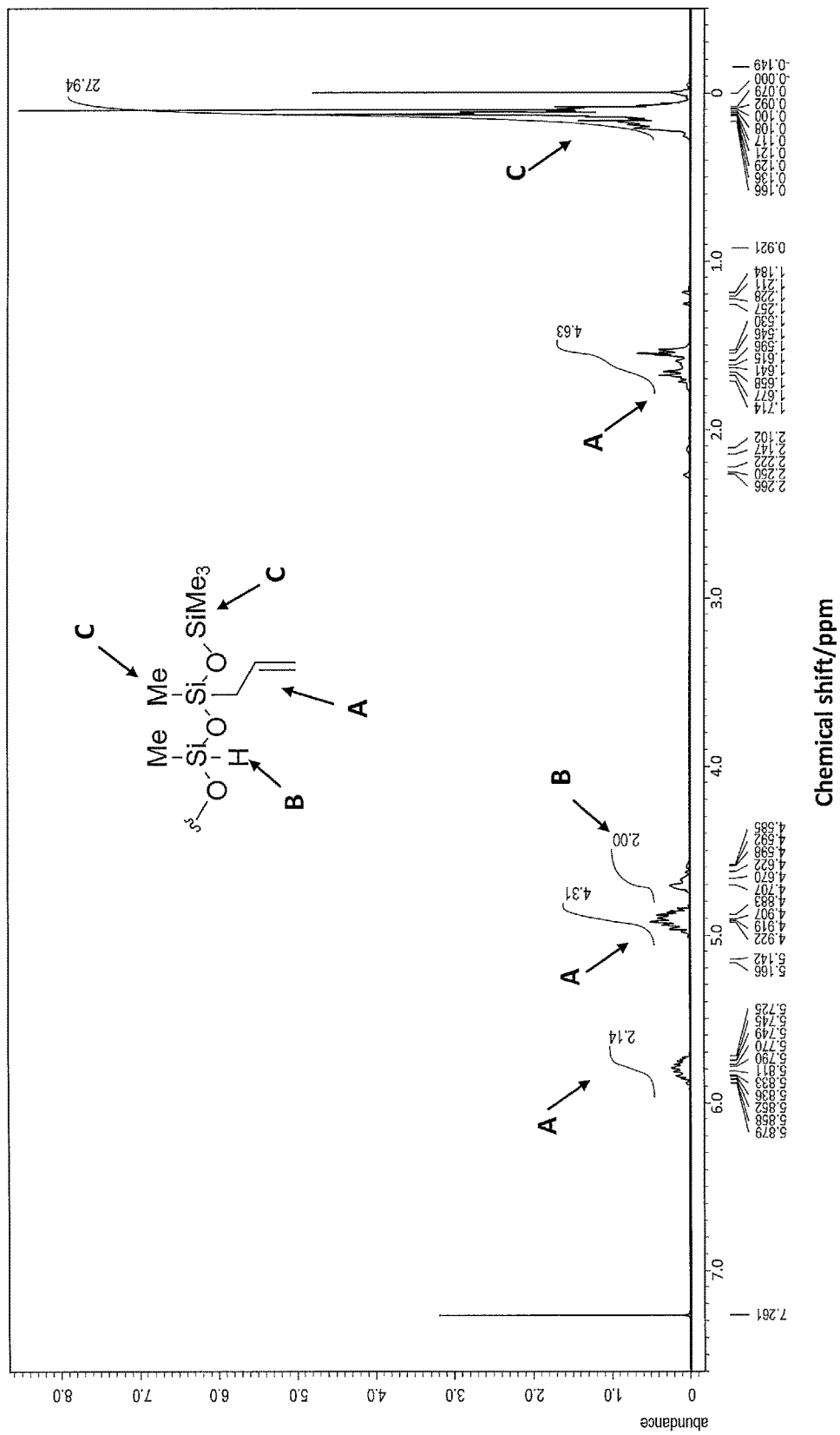
FIG. 54 shows a $^1$H-NMR profile of a hydrosilane compound prepared in Production Example 34.

For the obtained polyallylmethylhydrosiloxane, the result of IR evaluation is shown in FIG. 53, while the result of $^1$H-NMR evaluation is shown in FIG. 54.

Production Example 35

In Production Example 35, polyallylmethylhydrosiloxane as prepared in Production Example 34 was converted to polyepoxymethylhydrosiloxane.

Polyallylmethylhydrosiloxane (250 mg, 0.0856 mmol) as prepared in Production Example 34 and meta-chloroperbenzoic acid (mCPBA; 133 mg, 0.770 mmol) were dissolved in CHCl$_3$ (10 mL) under nitrogen atmosphere, followed by stirring at 5° C. for 2 days. After completion of the reaction, dimethyl sulfide was added to quench the remaining mCPBA. This was followed by washing with a saturated aqueous NaHCO$_3$ solution and then by extraction of the aqueous layer with CHCl$_3$. The extraction was followed by neutralization with a saturated aqueous NH$_4$Cl solution and then by drying of the organic layer over MgSO$_4$. Finally, filtration and concentration were performed to obtain polyepoxymethylhydrosiloxane. The reaction formula for the reaction is shown below.

[Chemical Formula 45]

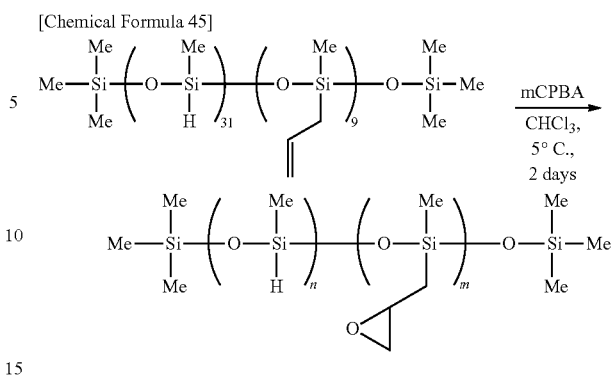

Figure 55:
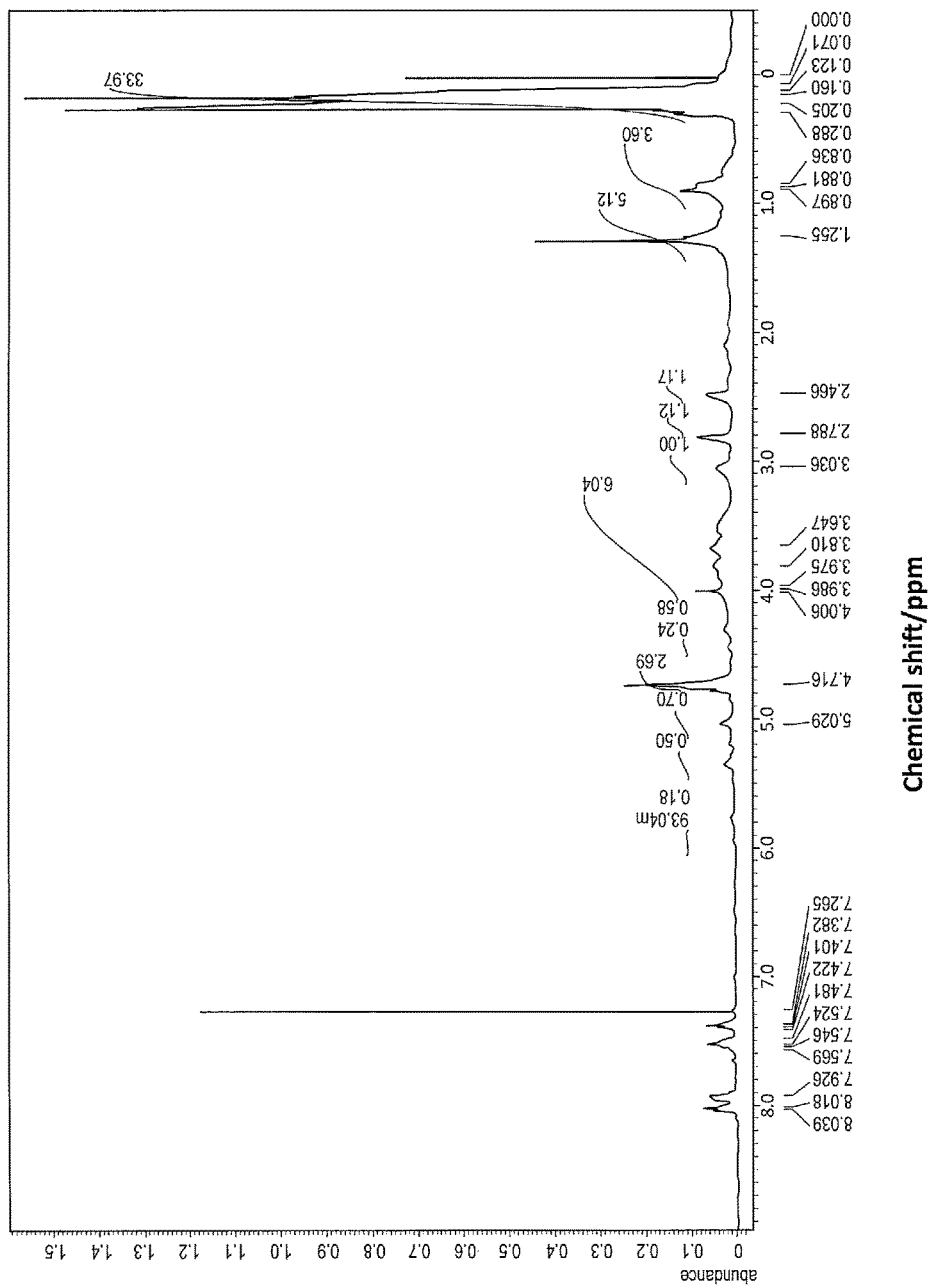
FIG. 55 shows a $^1$H-NMR profile of a hydrosilane compound prepared in Production Example 35.

The polyepoxymethylhydrosiloxane obtained was identified by $^1$H-NMR measurement. The chemical shifts determined were as follows. The chemical shifts, 3.04 ppm, 2.79 ppm, and 2.47 ppm are associated with peaks attributed to epoxy. The result of $^1$H-NMR evaluation is shown in FIG. 55.

δ (ppm): 0.29-0.07 (m), 0.92-0.84 (m), 2.47 (br), 2.79 (br), 3.04 (br), 4.72 (br)

Production Example 36

In Production Example 36, poly(chloroisopropoxy)methylhydrosiloxane was synthesized from PMHS and epichlorohydrin.

PMHS (200 mg, 0.0816 mmol) and epichlorohydrin (151 mg, 1.63 mmol) were put in a reaction vessel and dissolved in CH$_2$Cl$_2$ (8 mL). A catalytic amount of B(C$_6$F$_5$)$_3$ (5.00 mg, 0.00977 mmol) was then added, followed by stirring at room temperature for 20 minutes. After completion of the reaction, Et$_3$N was added to quench B(C$_6$F$_5$)$_3$, followed by concentration to obtain poly(chloroisopropoxy)methylhydrosiloxane. The reaction formula for the reaction is shown below. In the right-hand side, the ratio between n and m was 1:1.

[Chemical Formula 46]

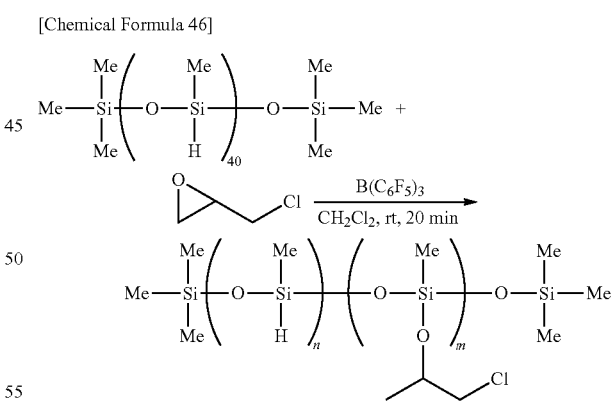

The poly(chloroisopropoxy)methylhydrosiloxane obtained was identified by 1H-NMR measurement. The chemical shifts determined were as follows.

δ (ppm): 0.22-0.13 (m, 138H), 1.30-1.28 (d, J=8.0 Hz, 60H), 3.50-3.37 (m, 40H), 4.24-4.17 (m, 20H), 4.73 (s, 20H)

Production Example 37

In Production Example 36, poly(epoxy)methylhydrosiloxane was synthesized from PMHS and trifunctional epoxide.

PMHS (50 mg, 0.0204 mmol) and trimethylolpropane triglycidyl ether (84.5 mg, 0.280 mmol) were put in a reaction vessel under nitrogen atmosphere and dissolved in cyclohexane (15 mL). Next, the whole system was heated to 70° C., and a catalytic amount of B(C$_6$F$_5$)$_3$ (5.00 mg, 0.00977 mmol) and diphenyl ether were added. This was followed by stirring at 70° C. for 15 hours. After completion of the reaction, triethylamine was added to quench B(C$_6$F$_5$)$_3$, followed by concentration to obtain poly(epoxy)methylhydrosiloxane. The reaction formula for the reaction is shown below.

[Chemical Formula 47]

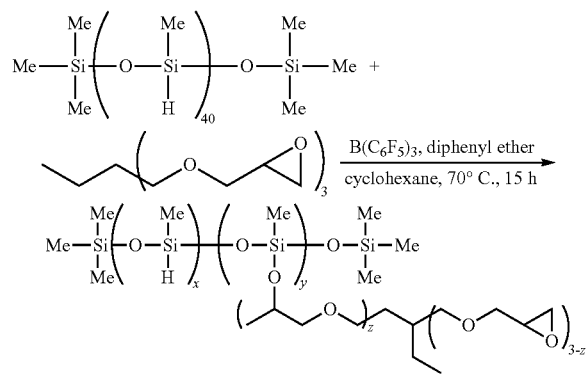

Figure 56:
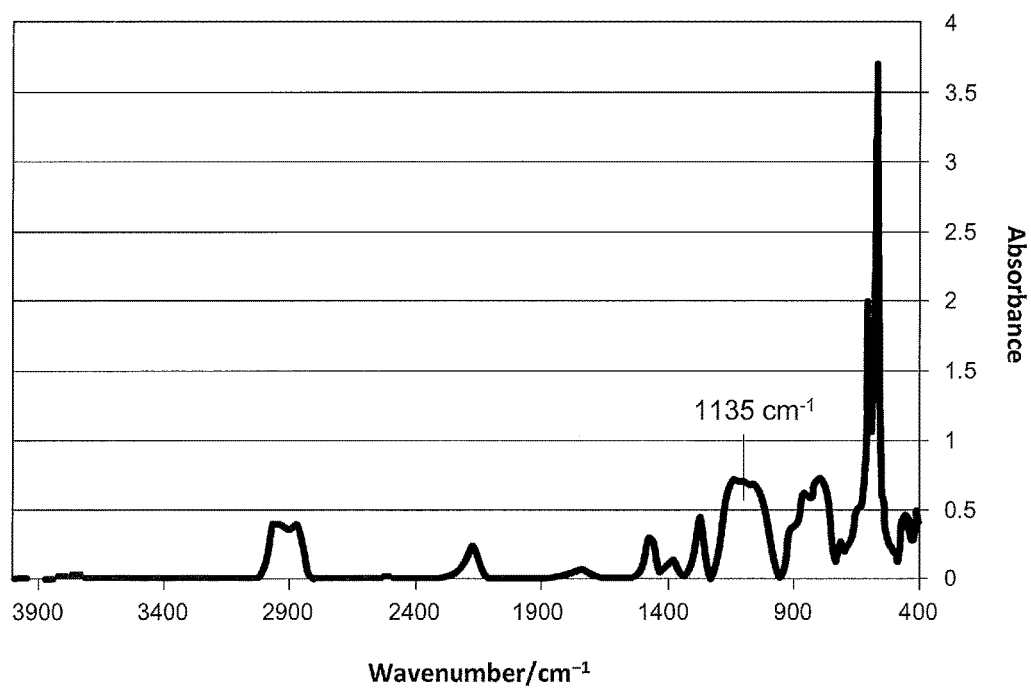
FIG. 56 shows an IR spectrum of a hydrosilane compound prepared in Production Example 37.

The result of IR evaluation of the poly(epoxy)methylhydrosiloxane obtained is shown in FIG. 56. A broad peak attributed to the Si—O—C bond was observed at a wavenumber of around 1135 cm$^{-1}$, which allows the inference that the reaction represented by the above reaction formula took place.

Production Example 38

In Production Example 38, perfluoro-modified PMHS was synthesized by a condensation reaction between 1H, 1H,2H,2H-nonafluorohexyltrimethoxysilane and PMHS.

1H, 1H,2H,2H-nonafluorohexyltrimethoxysilane (0.66 mmol, 241.35 mg) and PMHS (0.197 mmol, 500 mg) were placed in a dried Schlenk tube under nitrogen atmosphere, and anhydrous hexane (6 mL) was added as a solvent, followed by stirring. Next, tris(pentafluorophenyl)borane (0.078 mmol, 40 mg) was quickly added, followed by stirring for 30 minutes. After 30 minutes elapsed from the start of stirring, several droplets of triethylamine were added to deactivate the catalyst. After that, the reaction solution was filtered through Celite (registered trademark) using hexane, and the filtrate was concentrated using an evaporator and then vacuum-dried to obtain a hydrosilane derivative having a perfluoroalkyl group. The reaction formula for the reaction is shown below.

{Chemical Formuka 48}

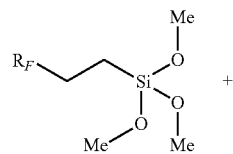

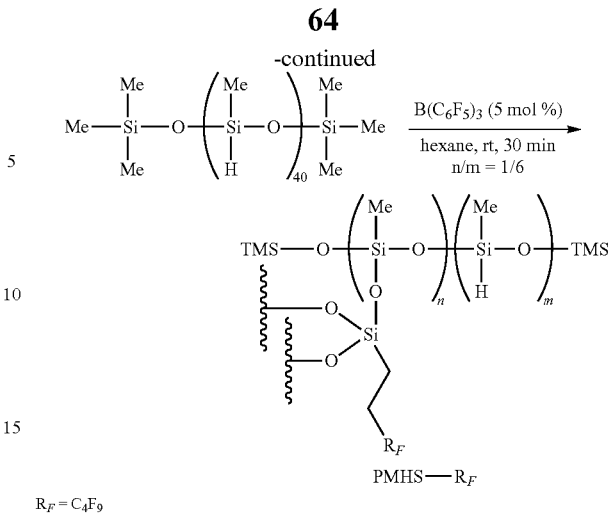

$R_F = C_4F_9$

Figure 57:
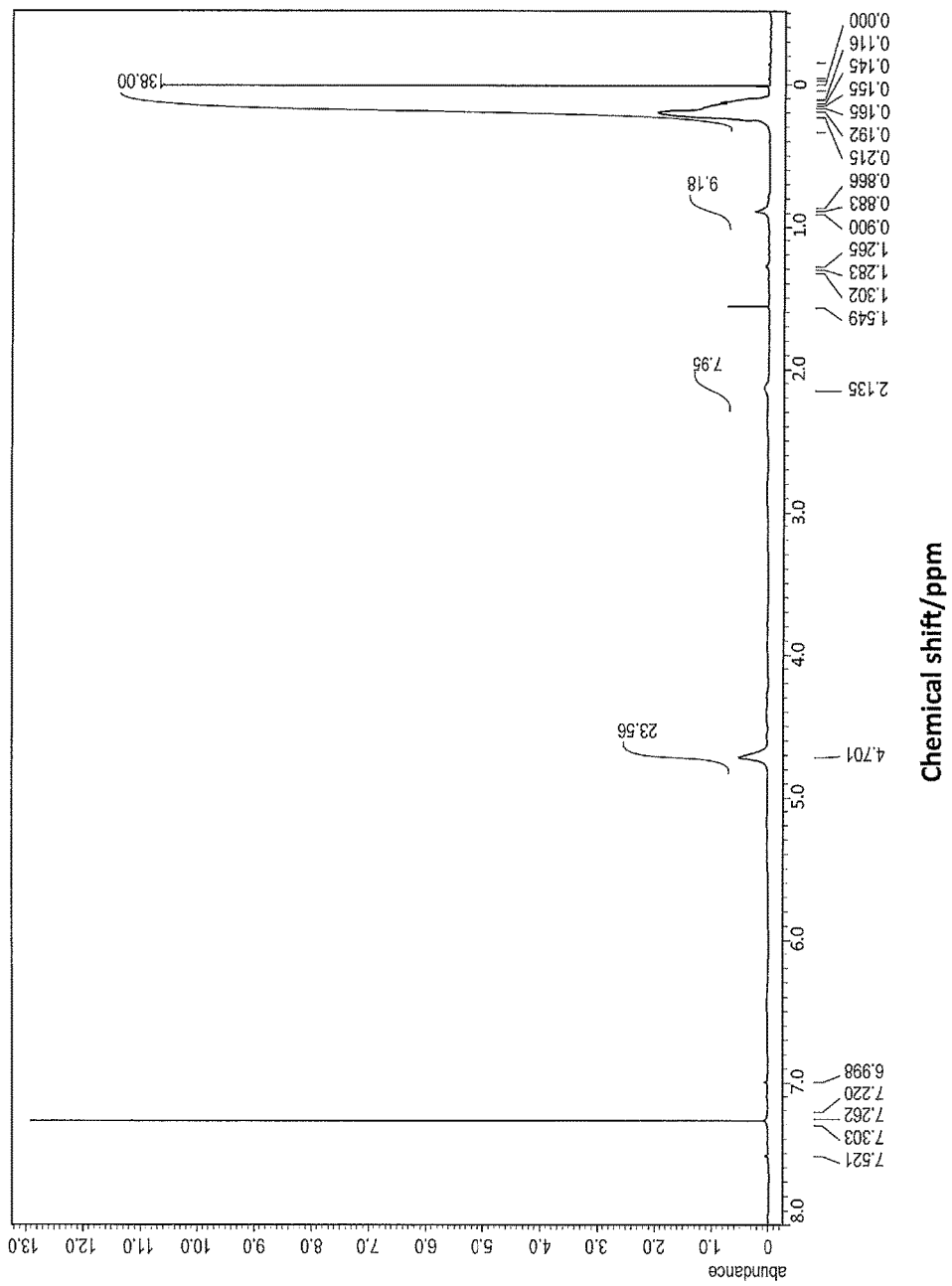
FIG. 57 shows a $^1$H-NMR profile of a hydrosilane compound prepared in Production Example 38.

The perfluoro-modifed PMHS obtained was identified by $^1$H-NMR measurement. The chemical shifts determined were as follows. The result of $^1$H-NMR measurement is shown in FIG. 57.

δ (ppm): 0.28-0.07 (br, 138H), 0.95-0.81 (br, 9H), 2.22-2.04 (br, 8H), 4.75-4.65 (br, 24H)

Example 10

Modification (Hydrophobization) of Surface of Microfibrillated Cellulose

In Example 10, the surface of microfibrillated cellulose was hydrophobized. This hydrophobization can improve, for example, the dispersibility or solubility of cellulose nanofibril in organic solvents, and facilitate the creation of cellulose nanofibril (CNF) composites. CNF composites have high strength and are easily reduced in weight. For such reasons, CNF composites are very promising for use as a next-generation material. Examples of specific applications include bodies of automobiles and housings of electrical products such as personal computers.

Cellulose nanofibril was pretreated by the following three methods.

Method 1: 100 g of CELISH (manufactured by Daicel FineChem Ltd.), which is commercially-available microfibrillated cellulose (cellulose nanofibril or cellulose nanofiber), was packed in a glass filter, through which 50 mL of acetone was passed five times, then 50 mL of methylene chloride was passed three times, and then 50 mL of cyclohexane was passed two times under ordinary pressure. Thus, microfibrillated cellulose having undergone solvent substitution with cyclohexane was obtained.

Method 2: 100 g of CELISH was placed in an eggplant-shaped flask with an internal volume of 200 mL, and a Dean-Stark apparatus and a Dimroth condenser were attached to the flask. Next, 100 mL of toluene was put in the flask, followed by a temperature rise to 95° C. and then by stirring for 12 hours. Thus, microfibrillated cellulose dehydrated by azeotropy was obtained.

Method 3: 100 g of CELISH was dried under reduced pressure at 50° C. for 8 hours to remove water. The resulting aggregated cellulose was then crushed with a mill into fine pieces.

Example 10-1

Surface Modification with PMHS

The surface of microfibrillated cellulose fabricated by the method 1 was modified with PMHS. Specifically, 5 mL of cyclohexane was added to 2 g of cyclohexane-containing microfibrillated cellulose (cellulose nanofiber), to which 1 g of PMHS and 30 mg of diphenyl ether were further added. Next, the reaction mixture was raised in temperature to 50° C., and 10 mg of tris(pentafluorophenyl)borane was added, followed by vigorous stirring for 10 minutes. This was followed by cooling to room temperature, then separation by filtration through a glass fiter, and then washing with hexane. Microfibrillated cellulose surface-modified with PMHS (PMHS-CNF) was thus obtained. When the PMHS-CNF obtained was dispersed in chloroform, the PMHS-CNF showed significantly higher dispersibility than unmodified CNF. The reaction formula for the modification is shown below.

[Chemical Formula 49]

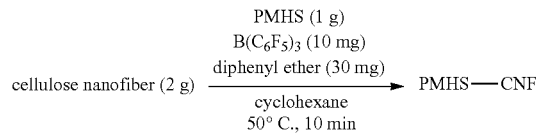

Besides this, the same surface modification with PMHS was performed using microfibrillated cellulose fabricated by the method 2 instead of the microfibrillated cellulose fabricated by the method 1, in consequence of which the same result was obtained.

Example 10-2

Surface Modification with PMHS-$C_{12}$

The surface of microfibrillated cellulose fabricated by the method 3 was modified with alkyl group ($C_{12}H_{25}$ group)-containing modified PMHS (PMHS-$C_{12}$) as prepared in Production Example 31. Specifically, 3 mL of toluene, 1 g of PMHS-$C_{12}$ as prepared in Production Example 31, and 30 mg of diphenyl ether were added to 1 g of the microfibrillated cellulose (cellulose nanofiber) fabricated by the method 3. Next, the mixture was heated to 60° C., and 10 mg of tris(pentafluorophenyl)borane was then added, followed by vigorous stirring for 10 minutes. This was followed by cooling to room temperature, then centrifugation for removal of the solution, and then three cycles of washing with hexane and centrifugation to remove the remaining unreacted PMHS-$C_{12}$ and catalyst. In this way, microfibrillated cellulose surface-modified with PMHS-$C_{12}$ (PMHS $C_{12}$-$C_{NF}$) was obtained. The reaction formula for the modification is shown below.

[Chemical Formula 50]

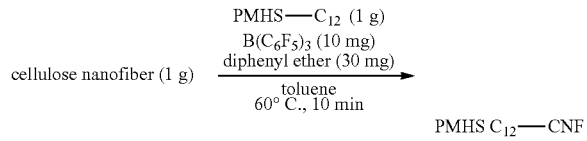

Figure 58:
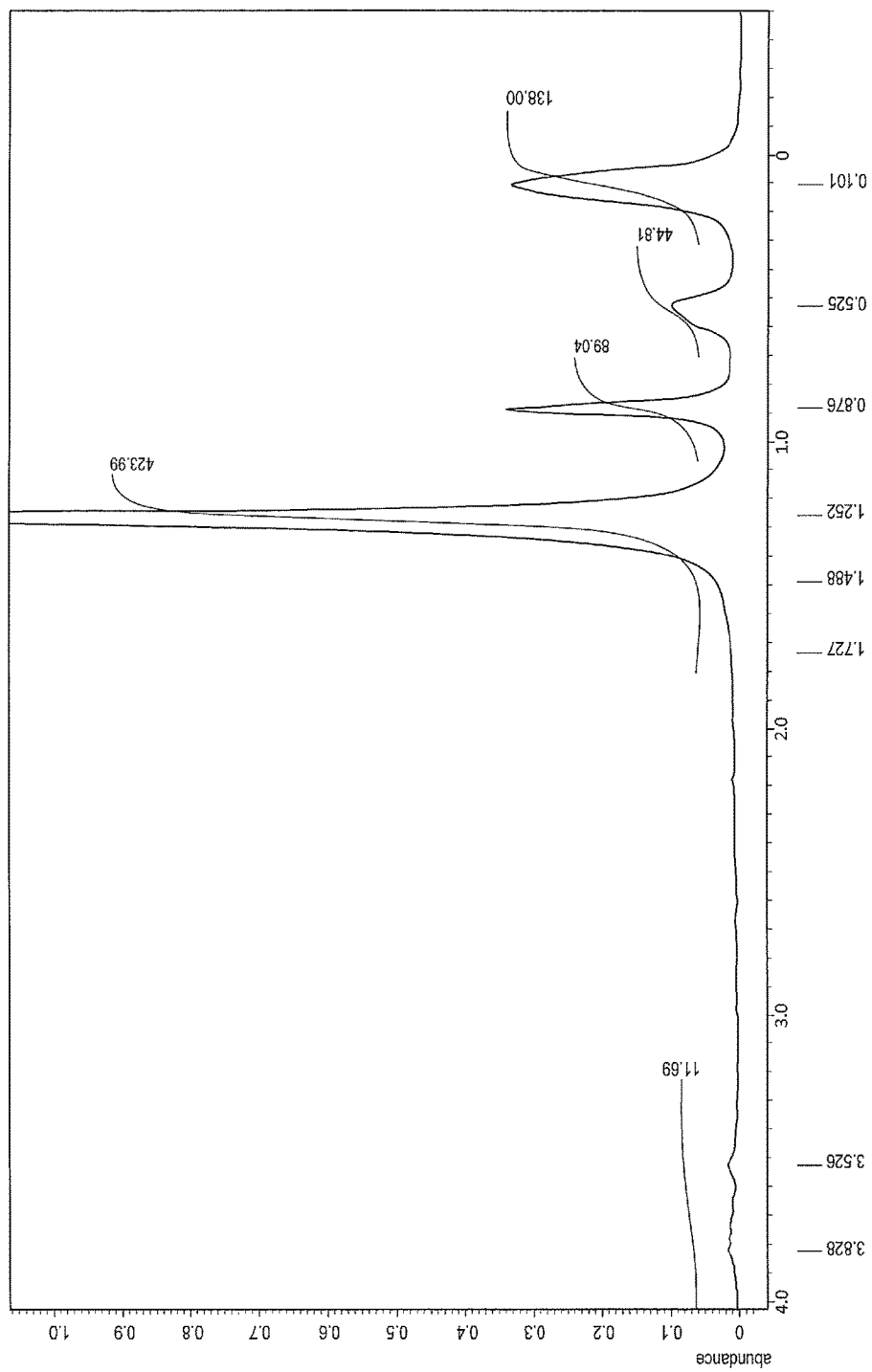
FIG. 58 shows a $^1$H-NMR profile of surface-modified cellulose nanofiber fabricated in Example 10-2.

Next, chloroform was added to the thus-fabricated modified microfibrillated cellulose, followed by centrifugation. The chloroform solution obtained by the centrifugation was concentrated, and the substances contained in the solution were identified by $^1$H-NMR measurement after dissolution in $CDCl_3$. The evaluation result is shown in FIG. 58. As shown in FIG. 58, additional peaks attributed to cellulose (peaks attributed to hydrogen atoms bonded to carbon atoms to which oxygen atoms are bonded in cellulose, that is, carbon atoms of the glucose skeleton) were observed at a chemical shift of around 3.5 to 3.9 ppm, which confirmed that the surface-modified cellulose nanofiber was dissolved in chloroform.

Similarly, when microfibrillated cellulose fabricated by a method described hereinafter was used instead of the microfibrillated cellulose fabricated by the method 3, silicone-modified cellulose nanofiber having its surface hydrophobized with PMHS-$C_{12}$ was obtained. The method is one in which Pure Pulp P50 (manufactured by SANYO KASEI Co., Ltd.) is subjected to reaction in acetonitrile according to an alcohol oxidation technique, reported by Ishihara et al. (Journal of American Chemical Society, 2009, vol. 131, pp. 251-262), which uses Potassium 2-Iodo-5-methylbenzene sulfonate and oxone. This method can be carried out in a non-aqueous system, which fact is of great industrial significance; for example, fabrication of cellulose nanofiber from pulp and surface modification of the fabricated nanofiber can be completed in the non-aqueous system.

Example 10-3

Surface Modification with PMHS-$C_{18}$

The surface of microfibrillated cellulose fabricated by the method 3 was modified with alkyl group ($C_{18}H_{37}$ group)-containing modified PMHS (PMHS-$C_{18}$) as prepared in Production Example 32. Specifically, microfibrillated cellulose surface-modified with PMHS-$C_{18}$ (PMHS Cis-CNF) was obtained by carrying out surface modification of microfibrillated cellulose with PMHS-$C_{18}$ in the same manner as in Example 10-2, except for using PMHS-$C_{18}$ instead of PMHS-$C_{12}$. The reaction formula for the modification is shown below.

[Chemical Formula 51]

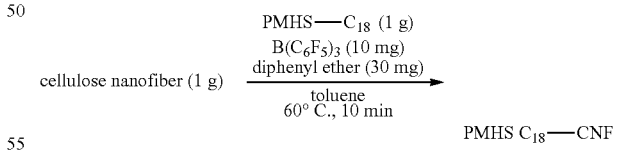

Figure 59:
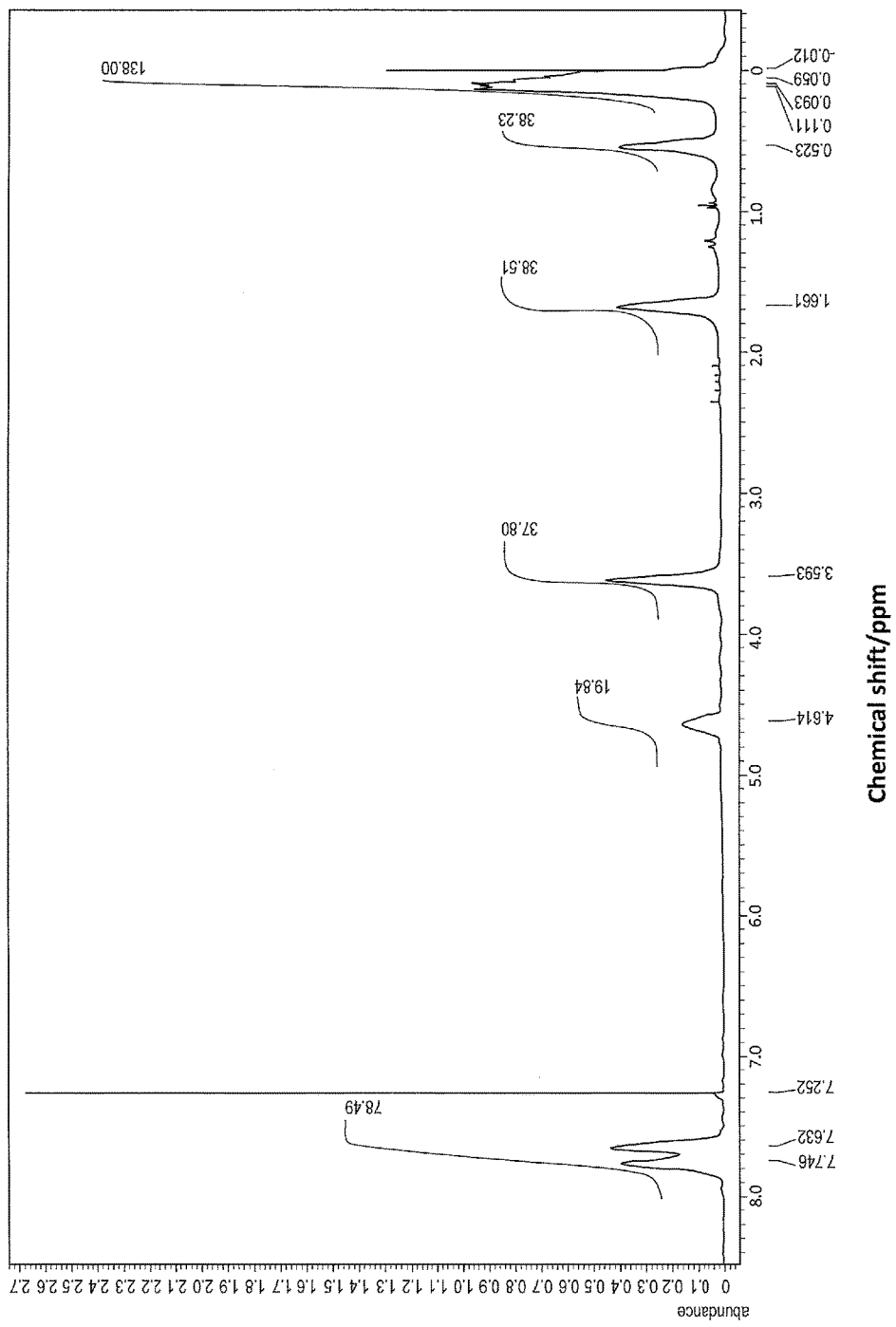
FIG. 59 shows a $^1$H-NMR profile of surface-modified cellulose nanofiber fabricated in Example 10-3.

Next, chloroform was added to the thus-fabricated modified microfibrillated cellulose, followed by centrifugation. The chloroform solution obtained by the centrifugation was concentrated, and the substances contained in the solution were identified by $^1$H-NMR measurement after dissolution in $CDCl_3$. The evaluation result is shown in FIG. 59. As shown in FIG. 59, additional peaks attributed to cellulose were observed at a chemical shift of around 3.5 to 3.9 ppm, which confirmed that the surface-modified cellulose nanofiber was dissolved in chloroform.

Similarly, when microfibrillated cellulose fabricated by subjecting Pure Pulp P50 to reaction in acetonitrile according to the alcohol oxidation technique reported by Ishihara et al. was used instead of the microfibrillated cellulose fabricated by the method 3, silicone-modified cellulose nanofiber having its surface hydrophobized with PMHS-$C_{18}$ was obtained.

Example 10-4

Repeated Modification of Pulp with PMHS

The surface of pulp was modified with PMHS, then the pulp was granulated, and the granulated pulp was further subjected to two repetitions of modification with PMHS. Thus, surface-modified pulp was obtained. Each modification process with PMHS was performed in the same manner as in Example 10-1, except for using pulp or granulated pulp instead of microfibrillated cellulose. When the surface-modified pulp obtained was dispersed in chloroform, the surface-modified pulp showed significantly higher dispersibility than unmodified pulp. It was thus confirmed that cellulose soluble in organic solvents can be obtained.

Example 11

Modification of Glass with Modified PMHS Having Perfluorohexylethyl Group

In Example 11, the surface of glass was modified with modified PMHS having a perfluorohexylethyl group (identical to modified PMHS as prepared in Production Example 33). Specifically, a glass sheet having a principal surface with an area of 4 cm$^2$ which was activated by corona treatment was put in a methylene chloride solution of 300 mg of (perfluorohexyl)ethylene, to which was further added 10 mg of diphenyl ether followed by 10 mg of tris(pentafluorophenyl)borane. After that, the reaction was allowed to proceed under sonication at room temperature for 10 minutes. The surface-modified glass thus obtained was washed thoroughly with hexane, and then the contact angle of water on the principal surface was measured. The contact angle was determined to be 108°.

Example 12

Modification of Surface of Cellulose with Nitrogen-Containing Hydrosilane

Example 12-1

To 200 mg of a 400-mesh cellulose powder (manufactured by Wako Pure Chemical Industries, Ltd.) were sequentially added 2 mL of cyclohexane, 1 g of (3-dimethylsilylpropyl)trifluoroacetylamide, and 10 mg of tris(pentafluorophenyl)borane. The mixture was then allowed to undergo reaction at room temperature under sonication for 10 minutes. Next, the reaction mixture was filtered, followed by washing with hexane and then by drying at room temperature to obtain an amide-modified cellulose powder. Evolution of hydrogen was observed during the reaction, and it was confirmed that hydrophobicity was imparted to the surface of the obtained cellulose. The reaction formula for the reaction is shown below. "N" in the right-hand side represents —NH(C=O)CF$_3$.

[Chemical Formula 52]

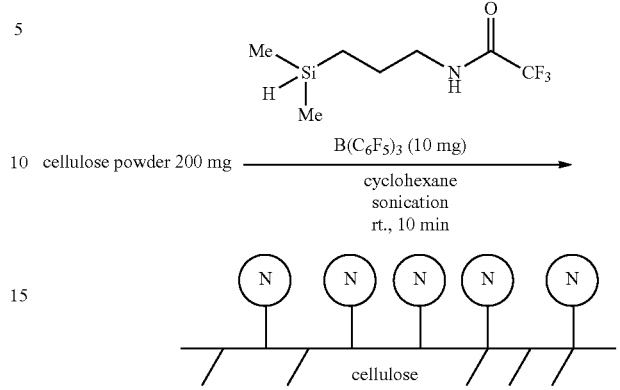

Example 12-2

An azido-modified cellulose powder was obtained in the same manner as in Example 12-1, except for using 0.7 g of (3-azidopropyl)dimethylsilane instead of 1 g of (3-dimethylsilylpropyl)trifluoroacetylamide. The reaction formula for the reaction is shown below. "N" in the right-hand side represents —N$_3$.

[Chemical Formula 53]

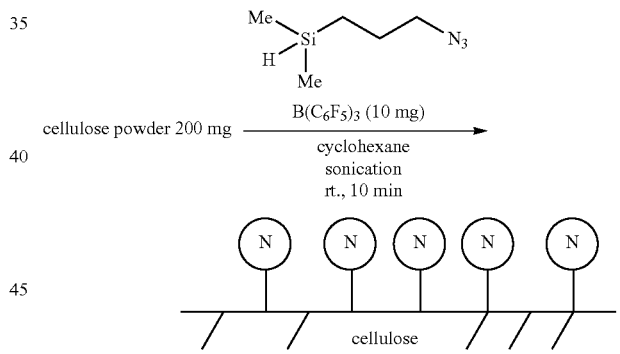

Example 12-3

To 200 mg of the cellulose powder as used in Example 12-1 were added 2 mL of toluene, 1 g of PMHS-Pht as prepared in Production Example 24, and 30 mg of diphenyl ether, followed by heating to 50° C. Next, 10 mg of tris(pentafluorophenyl)borane was added, followed by vigorous stirring for 10 minutes. The reaction mixture was then filtered, followed by washing with chloroform and then drying at room temperature to obtain a phthaloyl-modified cellulose powder. Vigorous evolution of hydrogen was observed during the reaction, and it was confirmed that hydrophobicity was imparted to the surface of the obtained cellulose. The reaction formula for the reaction is shown below. "N" in the right-hand side represents a phthaloyl group.

[Chemical Formula 54]

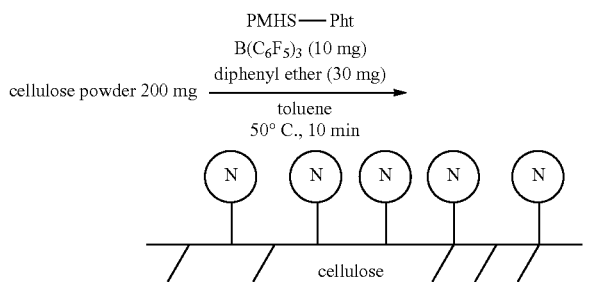

Example 13

Modification of Surface of Oxide

Example 13-1

Zirconium Oxide

First, a zirconium oxide powder (manufactured by Wako Pure Chemical Industries, Ltd.) was subjected to pretreatment, in which the powder was put in an eggplant-shaped flask and heated to dryness under vacuum. Next, 200 mg of the pretreated zirconium oxide, 4 mL of cyclohexane, 250 mg of polymethylhydrosiloxane, and several droplets of diphenyl ether were put in a dried eggplant-shaped flask. Subsequently, 5 mg of tris(pentafluorophenyl)borane was added, followed by stirring for 5 minutes. After completion of the stirring, the contents of the flask were filtered through a glass filter, and the solids separated by the filtration were vacuum-dried to obtain a surface-modified zirconium oxide powder.

Figure 60:
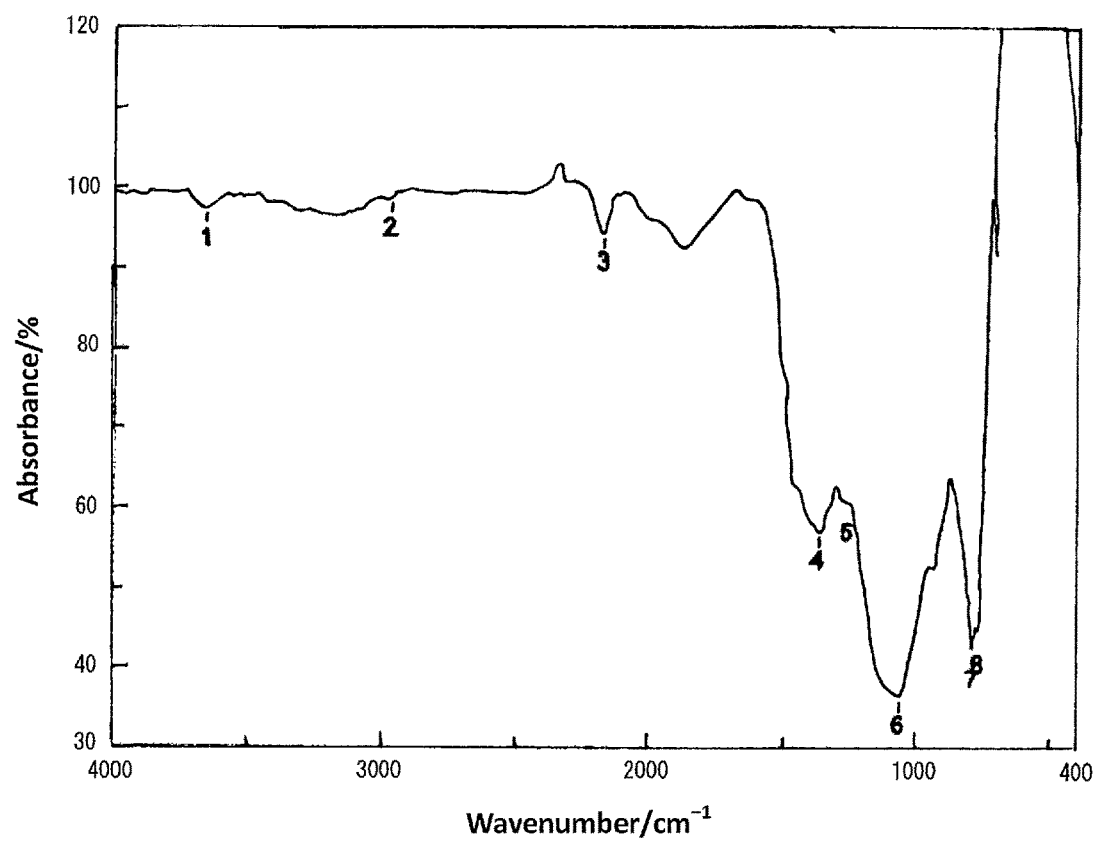
FIG. 60 shows an IR spectrum of a surface-modified zirconium oxide powder fabricated in Example 13-1.

The result of IR measurement of the obtained powder is shown in FIG. 60.

Figure 61:
FIG. 61 shows how a water droplet contacts a surface-modified zirconium oxide powder fabricated in Example 13-1.

The obtained zirconium oxide powder was spread thinly on a non-woven fabric, onto which a water droplet was dropped. The droplet took a form as shown in FIG. 61, which confirmed that water repellency was imparted to the zirconium oxide powder as a result of surface modification. The contact angle was 112° as visually observed. Given that the size of the droplet needed to be made much larger than normal to measure the contact angle of the droplet on the powder, the measured value can be presumed to be smaller than that of the contact angle which would be actually formed. This is the same for the values of the contact angle on powders which were evaluated in Examples 13-2 to 13-4.

Example 13-2

Indium Oxide

First, an indium oxide powder (manufactured by Wako Pure Chemical Industries, Ltd.) was subjected to pretreatment, in which the powder was put in an eggplant-shaped flask and heated to dryness under vacuum. Next, 200 mg of the pretreated indium oxide, 4 mL of cyclohexane, 250 mg of polymethylhydrosiloxane, and several droplets of diphenyl ether were put in a dried eggplant-shaped flask. Subsequently, 5 mg of tris(pentafluorophenyl)borane was added, followed by stirring for 5 minutes. After completion of the stirring, the contents of the flask were filtered through a glass filter, and the solids separated by the filtration were vacuum-dried to obtain a surface-modified indium oxide powder.

Figure 62:
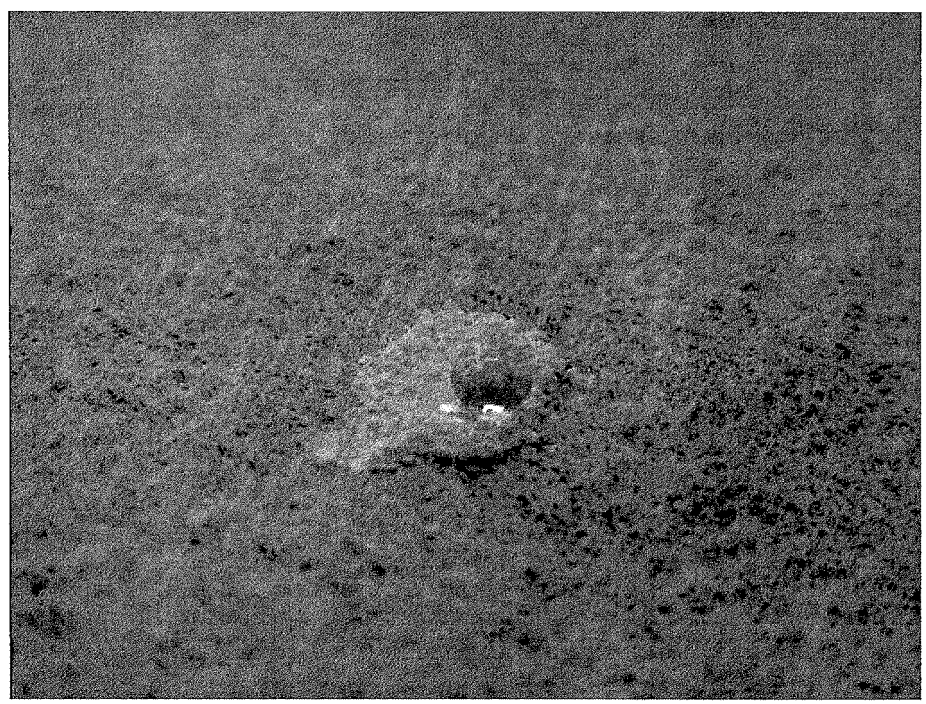
FIG. 62 shows how a water droplet contacts a surface-modified indium oxide powder fabricated in Example 13-2.

The obtained indium oxide powder was spread thinly on a non-woven fabric, onto which a water droplet was dropped. The droplet took a form as shown in FIG. 62, which confirmed that water repellency was imparted to the indium oxide powder as a result of surface modification. The contact angle was 118° as visually observed.

Example 13-3

Cerium Oxide

First, a cerium oxide powder (manufactured by Sigma-Aldrich Co. LLC.) was subjected to pretreatment, in which the powder was put in an eggplant-shaped flask and heated to dryness under vacuum. Next, 200 mg of the pretreated cerium oxide, 4 mL of cyclohexane, 250 mg of polymethylhydrosiloxane, and several droplets of diphenyl ether were put in a dried eggplant-shaped flask. Subsequently, 5 mg of tris(pentafluorophenyl)borane was added, followed by stirring for 5 minutes. After completion of the stirring, the contents of the flask were filtered through a glass filter, and the solids separated by the filtration were vacuum-dried to obtain a surface-modified cerium oxide powder.

Figure 63:
FIG. 63 shows how a water droplet contacts a surface-modified cerium oxide powder fabricated in Example 13-3.

The obtained cerium oxide powder was spread thinly on a non-woven fabric, onto which a water droplet was dropped. The droplet took a form as shown in FIG. 63, which confirmed that water repellency was imparted to the cerium oxide powder as a result of surface modification. The contact angle was 126° as visually observed.

Example 13-4

Titanium Oxide

First, a titanium oxide powder (manufactured by Wako Pure Chemical Industries, Ltd.) was subjected to pretreatment, in which the powder was put in an eggplant-shaped flask and heated to dryness under vacuum. Next, 200 mg of the pretreated titanium oxide, 4 mL of cyclohexane, 250 mg of polymethylhydrosiloxane, and several droplets of diphenyl ether were put in a dried eggplant-shaped flask. Subsequently, 5 mg of tris(pentafluorophenyl)borane was added, followed by stirring for 5 minutes. After completion of the stirring, the contents of the flask were filtered through a glass filter, and the solids separated by the filtration were vacuum-dried to obtain a surface-modified titanium oxide powder.

Figure 64:
FIG. 64 shows how a water droplet contacts a surface-modified titanium oxide powder fabricated in Example 13-4.

The obtained titanium oxide powder was spread thinly on a non-woven fabric, onto which a water droplet was dropped. The droplet took a form as shown in FIG. 64, which confirmed that water repellency was imparted to the titanium oxide powder as a result of surface modification. The contact angle was 118° as visually observed.

Example 13-5

Talc

To 1 g of particulate talc was added 4 mL of cyclohexane, followed by 600 mg of polymethylhydrosiloxane and then 10 mg of tris(pentafluorophenyl)borane. The mixture was stirred at room temperature for 5 minutes and then filtered through a glass filter, followed by washing with hexane. It was confirmed that the surface-modified talc thus obtained has water repellency and that even when, for example, floated on water for 1 week, the talc does not settle down by absorbing water.

Example 14

Support of Thio Compound on Wood Powder and Pulp as Well as Use of Thio Compound-Supported Product for Removal of Metal Ion

Example 14-1

In Example 14-1, thio compound-modified PMHS was synthesized by a reaction between PMHS and 3,6-dithia-1,8-octanediol. Specifically, 15.0 eq (5.58 g, 30.0 mmol) of 3,6-dithia-1,8-octanediol was first placed in a two-necked eggplant-shaped flask with an internal volume of 300 mL. Under nitrogen atmosphere, a solution of PMHS (4.9 mg, 2.0 mmol) dissolved in 150 mL of cyclohexane was added, and then 15 mg (0.03 mmol) of 1.5 mol % tris(pentafluorophenyl)borane was added, followed by stirring for 6 hours until hydrogen evolution ceased. In this way, thio compound-modified PMHS (3,6-dithia-1,8-octanedioxypolymethylhydrosiloxane) was obtained. The reaction formula for the reaction is shown below.

[Chemical Formula 55]

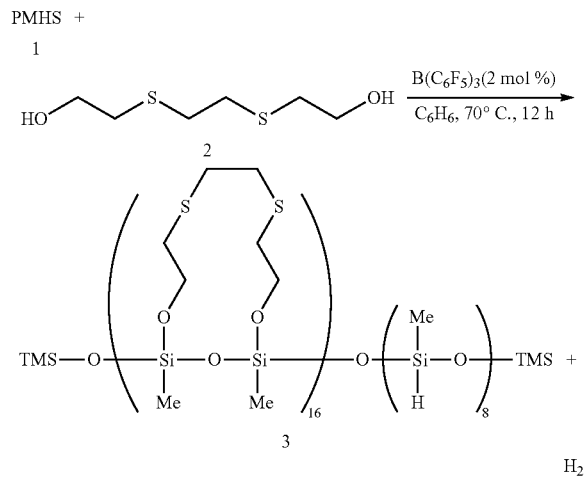

The thio compound-modified PMHS obtained was identified by $^1$H-NMR measurement. The chemical shifts determined were as follows.

δ (ppm): 4.61-4.87 (br, 27H), 3.79-4.10 (br, 26H), 2.65-2.89 (br, 52H), 0.06-0.32 (m, 138H)

Example 14-2

In Example 14-2, the surface of a wood powder was modified with thio compound-modified PMHS as prepared in Example 14-1, and the adsorption of metal ions on this surface was examined. Specific procedures were as follows. A wood powder was put in the stirred reaction solution as prepared in Example 14-1, and the solution was further stirred for 12 hours. Next, the wood powder was washed with diethyl ether and then dried. Subsequently, 20 g of the dried wood powder was packed in an elution tube, and 100 mL of an aqueous $CuSO_4$ solution with a concentration of 4.0 mmol/L was passed through the packed wood powder. The absorbance of the filtrate having passed through the wood powder was evaluated with an UV detector to determine the amount of $CuSO_4$ adsorbed on the wood powder. As a result, it was confirmed that 0.36 mmol of copper ions corresponding to 91% were removed by adsorption on the wood powder.

Preparation of Hydrosilane Compounds: Part 3

Production Example 39

Under nitrogen atmosphere, 1,4-dibromobenzene (5000 mg, 21.2 mmol) was dissolved in cyclopentyl methyl ether (CPME; 25 mL), the resulting solution was cooled to −5° C., and then $^n$BuLi (13.5 mL, 21.2 mmol) and iPrMgCl (8.15 mL, 10.6 mmol) were added, followed by stirring for 2 hours. Next, chlorodimethylsilane (2.47 mL, 22.3 mmol) was added, followed by stirring at room temperature for 2 hours to allow the reaction to proceed. After completion of the reaction, a saturated aqueous $NH_4Cl$ solution was added for quenching, and the aqueous layer was extracted with diethyl ether. The resulting organic layer was then washed with a saturated aqueous NaCl solution and dried over $MgSO_4$. This was followed by filtration and concentration to obtain a crude product. Finally, the crude product was purified by silica gel column chromatography to obtain a compound (4235 mg, yield=93%) shown in the right-hand side of the following reaction formula.

[Chemical Formula 56]

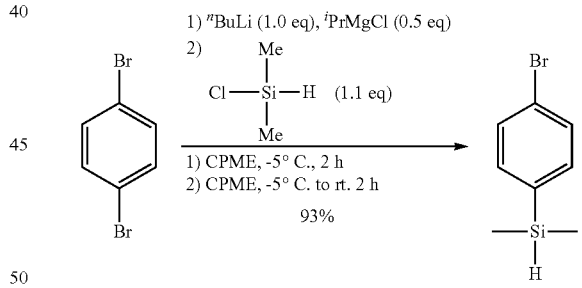

The compound obtained was identified by $^1$H-NMR measurement. The chemical shifts determined were as follows.

δ (ppm): 0.33 (d, J=4.0 Hz, 6H), 4.42-4.36 (m, 1H), 7.40 (d, J=8.4 Hz, 2H), 7.50 (d, J=8.0 Hz, 2H)

Next, under nitrogen atmosphere, Mg (669 mg, 27.9 mmol) was dipped in THF (2 mL), to which a small amount of dibromoethane was added to activate Mg. The compound obtained as above (4000 mg, 18.6 mmol) and THF (13 mL) were then added dropwise at room temperature, followed by stirring for 2 hours to obtain 4-dimethylsilylphenylmagnesium bromide (0.9 M) which is a compound shown in the right-hand side of the following reaction formula. This compound is a new hydrosilane compound.

[Chemical Formula 57]

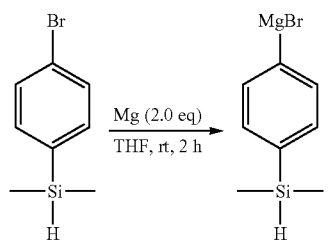

Next, under nitrogen atmosphere, DMF (1.23 mL, 15.9 mmol) was put in a reaction vessel and, after cooling to 0° C., the 4-dimethylsilylphenylmagnesium bromide obtained (18.0 mL, 16.7 mmol) was added dropwise as a Grignard reagent, followed by stirring at room temperature for 2 hours to allow the reaction to proceed. After completion of the reaction, a saturated aqueous NH₄Cl solution was added for quenching, and the aqueous layer was extracted with diethyl ether. The resulting organic layer was washed with a saturated aqueous NaCl solution and dried over MgSO₄. This was followed by filtration and concentration to obtain a crude product. The crude composition obtained was then purified by silica gel column chromatography to obtain a compound (2213 mg, yield=72%) shown in the right-hand side of the following reaction formula.

[Chemical Formula 58]

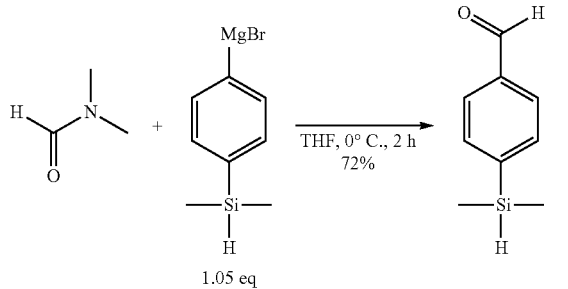

The compound obtained was identified by ¹H-NMR measurement. The chemical shifts determined were as follows.

δ (ppm): 0.39 (d, J=4.4 Hz, 6H), 4.50-4.44 (m, 1H), 7.72 (d, J=7.6 Hz, 2H), 7.85 (d, J=8.4 Hz, 2H), 10.0 (s, 1H)

Next, under nitrogen atmosphere, the compound obtained (1000 mg, 6.09 mmol) was dissolved in CH₂Cl₂ (14 mL), and BF₃.Et₂O (172.7 mg, 1.22 mmol) and 1,2-ethanedithiol (630 mg, 6.70 mmol) were added, followed by stirring at room temperature for 6 hours to allow the reaction to proceed. Completion of the reaction was followed by washing with water and then by extraction of the aqueous layer with CH₂Cl₂. The resulting organic layer was dried over MgSO₄ and then filtered, followed by concentration to obtain a crude product. Finally, the crude product obtained was purified by silica gel column chromatography to obtain 4-(1,3-dithian-2-yl)dimethylsilylbenzene (1398 mg, yield=96%) which is a compound shown in the right-hand side of the following reaction formula. This compound is a new hydrosilane compound.

[Chemical Formula 59]

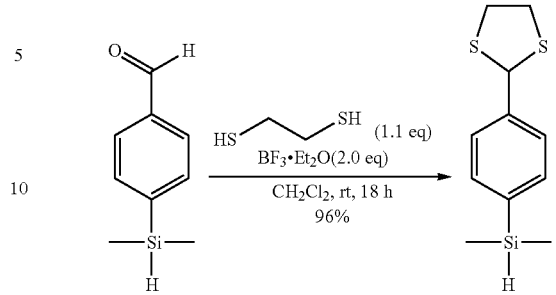

The compound obtained was identified by ¹H-NMR measurement. The chemical shifts determined were as follows.

δ (ppm): 0.34 (d, J=3.6 Hz, 6H), 3.56-3.33 (m, 4H), 4.44-4.39 (m, 1H), 5.64 (s, 1H), 7.51 (d, J=2.8 Hz, 4H)

Production Example 40

A solution of (3-bromopropyl)dimethylsilane (543 mg, 3 mmol) and triethylamine (306 mg, 3 mmol) in anhydrous acetonitrile (2 mL) was put inside a sealed tube under nitrogen atmosphere and stirred at 80° C. for 20 hours. The resulting mixture was concentrated under reduced pressure, and the remaining white solids were washed with an ether and then dried under reduced pressure to obtain triethyl-3-(dimethylsilylpropyl)ammonium bromide (735 mg, 2.6 mmol) in a yield of 87%. This compound is a new hydrosilane compound.

The reaction formula for the reaction is shown below.

[Chemical Formula 60]

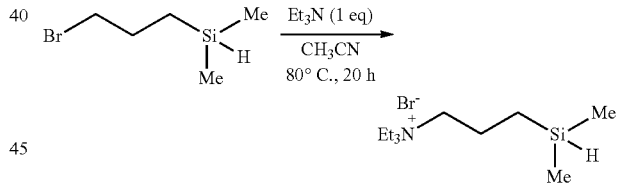

The compound obtained was identified by ¹H-NMR measurement. The chemical shifts determined were as follows.

δ (ppm): 3.87-3.92 (m, 1H), 3.50-3.56 (q, J=6.8 Hz, 6H), 3.30-3.35 (m, 2H), 1.69-1.77 (m, 2H), 1.39-1.43 (t, J=7.2 Hz, 9H), 0.64-0.69 (m, 2H), 0.13-0.14 (d, J=3.6 Hz, 6H)

Production Example 41

Under nitrogen atmosphere, (3-azidopropyl)dimethylsilane (1144 mg, 8.0 mmol) was added to a solution of triphenylphosphine (2306 mg, 8.8 mmol) in diethyl ether (9 mL), followed by stirring at room temperature for 12 hours to allow the reaction to proceed. After completion of the reaction, the ether was distilled off under reduced pressure, so that N-dimethylhydrosilylpropyliminotriphenylphosphorane was obtained. This compound is a new hydrosilane compound. The reaction formula for the reaction is shown below.

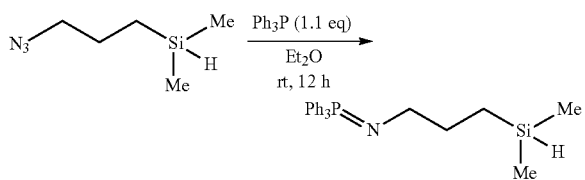

Next, H₂O (0.87 mL, 48 mmol) was added to the N-dimethylhydrosilylpropyliminotriphenylphosphorane obtained, followed by further stirring at room temperature for 24 hours to allow the reaction to proceed. The resulting reaction mixture was then dried over Na₂SO₄ and subjected to Celite filtration, followed by concentration under reduced pressure. The crude product thus obtained was purified by distillation to obtain (3-aminopropyl)dimethylsilane (702 mg, 6.0 mmol) in a yield of 75%. This method provides an improved yield of (3-aminopropyl)dimethylsilane as compared to the method in Production Example 8.

The reaction formula for the reaction from the starting material is shown below.

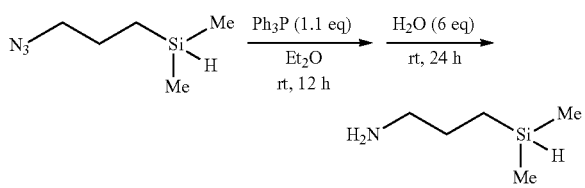

The (3-aminopropyl)dimethylsilane obtained was identified by $^1$H-NMR measurement and $^{13}$C-NMR measurement. The chemical shifts determined were as follows.

$^1$H-NMR δ (ppm): 3.83-3.89 (m, 1H), 2.67-2.70 (t, J=6.8 Hz, 2H), 1.44-1.52 (m, 2H), 1.38 (bs, 2H), 0.56-0.61 (m, 2H), 0.07-0.08 (d, J=3.6 Hz, 6H); 3C-NMR δ (ppm): −4.37, 11.28, 28.84, 45.37

Production Example 42

(3-chloropropyl)methylsilane (6.10 g, 50 mmol) was added to a solution of sodium azide (4.68 g, 60 mol) in DMF (60 mL), followed by stirring at 60° C. for 12 hours. Next, the stirred mixture was cooled to room temperature, and then distilled water was added, followed by liquid-liquid separation with pentane. Subsequently, the resulting pentane layer was washed with brine, dried over sodium sulfate, and filtered, followed by concentration under reduced pressure to obtain (3-azidopropyl)methylsilane (6.0 g, 47 mmol) in a yield of 93%. The reaction formula for the reaction is shown below.

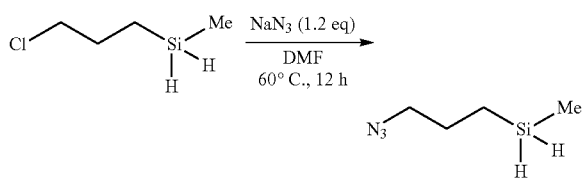

The (3-azidopropyl)methylsilane obtained was identified by $^1$H-NMR measurement. The chemical shifts determined were as follows.

δ (ppm): 3.71-3.76 (quin., J=4.0 Hz, 2H), 3.26-3.29 (t, J=6.8 Hz, 2H), 1.65-1.72 (m, 2H), 0.71-0.77 (m, 2H), 0.15-0.17 (t, J=4.4 Hz, 3H)

Next, a solution of triphenylphosphine (2885 mg, 11 mmol) in diethyl ether (50 mL) was cooled to 0° C., and the (3-azidopropyl)methylsilane obtained (1290 mg, 10 mol) was added dropwise slowly. The reaction mixture thus obtained was stirred at room temperature for 4 hours, after which the ether was distilled off under reduced pressure, so that N-methyldihydrosilylpropyliminotriphenylphosphorane was obtained. This compound is a new hydrosilane compound. The reaction formula for the reaction is shown below.

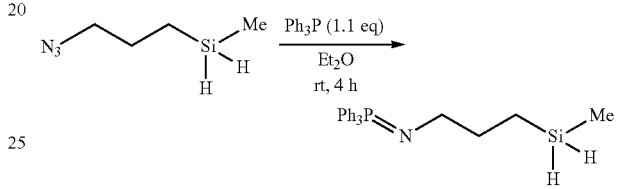

Next, H₂O (0.22 mL, 12 mmol) was added to the N-methyldihydrosilylpropyliminotriphenylphosphorane obtained, followed by stirring for 4 hours. After that, sodium sulfate was added for removal of the remaining unreacted water, followed by filtration. The resulting solution was distilled under reduced pressure to obtain (3-aminopropyl)methylsilane (484 mg, 4.7 mmol) in a yield of 47%. The reaction formula for the reaction starting from (3-azidopropyl)methylsilane is shown below.

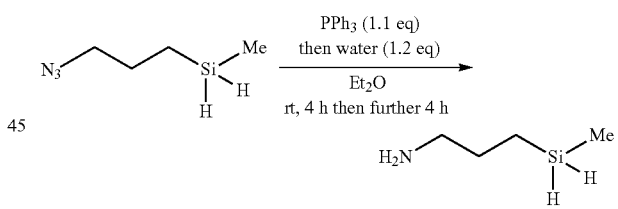

(3-aminopropyl)methylsilane obtained was identified by $^1$H-NMR measurement. The chemical shifts determined were as follows.

δ (ppm): 3.67-3.72 (quin., J=4.0 Hz, 2H), 2.66-2.70 (t, J=6.8 Hz, 2H), 1.48-1.55 (m, 4H), 0.64-0.70 (m, 2H), 0.13-0.15 (t, J=4.4 Hz, 3H)

INDUSTRIAL APPLICABILITY

The surface-modified base material obtained by the production method according to the present invention can be used in various applications depending on the type of the base material, the type of the molecular structure A modifying the surface of the base material, and the degree of modification.

The present invention may be embodied in other forms without departing from the spirit or essential characteristics thereof. The embodiments disclosed in this specification are to be considered in all respects as illustrative and not limiting. The scope of the present invention is indicated by the appended claims rather than by the foregoing description, and all changes which come within the meaning and range of equivalency of the claims are intended to be embraced therein.

The invention claimed is:

1. A method for producing a surface-modified base material, comprising a step of bringing a base material having a polar group present on a surface thereof into contact with a hydrosilane compound having a molecular structure A and having a Si—H group composed of a silicon atom of the molecular structure A and a hydrogen atom bonded to the silicon atom in the presence of a borane catalyst so as to allow a dehydrocondensation reaction to take place between the base material and the compound, thereby forming the base material surface-modified with the molecular structure A, wherein
the base material is a flat sheet, a bulk material, a porous body, a flake, a particle, a powder, or a fiber.

2. The method for producing a surface-modified base material according to claim 1, wherein the polar group is a hydroxy group and/or a carbonyl group.

3. The method for producing a surface-modified base material according to claim 1, wherein the polar group is a hydroxy group.

4. The method for producing a surface-modified base material according to claim 1, wherein the catalyst is tris(pentafluorophenyl)borane.

5. The method for producing a surface-modified base material according to claim 1, wherein the base material is composed of a non-metal substance.

6. The method for producing a surface-modified base material according to claim 1, wherein the base material is a flake, a particle, or a fiber.

7. The method for producing a surface-modified base material according to claim 1, wherein the step is carried out at a temperature lower than 50° C.

8. A method for producing a joined body, comprising a step of bringing a plurality of base materials each having a polar group present on a surface thereof into contact with a hydrosilane compound having a molecular structure A and having two or more Si—H groups each composed of a silicon atom of the molecular structure A and a hydrogen atom bonded to the silicon atom in the presence of a borane catalyst so as to allow a dehydrocondensation reaction to take place between the base materials and the compound, thereby obtaining a joined body including the plurality of base materials joined together via the molecular structure A acting as a junction structure.

9. The method for producing a joined body according to claim 8, wherein the polar group is a hydroxy group and/or a carbonyl group.

10. The method for producing a joined body according to claim 8, wherein the base materials are each independently a flake, a particle, or a fiber.

11. A new hydrosilane compound, selected from the following compounds: 1-(dimethylsilyl)pyrene, 1-(3-dimethylsilylpropyl)naphthalene, (3-azidopropyl)dimethylsilane, [3-(dimethylsilyl)propyl]acrylamide, 1-(3-dimethylsilylpropyl)-3-methylimidazolium iodide, (3-nitropropyl)dimethylsilane, 4-(dimethylsilyl)butyric acid, ethyl 4-(dimethylsilyl)butyrate, [3-(dimethylsilyl)propyl] diethylphosphate, 4-(dimethylsilyl)butanol, (3-benzoylpropyl)dimethylsilane, 5,6-epoxyhexyldimethylsilane, (3-dimethylsilylpropyl)trifluoroacetamide, phthaloylpolymethylhydrosiloxane, chloropropylpolymethylhydrosiloxane, 3-aminopropylpolymethylhydrosiloxane, 3-chloropropyl-isopropoxypolymethylhydrosiloxane, 3-azidopropylpolymethylhydrosiloxane, 3-bromopropylpolymethylhydrosiloxane, octadecylpolymethylhydrosiloxane, perfluorohexylethylpolymethylhydrosiloxane, allylpolymethylhydrosiloxane, chloroisopropoxypolymethylhydrosiloxane, a modified polymethylhydrosiloxane having at least one unit selected from units respectively indicated by the following fomula (a), (b) or (c), a modified polymethylhydrosiloxane having an unit indicated by the following formula (d), a modified polymethylhydrosiloxane having an unit indicated by the following formula (e), N-dimethylhydrosilylpropyliminotriphenylphosphorane, N-methyldihydrosilylpropyliminotriphenylphosphorane, 4-dimethylsilylphenylmagnesium bromide, 4-(1,3-dithian-2-yl)dimethylsilylbenzene, and triethyl-3-(dimethylsilylpropyl)ammonium bromide,

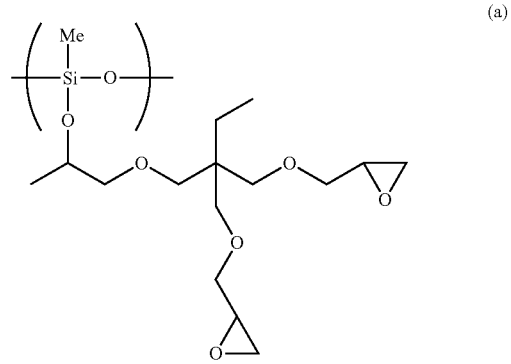

(a)

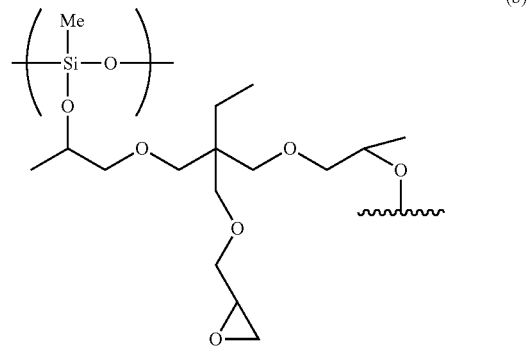

(b)

∿∿∿ a crosslinked or uncrosslinked polymethylhydrogensiloxane

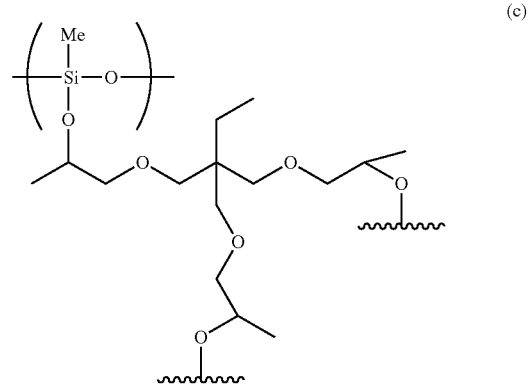

(c)

∿∿∿ a crosslinked or uncrosslinked polymethylhydrogensiloxane (d)

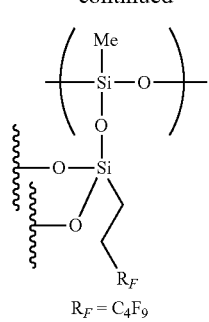

$R_F = C_4F_9$

⌇⌇⌇ a crosslinked or uncrosslinked polymethylhydrogensiloxane (e)

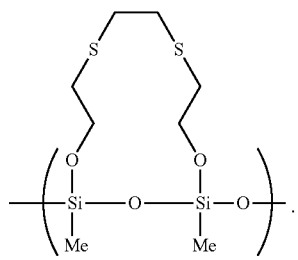

12. A surface-modified base material, obtained by the method for producing a surface-modified base material according to claim 1, the surface-modified base material comprising a base material surface-modified with the molecular structure A, wherein
the base material is cellulose nanofiber.

13. A surface-modified base material, obtained by a method for producing a surface-modified base material according to claim 1, wherein
the base material is surface-modified with the molecular structure A, and
the hydrosilane compound is a hydrosilane compound selected from the following compounds: 1-(dimethylsilyl)pyrene, (dimethylsilyl)ferrocene, 1-(3-dimethylsilylpropyl)naphthalene, (3-azidopropyl)dimethylsilane, [3-(dimethylsilyl)propyl]acrylamide, 1-(3-dimethylsilylpropyl)-3-methylimidazolium iodide, (3-nitropropyl)dimethylsilane, 4-(dimethylsilyl)butyric acid, ethyl 4-(dimethylsilyl)butyrate, [3-(dimethylsilyl)propyl] diethylphosphate, 4-(dimethylsilyl)butanol, (3-benzoylpropyl)dimethylsilane, 5,6-epoxyhexyldimethylsilane, (3-dimethylsilylpropyl)trifluoroacetamide, phthaloylpolymethylhydrosiloxane, chloropropylpolymethylhydrosiloxane, 3-aminopropylpolymethylhydrosiloxane, 3-acetoxypropylpolymethylhydrosiloxane, 3-chloropropyl-isopropoxypolymethylhydrosiloxane, 3-azidopropylpolymethylhydrosiloxane, 3-bromopropylpolymethylhydrosiloxane, dodecylpolymethylhydrosiloxane, octadecylpolymethylhydrosiloxane, perfluorohexylethylpolymethylhydrosiloxane, allylpolymethylhydrosiloxane, 1,2-epoxypropylpolymethylhydrosiloxane, chloroisopropoxypolymethylhydrosiloxane, a modified polymethylhydrosiloxane having at least one unit selected from units respectively indicated by the following fomula (a), (b) or (c), a modified polymethylhydrosiloxane having an unit indicated by the following formula (d), a modified polymethylhydrosiloxane having an unit indicated by the following formula (e), N-dimethylhydrosilylpropyliminotriphenylphosphorane, N-methyldihydrosilylpropyliminotriphenylphosphorane, 4-dimethylsilylphenylmagnesium bromide, 4-(1,3-dithian-2-yl)dimethylsilylbenzene, and triethyl-3-(dimethylsilylpropyl)ammonium bromide, (a)

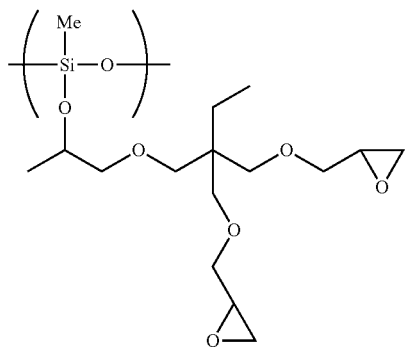

(b)

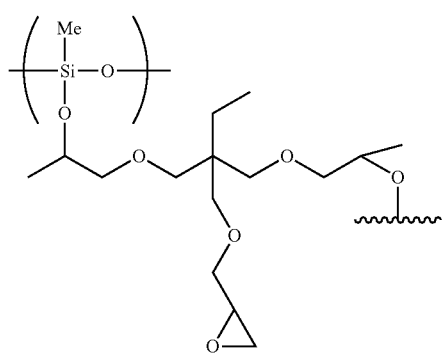

⌇⌇⌇ a crosslinked or uncrosslinked polymethylhydrogensiloxane (c)

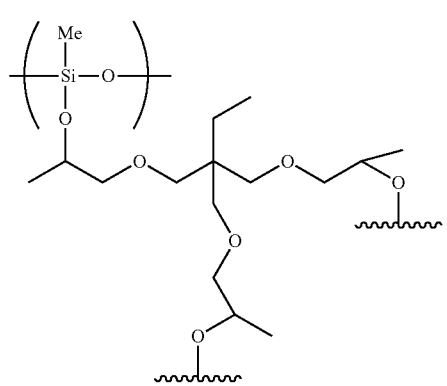

⌇⌇⌇ a crosslinked or uncrosslinked polymethylhydrogensiloxane (d)

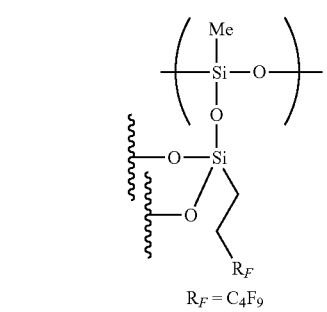

$R_F = C_4F_9$

⌇⌇⌇ a crosslinked or uncrosslinked polymethylhydrogensiloxane

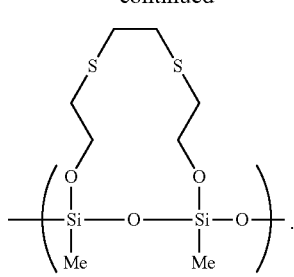

(e)

14. A method for producing a surface-modified base material, comprising a step of bringing a base material having a polar group present on a surface thereof into contact with a hydrosilane compound having a molecular structure A and having a Si—H group composed of a silicon atom of the molecular structure A and a hydrogen atom bonded to the silicon atom in the presence of a borane catalyst so as to allow a dehydrocondensation reaction to take place between the base material and the compound, thereby forming the base material surface-modified with the molecular structure A, wherein
the base material is a wood, a non-wood vegetable material, a natural polymer, a synthetic polymer, a talc, an apatite, a graphene, or a carbon nanotube.

15. A method for producing a surface-modified base material, comprising a step of bringing a base material having a polar group present on a surface thereof into contact with a hydrosilane compound having a molecular structure A and having a Si—H group composed of a silicon atom of the molecular structure A and a hydrogen atom bonded to the silicon atom in the presence of a borane catalyst so as to allow a dehydrocondensation reaction to take place between the base material and the compound, thereby forming the base material surface-modified with the molecular structure A, wherein
at least a part of the surface of the base material is composed of at least one substance selected from the group consisting of a metal oxide, a silica, a glass, a ceramic, and a hydroxy group-containing resin.

16. A method for producing a surface-modified base material, comprising a step of bringing a base material having a polar group present on a surface thereof into contact with a hydrosilane compound having a molecular structure A and having a Si—H group composed of a silicon atom of the molecular structure A and a hydrogen atom bonded to the silicon atom in the presence of a borane catalyst so as to allow a dehydrocondensation reaction to take place between the base material and the compound, thereby forming the base material surface-modified with the molecular structure A, wherein
the hydrosilane compound is a hydrosilane compound selected from the following compounds: 1-(dimethylsilyl)pyrene, (dimethyl silyl)ferrocene, 1-(3-dimethylsilylpropyl)naphthalene, (3-azidopropyl)dimethylsilane, [3-(dimethylsilyl)propyl]acrylamide, 1-(3-dimethylsilylpropyl)-3-methylimidazolium iodide, (3-nitropropyl)dimethylsilane, 4-(dimethylsilyl)butyric acid, ethyl 4-(dimethyl silyl)butyrate, [3-(dimethylsilyl)propyl] diethylphosphate, 4-(dimethylsilyl)butanol, (3-benzoylpropyl)dimethylsilane, 5,6-epoxyhexyldimethylsilane, (3-dimethylsilylpropyl)trifluoroacetamide, phthaloylpolymethylhydrosiloxane, chloropropylpolymethylhydrosiloxane, 3-aminopropylpolymethylhydrosiloxane, 3-acetoxypropylpolymethylhydrosiloxane, 3-chloropropyl-isopropoxypolymethylhydrosiloxane, 3-azidopropylpolymethylhydrosiloxane, 3-bromopropylpolymethylhydrosiloxane, dodecylpolymethylhydrosiloxane, octadecylpolymethylhydrosiloxane, perfluorohexylethylpolymethylhydrosiloxane, allylpolymethylhydrosiloxane, 1,2-epoxypropylpolymethylhydrosiloxane, chloroisopropoxypolymethylhydrosiloxane, a modified polymethylhydrosiloxane having at least one unit selected from units respectively indicated by the following fomula (a), (b) or (c), a modified polymethylhydrosiloxane having an unit indicated by the following formula (d), a modified polymethylhydrosiloxane having an unit indicated by the following formula (e), N-dimethylhydrosilylpropyliminotriphenylphosphorane, N-methyldihydrosilylpropyliminotriphenylphosphorane, 4-dimethylsilylphenylmagnesium bromide, 4-(1,3-dithian-2-yl)dimethylsilylbenzene, and triethyl-3-(dimethylsilylpropyl)ammonium bromide,

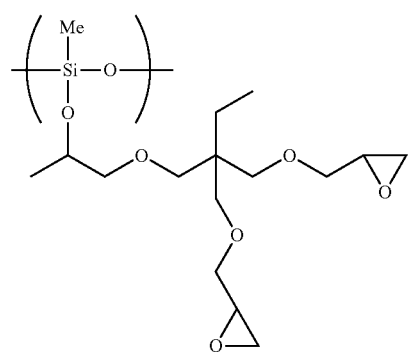

(a)

(b)

~~~ a crosslinked or uncrosslinked polymethylhydrogensiloxane

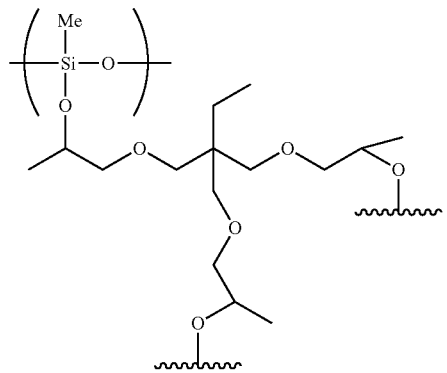

(c)

~~~ a crosslinked or uncrosslinked polymethylhydrogensiloxane

-continued
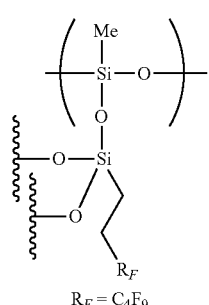
(d)
$R_F = C_4F_9$
∿∿∿ a crosslinked or uncrosslinked polymethylhydrogensiloxane
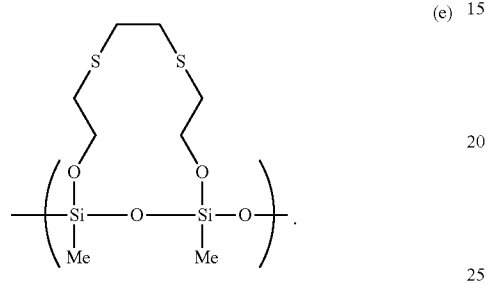
(e)
17. A surface-modified base material, obtained by the method for producing a surface-modified base material according to claim 14, the surface-modified base material comprising a base material surface-modified with the molecular structure A.
* * * * *